United States Patent
Liu et al.

(10) Patent No.: US 11,358,950 B2
(45) Date of Patent: Jun. 14, 2022

(54) SMAC MIMETICS USED AS IAP INHIBITORS AND USE THEREOF

(71) Applicant: CHIA TAI TIANQING PHARMACEUTICAL GROUP CO., LTD., Jiangsu (CN)

(72) Inventors: Yingchun Liu, Shanghai (CN); Zhaobing Xu, Shanghai (CN); Lihong Hu, Shanghai (CN); Charles Z. Ding, Shanghai (CN); Xingxun Zhu, Shanghai (CN); Guoping Hu, Shanghai (CN); Jian Li, Shanghai (CN); Shuhui Chen, Shanghai (CN)

(73) Assignee: CHIA TAI TIANGQING PHARMACEUTICAL GROUP CO., LTD., Jiangsu (CN)

( * ) Notice: Subject to any disclaimer, the term of this patent is extended or adjusted under 35 U.S.C. 154(b) by 3 days.

(21) Appl. No.: 16/763,746

(22) PCT Filed: Nov. 13, 2018

(86) PCT No.: PCT/CN2018/115256
§ 371 (c)(1),
(2) Date: May 13, 2020

(87) PCT Pub. No.: WO2019/091492
PCT Pub. Date: May 16, 2019

(65) Prior Publication Data
US 2021/0371400 A1    Dec. 2, 2021

(30) Foreign Application Priority Data

Nov. 13, 2017 (CN) .......................... 201711117079.6

(51) Int. Cl.
| C07D 403/06 | (2006.01) |
| C07D 403/14 | (2006.01) |
| C07D 413/14 | (2006.01) |
| C07D 471/04 | (2006.01) |
| A61P 35/00 | (2006.01) |

(52) U.S. Cl.
CPC ............ *C07D 403/06* (2013.01); *A61P 35/00* (2018.01); *C07D 403/14* (2013.01); *C07D 413/14* (2013.01); *C07D 471/04* (2013.01)

(58) Field of Classification Search
CPC .. C07D 403/06; C07D 403/14; C07D 413/14; C07D 471/04
See application file for complete search history.

(56) References Cited

U.S. PATENT DOCUMENTS

| 9,586,991 B2 | 3/2017 | Cohen et al. |
| 2010/0256115 A1 | 10/2010 | Cohen et al. |
| 2011/0015232 A1 | 1/2011 | Charest et al. |
| 2011/0288116 A1 | 11/2011 | Condon et al. |
| 2012/0015974 A1 | 1/2012 | Koehler |
| 2014/0080805 A1 | 3/2014 | Cohen et al. |

FOREIGN PATENT DOCUMENTS

| CN | 101035802 A | 9/2007 |
| CN | 101146803 A | 3/2008 |
| CN | 101595121 A | 12/2009 |
| CN | 101605786 A | 12/2009 |
| CN | 101951766 A | 1/2011 |
| CN | 104159897 A | 11/2014 |
| WO | 2008/014252 A2 | 1/2008 |

OTHER PUBLICATIONS

Zhao et el. Cells 2020, 9, p. 1-25. (Year: 2020).*
Lalaoui et al. Cell Death & Differentiation (2020) 27:2768-2780. (Year: 2020).*
ISA/CN, International Search Report for PCT/CN2018/115256 (dated Feb. 13, 2019) (English translation).
PCT International Preliminary Report on Patentability in International Appln. No. PCT/CN2018/115256, dated May 19, 2020, 15 pages (with English Translation).
PCT Written Opinion of the International Search Authority in International Appln. No. PCT/CN2018/115256, dated Feb. 13, 2019, 11 pages (with English Translation).
Extended Search Report in European Appln. No. 18875727.2, dated Jul. 1, 2021, 4 pages.
Fulda, "Smac mimetics as IAP antagonists," Seminars in Cell & Developmental Biology, 2015, 39:132-138.
Office Action in Chinese Appln. No. 201880070118.8, dated Jul. 28, 2021, 9 pages (with English Translation).

* cited by examiner

*Primary Examiner* — Erich A Leeser
(74) *Attorney, Agent, or Firm* — Fish & Richardson P.C.

(57) ABSTRACT

Disclosed are a class of SMAC mimetics used as IAP inhibitors, and in particular disclosed are compounds as shown in formula (I), isomers thereof, and pharmaceutically acceptable salts thereof. The IAP inhibitors are drugs for treating cancers, in particular breast cancer.

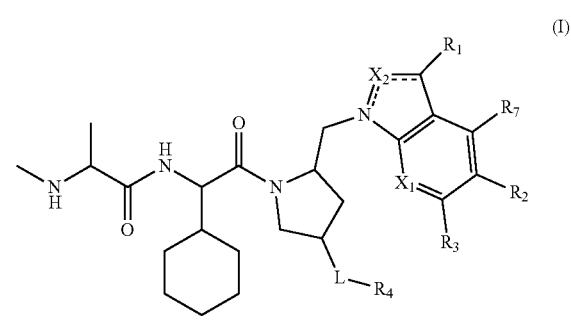

19 Claims, No Drawings

SMAC MIMETICS USED AS IAP INHIBITORS AND USE THEREOF

CROSS-REFERENCE TO RELATED APPLICATIONS

The present application is a U.S. National Phase application under 35 U.S.C. § 371 of International Patent Application No. PCT/CN2018/115256, filed on Nov. 13, 2018, which claims the priority and benefit of Chinese Patent Application No. 201711117079.6 filed with the National Intellectual Property Administration, PRC on Nov. 13, 2017, the disclosed contents of which are incorporated herein by reference in its entirety.

TECHNICAL FIELD

The present disclosure describes a compound that inhibits IAP (inhibitor of apoptosis proteins), the preparation process thereof, and the use thereof in the treatment of various diseases. The compounds of the present disclosure are used to treat cancer, autoimmune diseases, and other diseases involving defects in cell apoptosis.

BACKGROUND

Programmed cell death plays a key role in regulating the number of cells and removing stressed or damaged cells from normal tissues. In fact, the apoptosis signaling network mechanism inherent in most types of cells provides a major barrier against the development and progression of human cancer. However, the commonality of all cancer cells is that they cannot perform the apoptosis process and lack proper apoptosis due to the lack of normal apoptosis mechanism. Currently, most cancer therapies, including chemotherapy, radiation therapy, and immunotherapy, function by indirectly inducing cancer cell apoptosis. Thus, the inability of cancer cells to perform the apoptosis process due to the defects in normal apoptosis mechanism is often associated with the increased resistance to the cell apoptosis induced by chemotherapy, radiation therapy or immunotherapy. Therefore, aiming at directly inhibiting a key negative regulatory factor that plays an important role in cancer cell apoptosis would be a very promising therapeutic strategy for the design of new anti-cancer drugs.

Two important types of negative regulatory factor s of cell apoptosis have been identified so far. The first class of the regulatory factors are Bcl-2 family proteins, such as two potent anti-apoptotic molecules, i.e., Bcl-2 and Bcl-XL proteins.

The second important class of the negative regulatory factors of cell apoptosis are inhibitors of apoptosis proteins (IAPB). IAPB were first discovered in baculoviruses due to their ability to replace the function of P35 protein. Such proteins include XIAP, cIAP1, cIAP2, ML-IAP, ILP-2, NAIP, Apollon, and Survivin. Among them, the X chromosome-linked inhibitor of apoptosis protein (XIAP) exerts an anti-apoptotic effect by directly inhibiting caspase-3, caspase-7 and caspase-9. cIAPs inhibit apoptosis mainly by blocking the death receptor pathway. With the degradation of cIAPs, the substrate thereof, i.e. NIK (NF-κB-inducing kinase) is prevented from being degraded and therefore accumulates. The accumulated NIK activates NF-κB via the non-canonical pathway, and the activation of NF-κB promotes the secretion of TNFα, which combines with TNF-R1 (TNF receptor-1) to trigger the death receptor pathway. The degradation of cIAPs also leads to increased secretion of RIPK1 (receptor interacting protein kinase 1), which, together with FADD (Fas-associated death domain) and caspase-8, forms a pro-apoptotic RIPK1-FADD-caspase-8 complex, and then caspase-3 is activated, thus leading to cell apoptosis.

Over-expression of cIAP1 and cIAP2 caused by frequent chromosome amplification of the 11q21 to q23 region (which covers both genes) has been observed in a variety of malignant diseases including neuroblastoma, renal cell carcinoma, colorectal carcinoma, gastric carcinoma, etc.

At present, many drug molecules have entered the clinical research and achieved positive progression, such as LCL-161, Debio 1143, BI-891065, and ASTX-660.

SUMMARY

The present disclosure provides a compound represented by formula (I) or a pharmaceutically acceptable salt thereof,

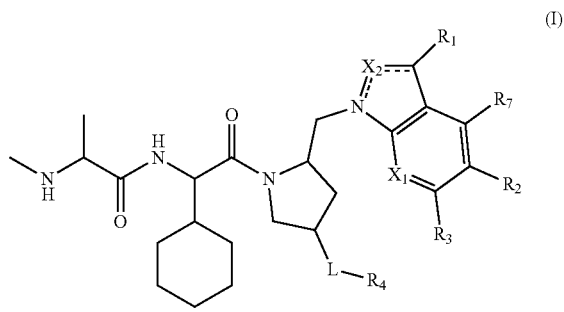

wherein, $X_1$ is selected from $C(R_5)$ and N;

$X_2$ is selected from $C(R_6)$, N, O, and S;

⚡ are each independently selected from a single bond and a double bond;

L is selected from a single bond and —O—;

$R_1$ is selected from —C(=O)NH$_2$, CN, $C_{1-5}$ alkyl, $C_{1-5}$ heteroalkyl, phenyl, 5- to 6-membered heteroaryl, and 5- to 6-membered heterocycloalkyl; said $C_{1-5}$ alkyl, $C_{1-5}$ heteroalkyl, phenyl, 5- to 6-membered heteroaryl or 5- to 6-membered heterocycloalkyl is optionally substituted with 1, 2 or 3 R;

$R_2$ is selected from H, halogen, CN, COOH, —C(=O)NH$_2$, $C_{1-4}$ alkyl, and $C_{1-4}$ heteroalkyl; said $C_{1-4}$ alkyl or $C_{1-4}$ heteroalkyl is optionally substituted with 1, 2 or 3 R;

$R_3$ and $R_7$ are each independently selected from H, halogen and $C_{1-4}$ alkyl; said $C_{1-4}$ alkyl is optionally substituted with 1, 2 or 3 R;

$R_4$ is selected from H, phenyl, and 5- to 6-membered heteroaryl;

$R_5$ is selected from H and halogen;

$R_6$ is selected from H, halogen, $C_{1-4}$ alkyl, $C_{1-4}$ heteroalkyl, CN, and COOH; said $C_{1-4}$ alkyl or $C_{1-4}$ heteroalkyl is optionally substituted with 1, 2 or 3 R;

R is selected from halogen, OH, CN, CH$_3$, CH$_3$CH$_2$, CH$_3$CH$_2$CH$_2$, CH(CH$_3$)$_2$, OCH$_3$, OCF$_3$, CHF$_2$, CH$_2$F, and NH$_2$; and said $C_{1-4}$ heteroalkyl, $C_{1-5}$ heteroalkyl, 5- to 6-membered heterocycloalkyl and 5- to 6-membered heteroaryl each contain 1, 2 or 3 heteroatoms or heteroatom radicals independently selected from —NH—, —O—, —S—, N, —C(=O)O—, —C(=O)—, —C(=O)NH—, —C(=S)—, —S(=O)—, —S(=O)$_2$—, —C(=NH)—, —S(=O)$_2$NH—, —S(=O)NH—, and —NHC(=O)NH—.

In some embodiments of the present disclosure, the above compound or a pharmaceutically acceptable salt thereof is selected from

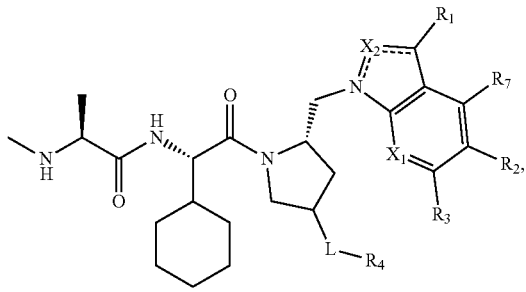

(I')

wherein ⫽, X$_1$, X$_2$, L, R$_1$, R$_2$, R$_3$, R$_4$ and R$_7$ are as defined above.

In some embodiments of the present disclosure, the above X$_2$ is selected from C(R$_6$) and N.

In some embodiments of the present disclosure, the above X$_2$ is selected from C(H), C(Cl), C(CH$_3$), and N.

In some embodiments of the present disclosure, the above R$_1$ is selected from —C(=O)NH$_2$, CN, C$_{1-5}$ alkyl, C$_{1-5}$ alkoxy, C$_{1-5}$ alkylamino, C$_{1-5}$ alkylthio, C$_{1-5}$ acyl, C$_{1-5}$ sulfonyl, phenyl, 5- to 6-membered heterocycloalkyl that contains 1 to 2 atoms independently selected from N or O and is optionally substituted with one oxo, and 5- to 6-membered heteroaryl containing 1 to 2 atoms independently selected from N; said C$_{1-5}$ alkyl, C$_{1-5}$ alkoxy, C$_{1-5}$ alkylamino, C$_{1-5}$ alkylthio, C$_{1-5}$ acyl, C$_{1-5}$ sulfonyl, phenyl, 5- to 6-membered heterocycloalkyl or 5- to 6-membered heteroaryl is optionally substituted with 1, 2 or 3 R.

In some embodiments of the present disclosure, the above R$_1$ is selected from —C(=O)NH$_2$, CN, CH$_3$, CH$_3$CH$_2$, C$_{1-5}$ alkyl-C(=O)—, C$_{1-4}$ alkyl-C(=O)—, C$_{1-5}$ alkyl-S(=O)$_2$—, C$_{1-5}$ alkyl-N(H)C(=O)—, C$_{1-4}$ alkyl-N(H)C(=O)—, (C$_{1-2}$ alkyl)$_2$-N—C(=O)—, phenyl,

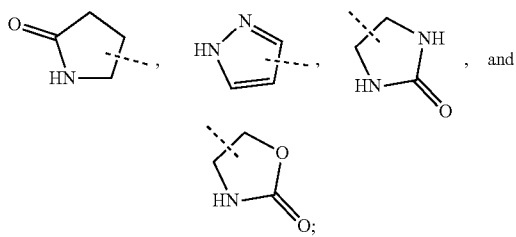

said CH$_3$, CH$_3$CH$_2$, C$_{1-5}$ alkyl-C(=O)—, C$_{1-4}$ alkyl-C(=O)—, C$_{1-5}$ alkyl-S(=O)$_2$—, C$_{1-5}$ alkyl-N(H)C(=O)—, C$_{1-4}$ alkyl-N(H)C(=O)—, (C$_{1-2}$ alkyl)$_2$-N—C(=O)—, phenyl,

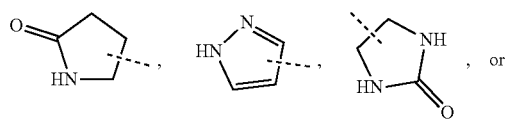, or

-continued

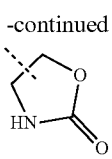

is optionally substituted with 1, 2 or 3 R.

In some embodiments of the present disclosure, the above R$_1$ is selected from

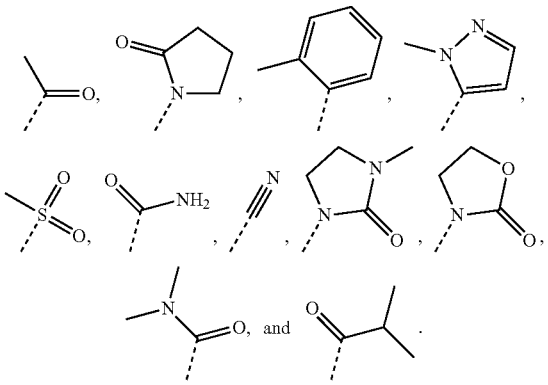

In some embodiments of the present disclosure, the above R$_2$ is selected from H, halogen, C$_{1-4}$ alkyl, and C$_{1-4}$ alkyl-O—; said C$_{1-4}$ alkyl or C$_{1-4}$ alkyl-O— is optionally substituted with 1, 2 or 3 halogens.

In some embodiments of the present disclosure, the above R$_2$ is selected from H, F, Cl, Br, CF$_3$, and OCF$_3$.

In some embodiments of the present disclosure, the above R$_3$ and R$_7$ are each independently selected from H, F and Cl.

In some embodiments of the present disclosure, the above R$_4$ is selected from H and

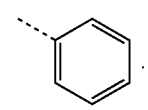.

In some embodiments of the present disclosure, the above R$_5$ is selected from H and Cl.

In some embodiments of the present disclosure, the above R$_6$ is selected from H, Cl and CH$_3$.

In some embodiments of the present disclosure, the above structural unit

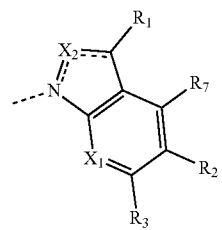

is selected from
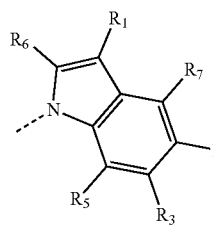 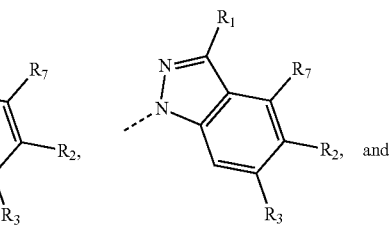
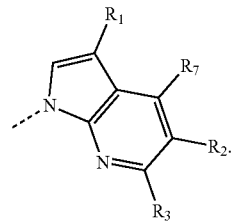
In some embodiments of the present disclosure, the above structural unit
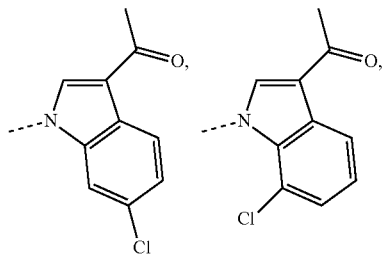
is selected from
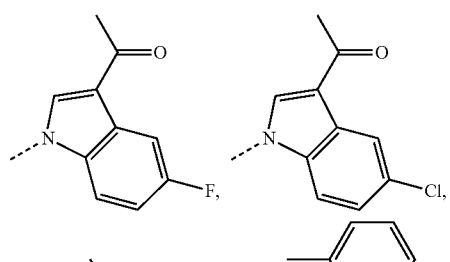
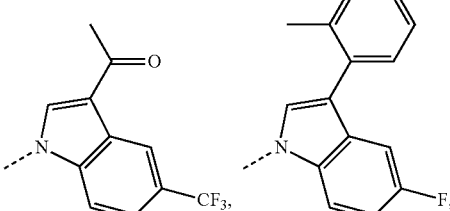
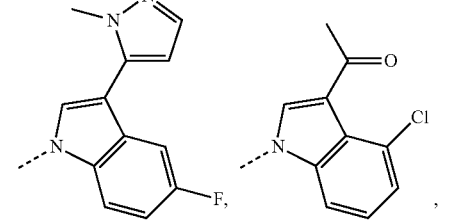
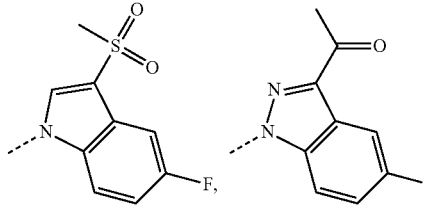
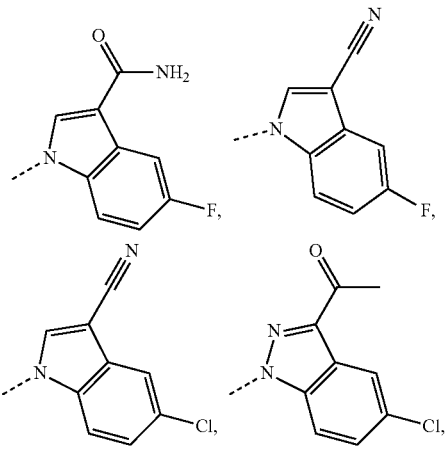
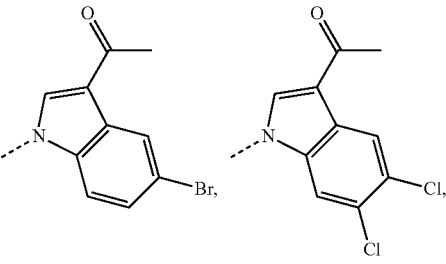
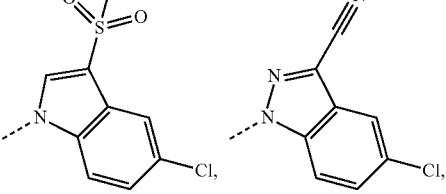
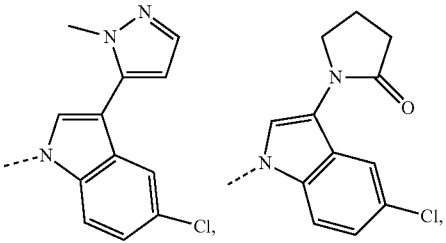

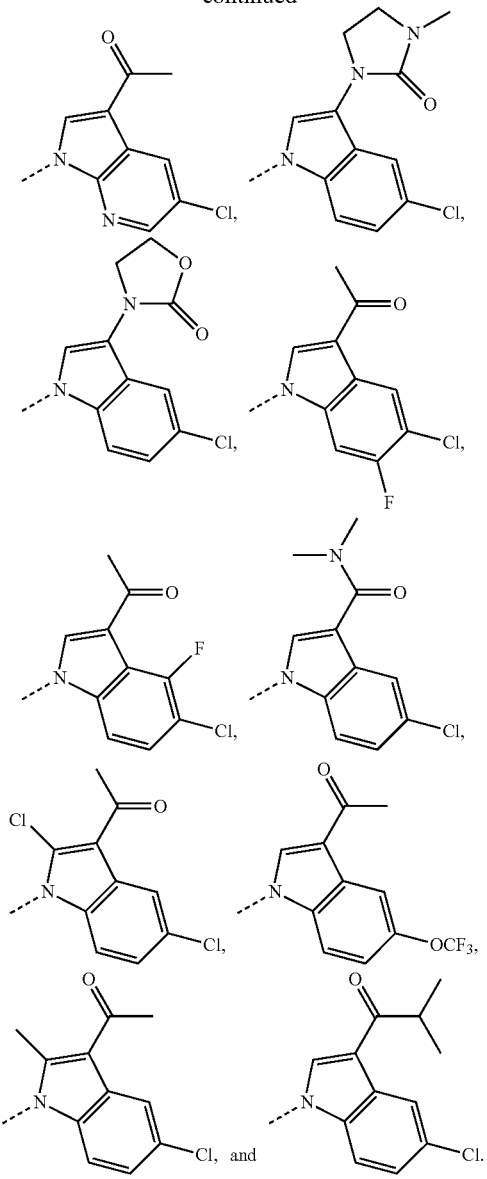

alkyl-C(=O)—, C$_{1-4}$ alkyl-C(=O)—, C$_{1-5}$ alkyl-S(=O)$_2$—, C$_{1-5}$ alkyl-N(H)C(=O)—, C$_{1-4}$ alkyl-N(H)C(=O)—, (C$_{1-2}$ alkyl)$_2$-N—C(=O)—, phenyl,

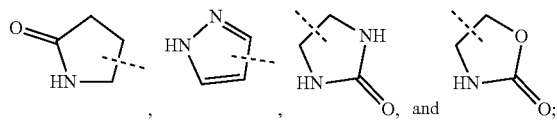

, , , and ;

said CH$_3$, CH$_3$CH$_2$, C$_{1-5}$ alkyl-C(=O)—, C$_{1-4}$ alkyl-C(=O)—, C$_{1-5}$ alkyl-S(=O)$_2$—, C$_{1-5}$ alkyl-N(H)C(=O)—, C$_{1-4}$ alkyl-N(H)C(=O)—, (C$_{1-2}$ alkyl)$_2$-N—C(=O)—, phenyl,

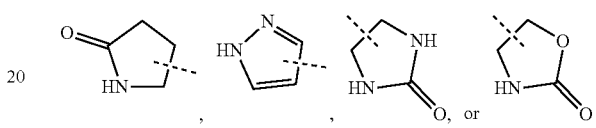

, , , or is optionally substituted with 1, 2 or 3 R, and other variables are as defined above.

In some embodiments of the present disclosure, the above R$_2$ is selected from H, halogen, C$_{1-4}$ alkyl, and C$_{1-4}$ alkyl-O—; said C$_{1-4}$ alkyl or C$_{1-4}$ alkyl-O— is optionally substituted with 1, 2 or 3 halogens, and other variables are as defined above.

In some embodiments of the present disclosure, the above R$_2$ is selected from H, F, Cl, Br, CF$_3$, and OCF$_3$, and other variables are as defined above.

In some embodiments of the present disclosure, the above R$_3$ and R$_7$ are each independently selected from H, F and Cl, and other variables are as defined above.

In some embodiments of the present disclosure, the above R$_4$ is selected from H and

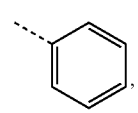

, and other variables are as defined above.

In some embodiments of the present disclosure, the above R$_5$ is selected from H and Cl, and other variables are as defined above.

In some embodiments of the present disclosure, the above R$_6$ is selected from H, Cl and CH$_3$, and other variables are as defined above.

In some embodiments of the present disclosure, the above structural unit

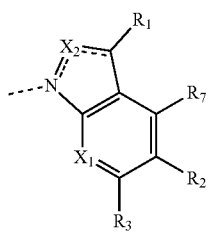

In some embodiments of the present disclosure, the above X$_2$ is selected from C(R$_6$) and N, and other variables are as defined above.

In some embodiments of the present disclosure, the above X$_2$ is selected from C(H), C(Cl), C(CH$_3$), and N, and other variables are as defined above.

In some embodiments of the present disclosure, the above R$_1$ is selected from —C(=O)NH$_2$, CN, C$_{1-5}$ alkyl, C$_{1-5}$ alkoxy, C$_{1-5}$ alkylamino, C$_{1-5}$ alkylthio, C$_{1-5}$ acyl, C$_{1-5}$ sulfonyl, phenyl, 5- to 6-membered heterocycloalkyl that contains 1 to 2 atoms independently selected from N or O and is optionally substituted with one oxo, and 5- to 6-membered heteroaryl containing 1 to 2 atoms independently selected from N; said C$_{1-5}$ alkyl, C$_{1-5}$ alkoxy, C$_{1-5}$ alkylamino, C$_{1-5}$ alkylthio, C$_{1-5}$ acyl, C$_{1-5}$ sulfonyl, phenyl, 5- to 6-membered heterocycloalkyl or 5- to 6-membered heteroaryl is optionally substituted with 1, 2 or 3 R, and other variables are as defined above.

In some embodiments of the present disclosure, the above R$_1$ is selected from —C(=O)NH$_2$, CN, CH$_3$, CH$_3$CH$_2$, C$_{1-5}$ is selected from
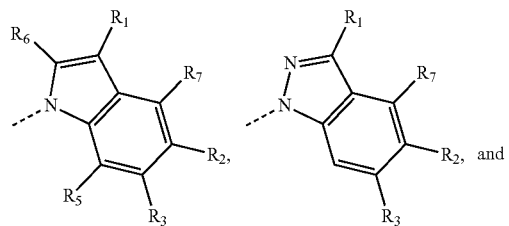
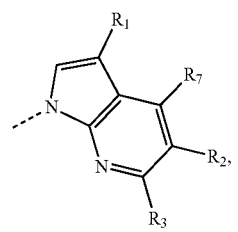
and other variables are as defined above.
In some embodiments of the present disclosure, the above structural unit
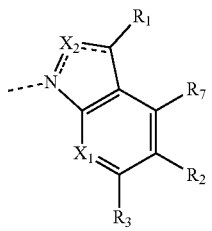
is selected from
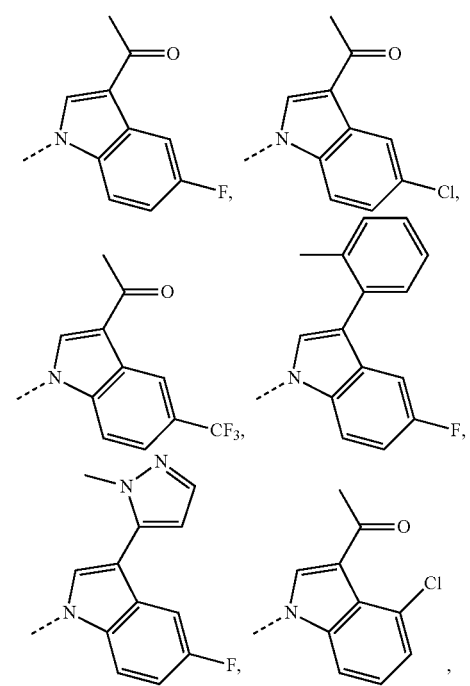
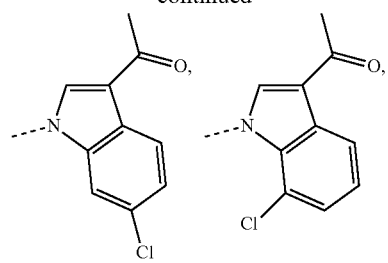
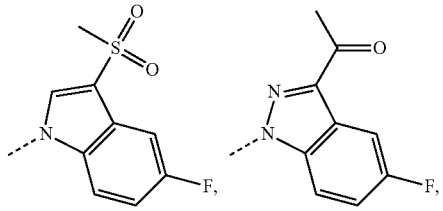
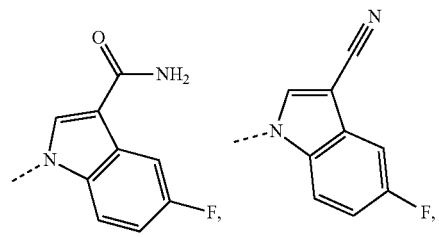
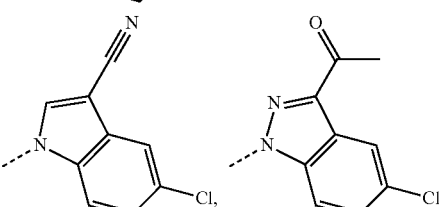
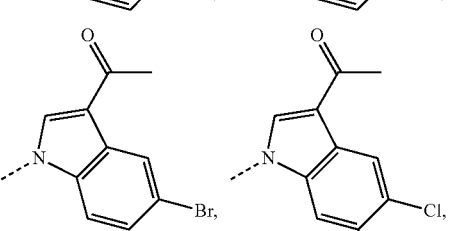
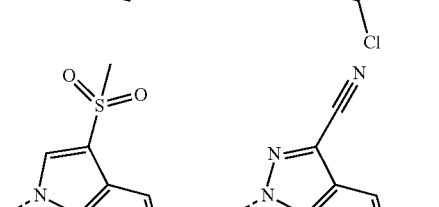
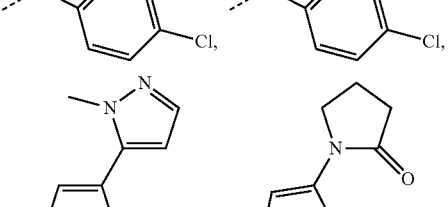
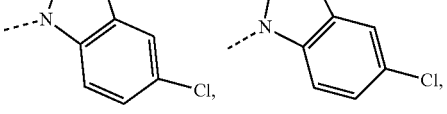

-continued

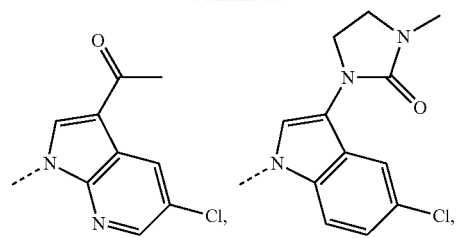

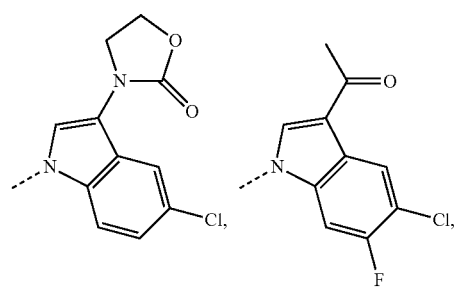

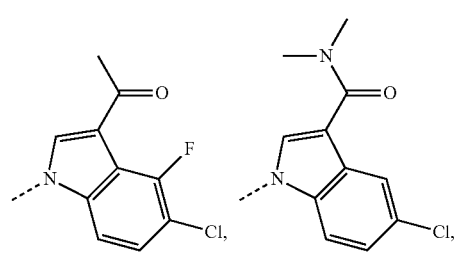

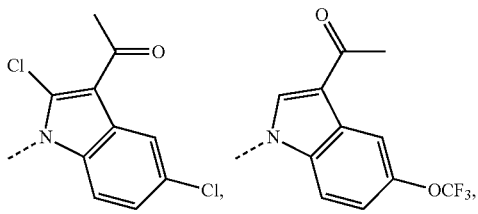

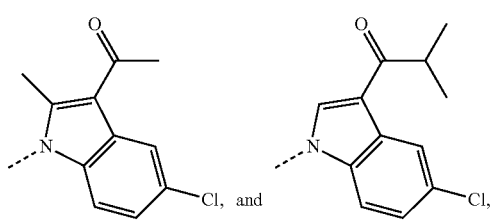

and other variables are as defined above.

There are also some embodiments of the present disclosure that are derived from any combination of the above variables.

In some embodiments of the present disclosure, the above compound or a pharmaceutically acceptable salt thereof is selected from

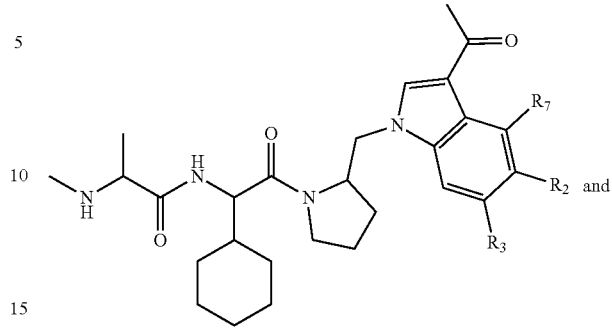

(II)

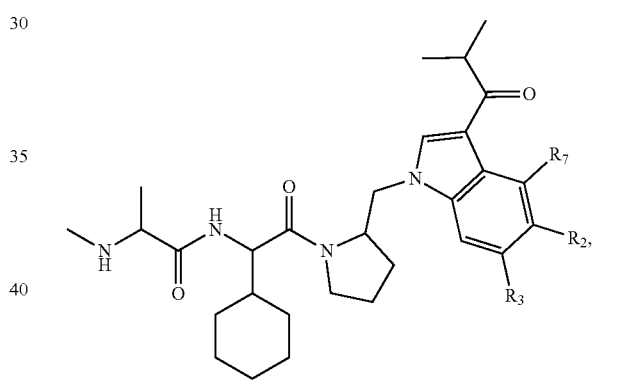

(III)

wherein $R_2$, $R_3$ and $R_7$ are as defined above.

In some embodiments of the present disclosure, the above compound or a pharmaceutically acceptable salt thereof is selected from

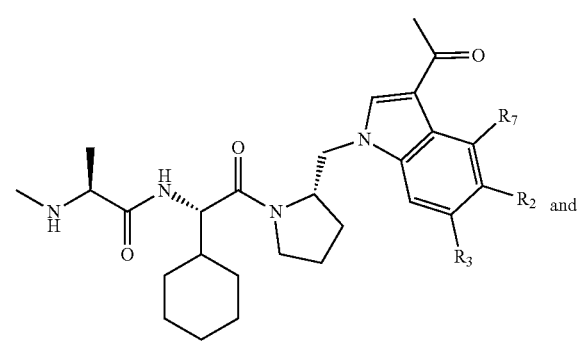

(II')

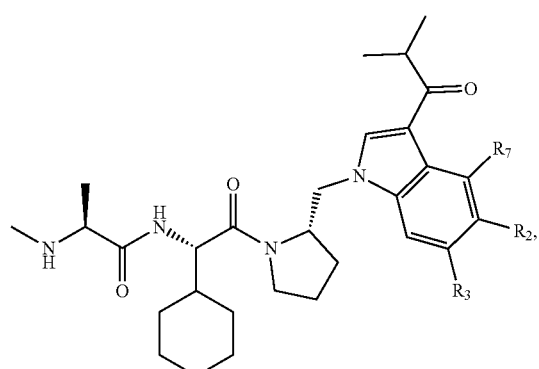
wherein R₂, R₃ and R₇ are as defined above.
The present disclosure further provides a compound or a pharmaceutically acceptable salt thereof, which is selected from
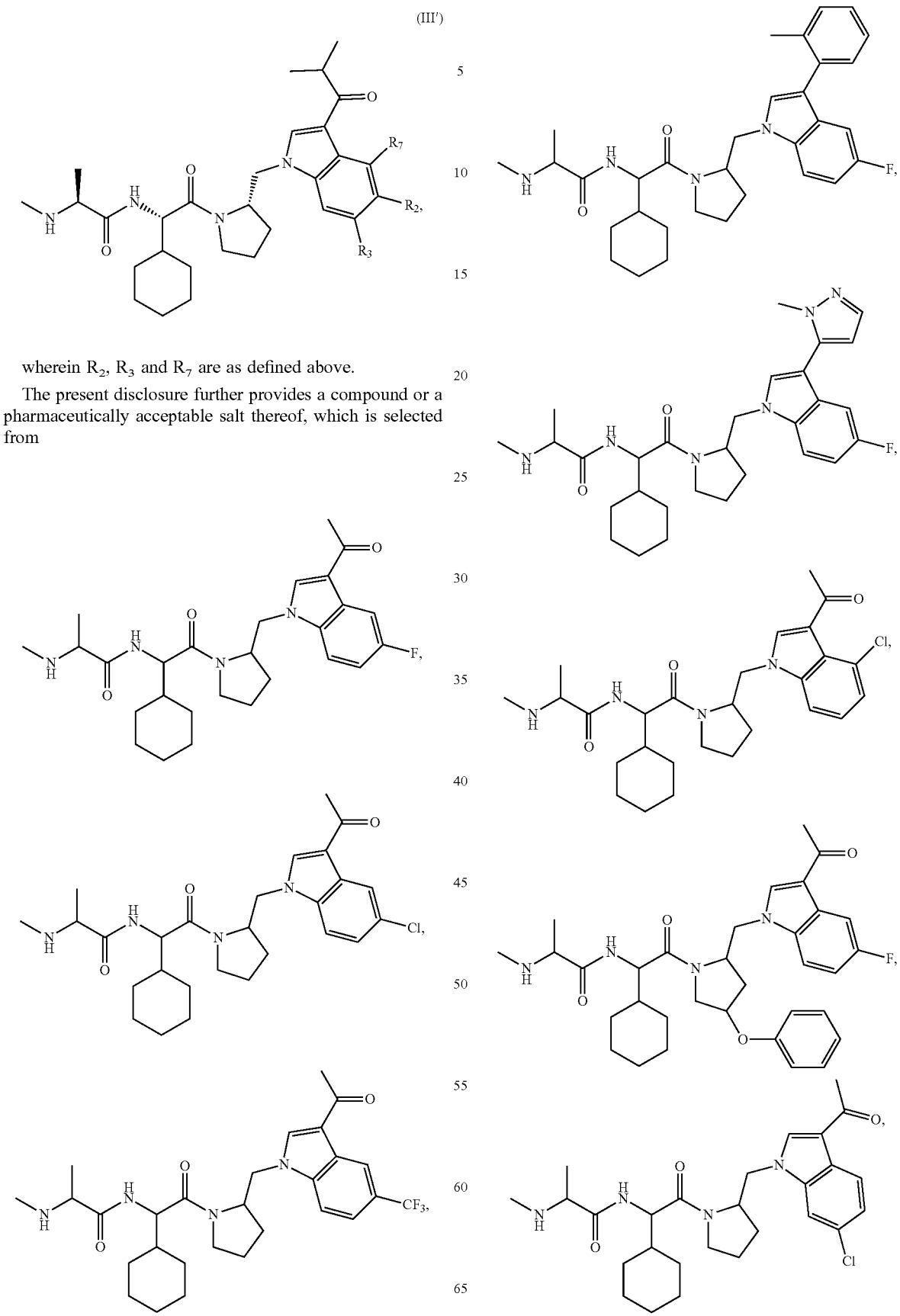

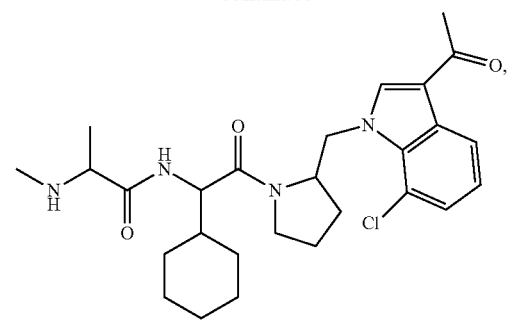
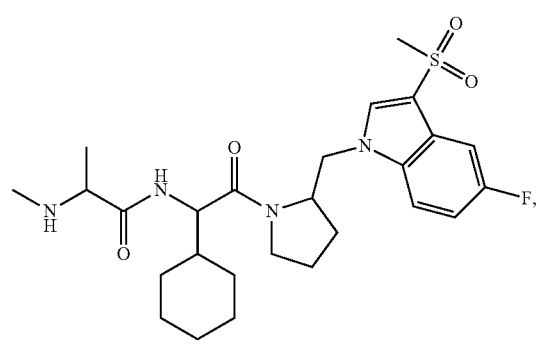
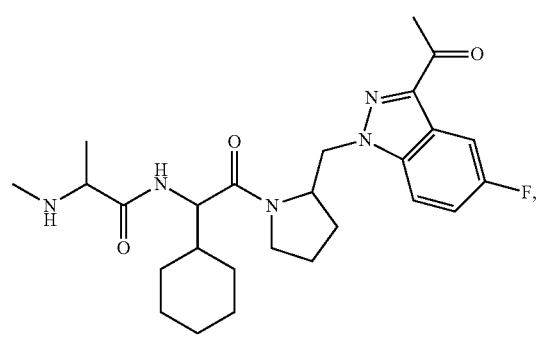
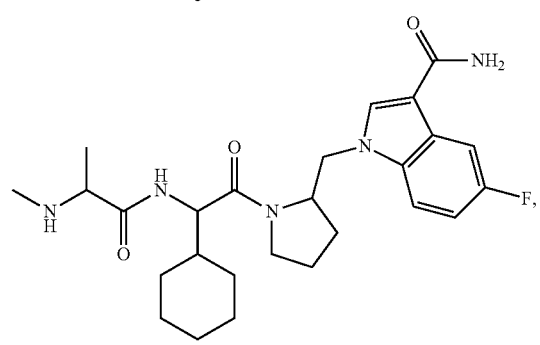
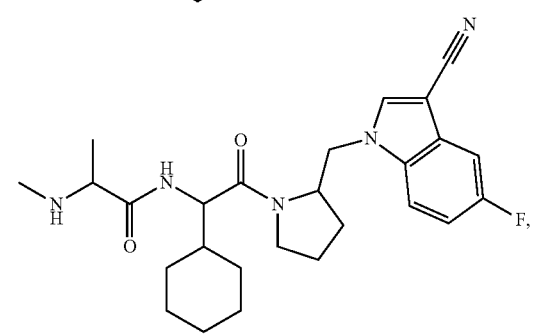
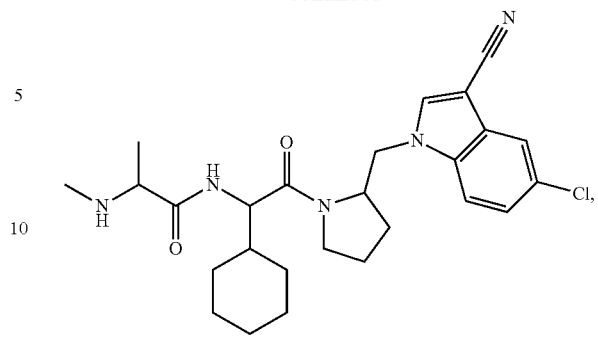
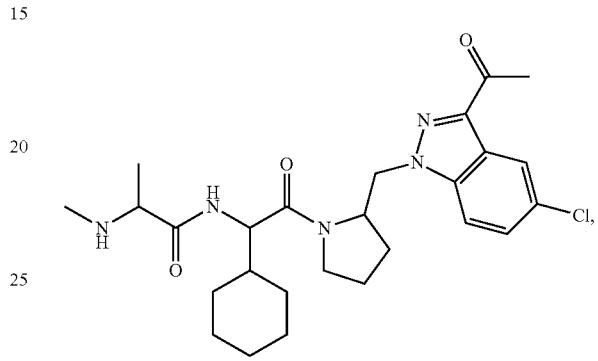
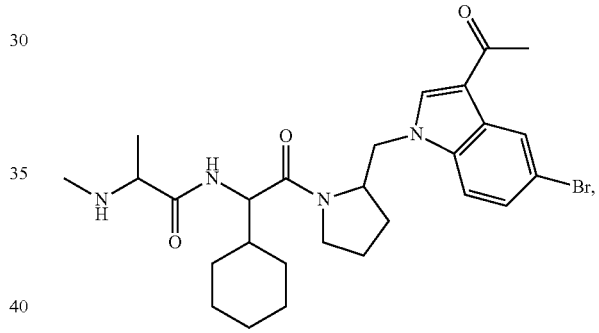
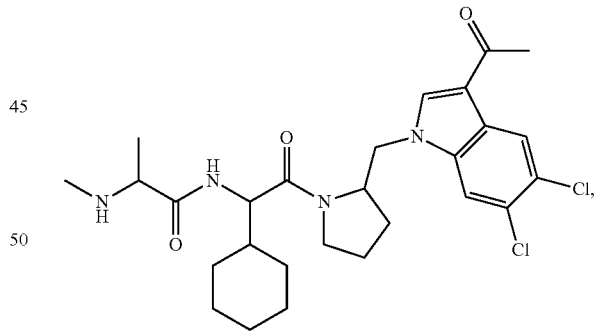
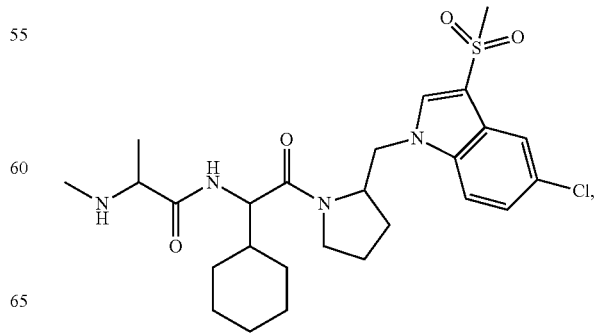

-continued
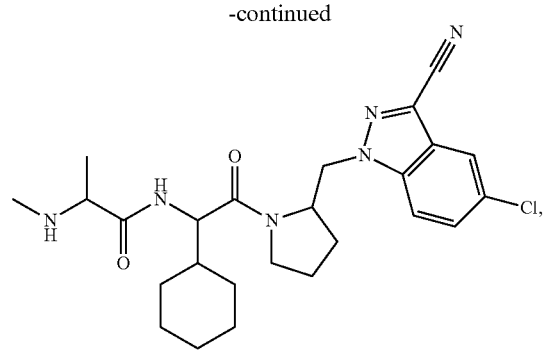
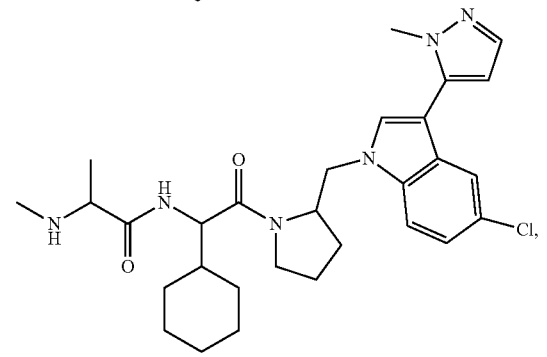
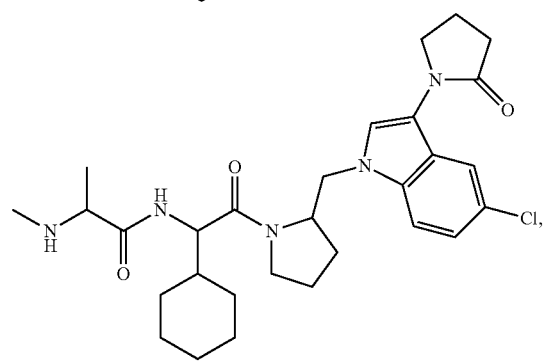
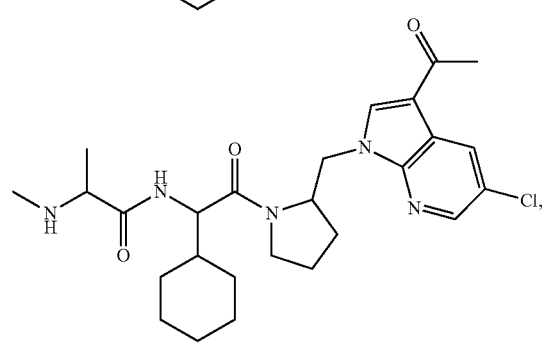
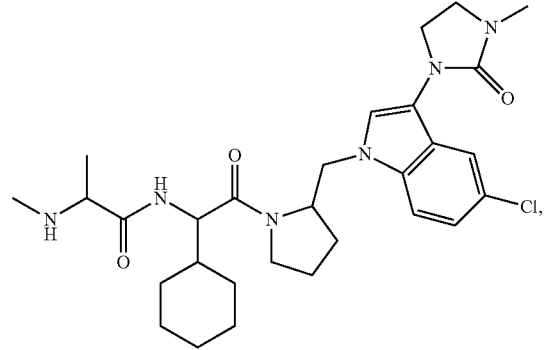
-continued
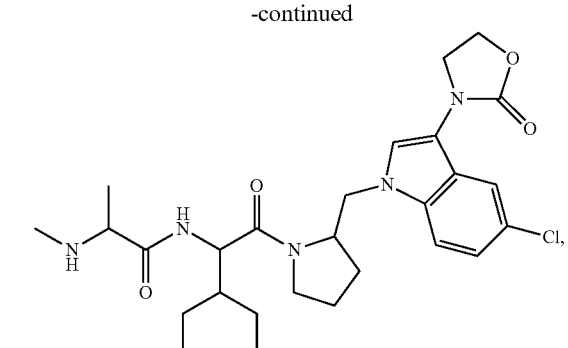
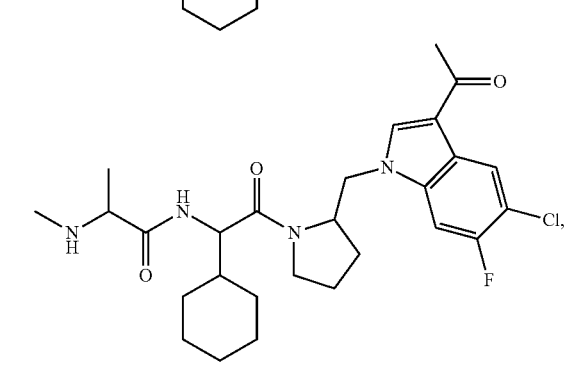
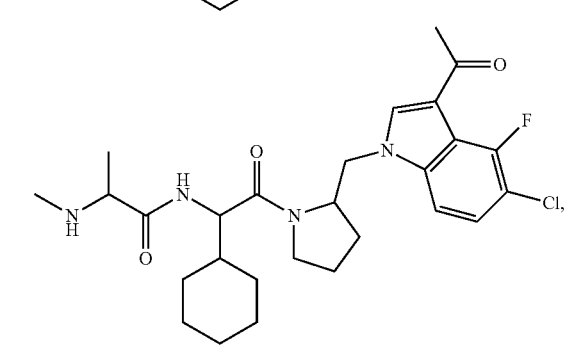
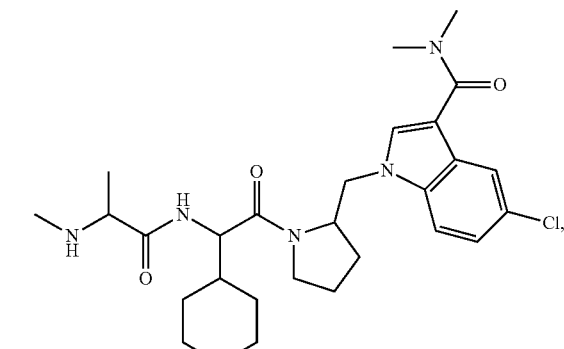
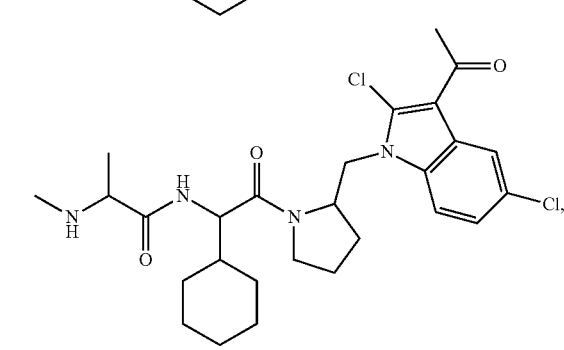

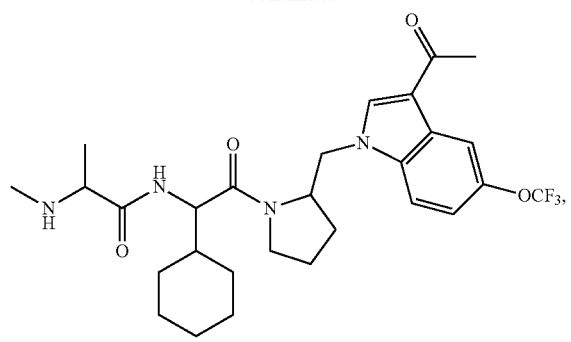
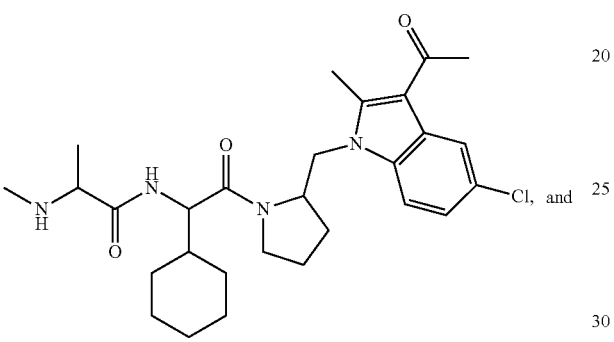
In some embodiments of the present disclosure, the above compound or a pharmaceutically acceptable salt thereof is selected from
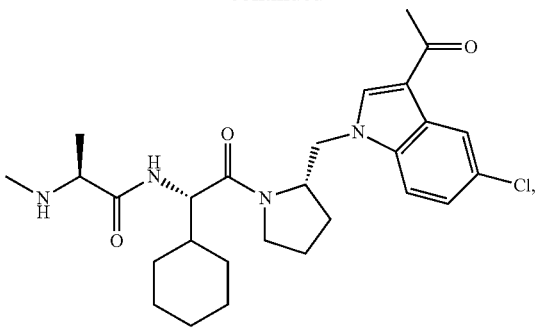
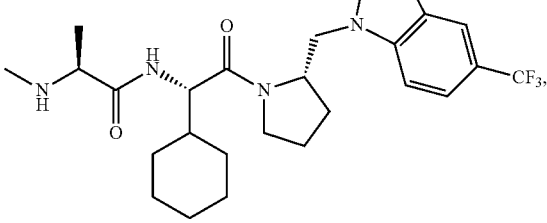

21
-continued
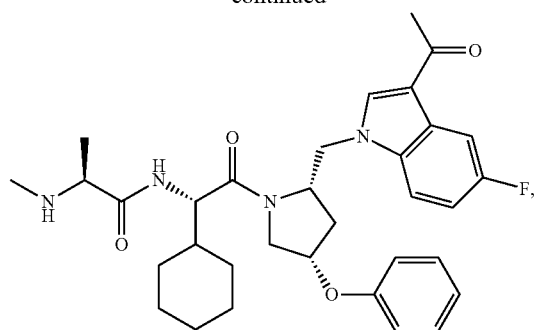
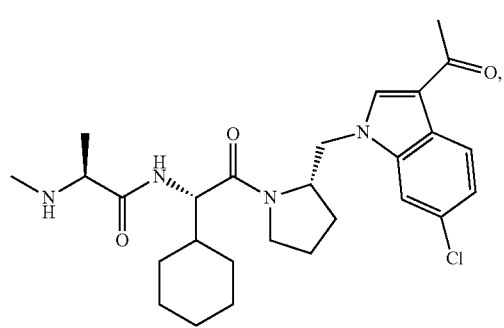
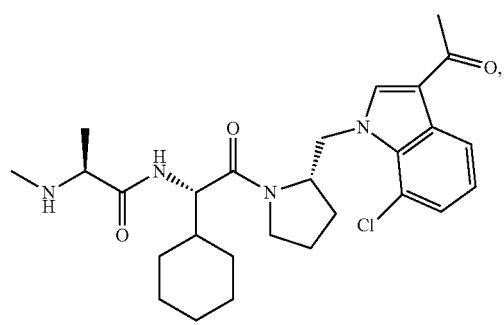
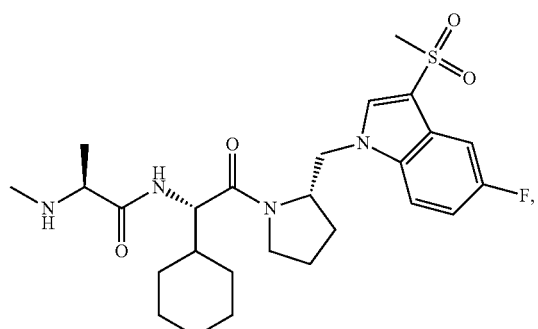
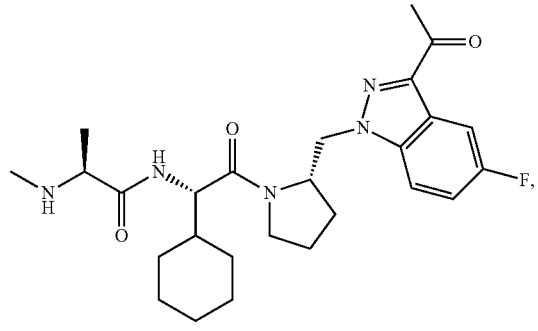
22
-continued
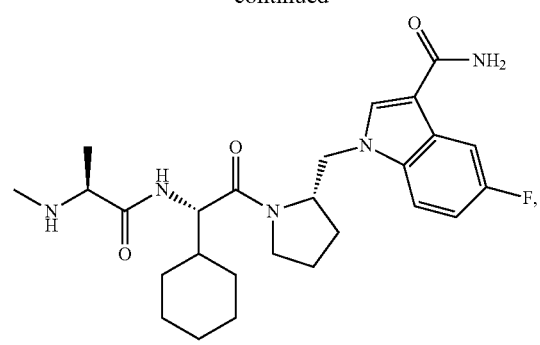
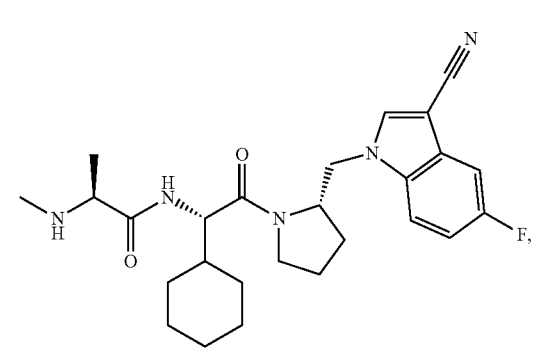
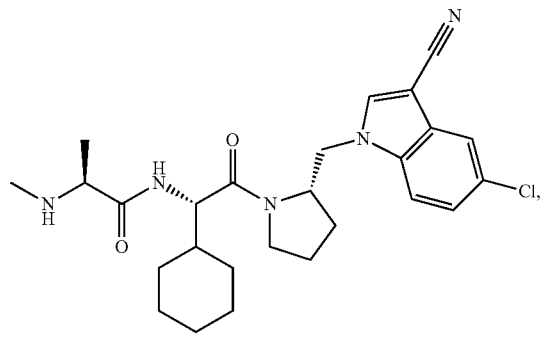
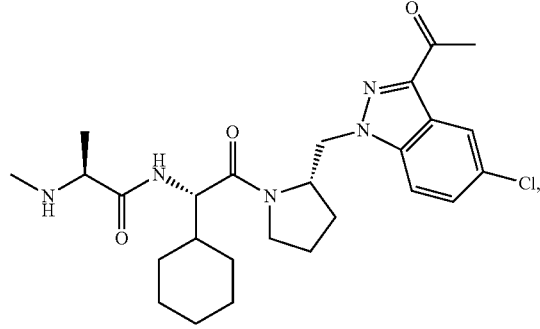
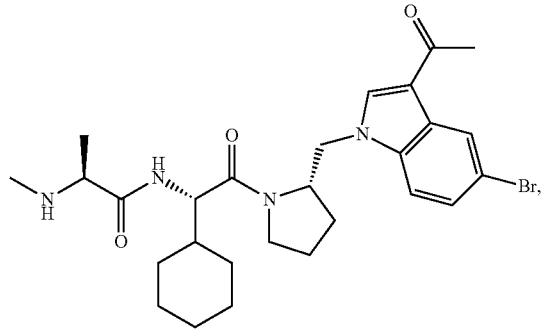

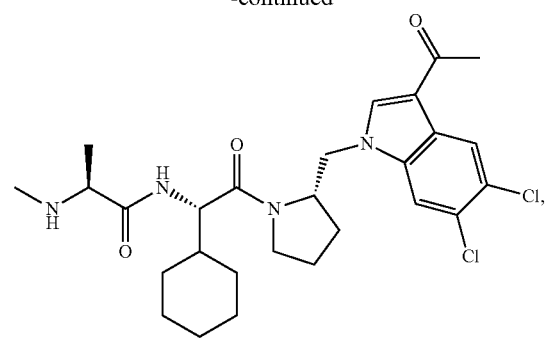
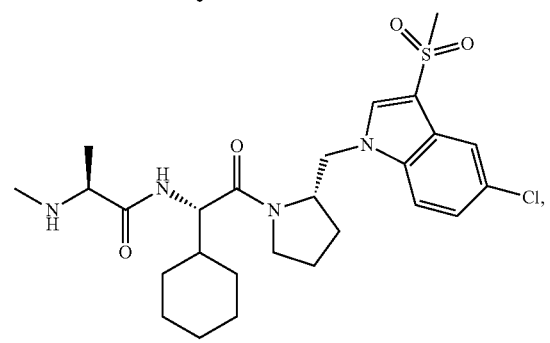
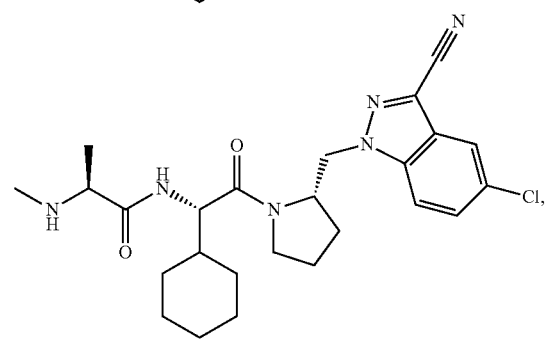
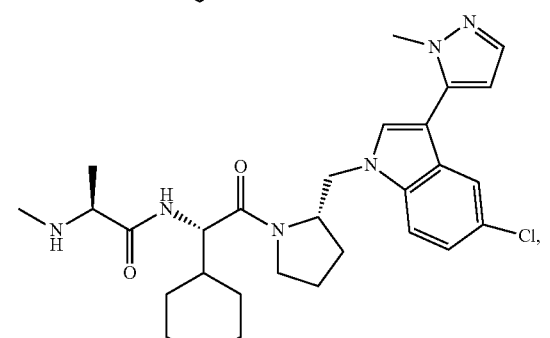
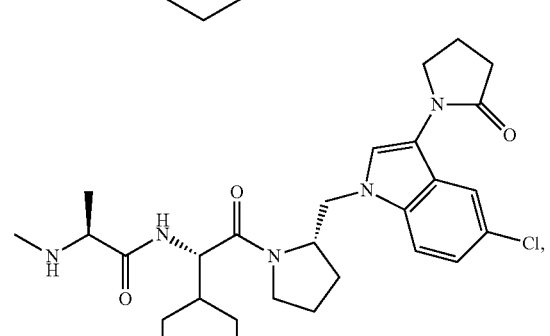
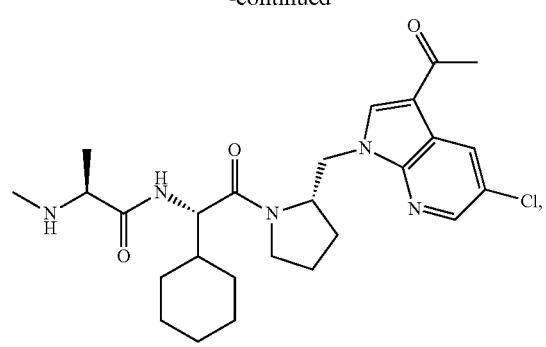
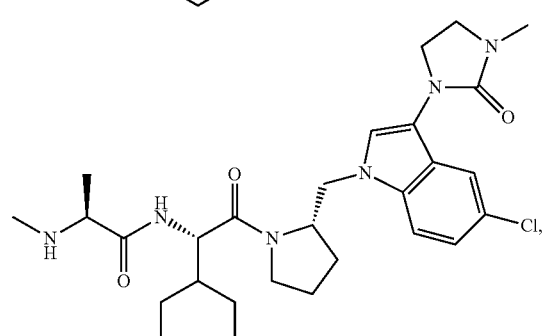
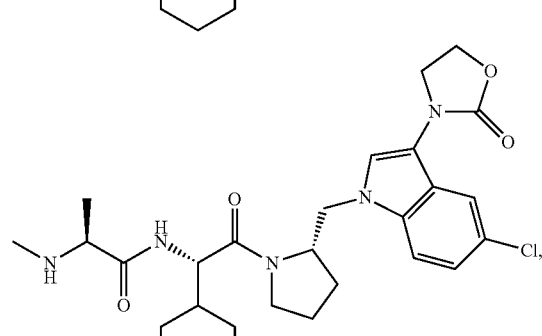
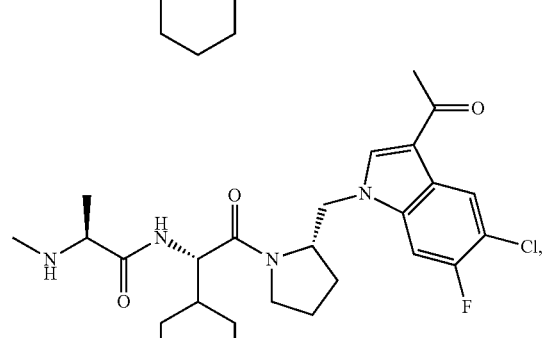
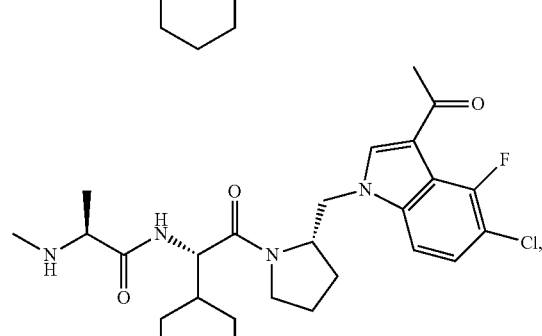

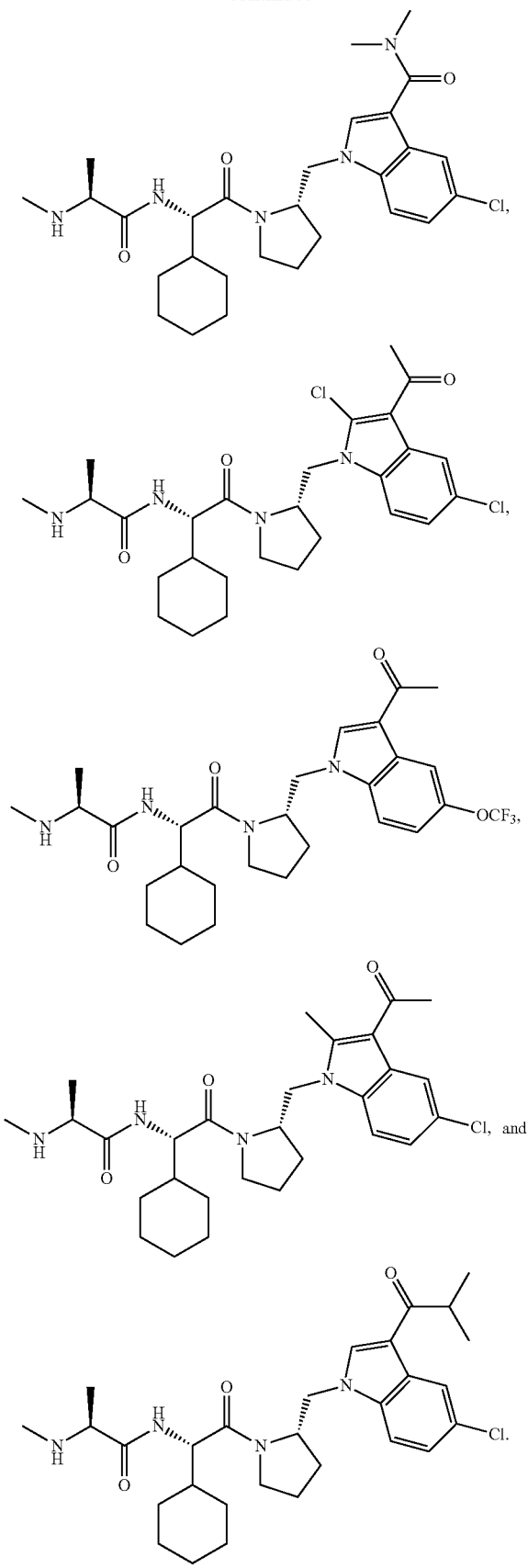

The present disclosure further provides a pharmaceutical composition, comprising a therapeutically effective amount of the above compound or a pharmaceutically acceptable salt thereof as an active ingredient, and a pharmaceutically acceptable carrier.

The present disclosure further provides use of the above compound or a pharmaceutically acceptable salt thereof, or the above pharmaceutical composition in the preparation of an IAP inhibitor.

In another aspect, the present disclosure further provides a method for treating a disease that benefits from IAP inhibition, comprising administering a therapeutically effective amount of the above compound or a pharmaceutically acceptable salt thereof, and the above pharmaceutical composition to a mammal in need of such treatment, preferably a human.

In another aspect, the present disclosure further provides use of the above compound or a pharmaceutically acceptable salt thereof, and the above pharmaceutical composition in the treatment of a disease that benefits from IAP inhibition.

In another aspect, the present disclosure further provides the above compound or a pharmaceutically acceptable salt thereof for use as a drug. In some embodiments of the present disclosure, the wording "for use as a drug" mentioned above refers to being used as a drug for treating a disease that benefits from IAP inhibition.

In some embodiments of the present disclosure, the above IAP inhibitor refers to a cIAP1 inhibitor.

In some embodiments of the present disclosure, the above IAP inhibitor or cIAP1 inhibitor is a drug for treating cancer.

In some embodiments of the present disclosure, the above cancer is breast cancer.

TECHNICAL EFFECTS

The compound of the present disclosure is a SMAC mimetic, which has an antagonistic effect on cIAP1 and is selective for cIAP1 and XIAP.

Definitions and Description

Unless otherwise specified, the following terms and phrases used herein are intended to have the following meanings. A specific term or phrase, if not particularly defined, should not be considered as uncertain or ambiguous, but should be understood as its ordinary meaning. When a trade name appears herein, it is intended to refer to the corresponding commodity thereof or an active ingredient thereof. The term "pharmaceutically acceptable" used herein is intended to refer to those compounds, materials, compositions and/or dosage forms which, within the scope of reliable medical judgment, are suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of a compound of the present disclosure, which is prepared from a compound having particular substituent(s) as found by the present disclosure and a relatively non-toxic acid or base. When a compound of the present disclosure contains a relatively acidic functional group, a base addition salt may be obtained by contacting the neutral form of such compound with a sufficient amount of a base in a pure solution or a suitable inert solvent. When a compound of the present disclosure contains a relatively basic functional group, an acid addition salt may be obtained by contacting the neutral form of such compound with a sufficient amount of an acid in a pure solution or a suitable inert solvent. Examples of pharmaceutically acceptable acid addition salts include inorganic acid salts. Certain specific compounds of the present disclosure contain basic and acidic functional groups and thus may be converted to any of base addition salts or acid addition salts.

The pharmaceutically acceptable salts of the present disclosure may be synthesized from the parent compounds containing acid radicals or basic radicals by conventional chemical methods. Generally, such salts are prepared by the following method: reacting these compounds in the form of free acid or base with a stoichiometric amount of an appropriate base or acid in water or an organic solvent or a mixture of both.

The compounds of the present disclosure may have specific geometric isomeric form or stereoisomeric form. The present disclosure contemplates all such compounds, including cis- and trans-isomers, (−)- and (+)-enantiomers, (R)- and (S)-enantiomers, diastereomers, (D)-isomers, (L)-isomers, as well as the racemic mixtures and other mixtures thereof, such as enantiomerically or diastereomerically enriched mixtures, and all these mixtures fall within the scope of the present disclosure. Additional asymmetric carbon atom(s) may be present in the substituent(s) such as alkyl. All these isomers and the mixtures thereof are included in the scope of the present disclosure.

Unless otherwise specified, the term "enantiomer" or "optical isomer" refers to either of a pair of stereoisomers that are the mirror images of each other.

Unless otherwise specified, the term "cis-trans isomer" or "geometric isomer" refers to an isomer resulting from the fact that the double bond or the single bond between ring-forming carbon atoms cannot rotate freely.

Unless otherwise specified, the term "diastereomer" refers to either of a pair of stereoisomers, of which the molecule has two or more chiral centers and which has a non-mirror-image relationship with the other stereoisomer of the molecule.

Unless otherwise specified, "(+)" means right-handed, "(−)" means left-handed, and "(±)" means racemic.

Unless otherwise specified, the wedge-shaped solid-line bond ( ) and the wedge-shaped dashed-line bond ( ) are used to represent the absolute configuration of a stereogenic center, and the straight solid-line bond ( ) and the straight dashed-line bond ( ) are used to represent the relative configuration of a stereogenic center. The wavy line ( ) is used to represent a wedge-shaped solid-line bond ( ) or a wedge-shaped dashed-line bond ( ), or the wavy line ( ) is used to represent a straight solid-line bond ( ) and a straight dashed-line bond ( ).

The compounds of the present disclosure may have specific tautomeric forms. Unless otherwise specified, the term "tautomer" or "tautomeric form" refers to each of two or more isomers in which different isomeric forms of a functional group are in dynamic equilibrium and may readily convert to each other at room temperature. If tautomers possibly exist (for example, exist in a solution), a chemical equilibrium between the tautomers may be achieved. For example, proton tautomers (also referred to as prototropic tautomers) involve interconversions via proton migration, such as keto-enol isomerization and imine-enamine isomerization. Valence tautomers involve interconversions via recombination of some bonding electrons. Among them, a specific example of keto-enol tautomerization is the interconversion between the following two tautomers: pentane-2,4-dione and 4-hydroxypent-3-en-2-one.

Unless otherwise specified, when a compound of the present disclosure has isomers, there are cases where the compound is "enriched in one isomer", "isomerically enriched", "enriched in one enantiomer" or "enantiomerically enriched". Said terms "enriched in one isomer", "isomerically enriched", "enriched in one enantiomer" or "enantiomerically enriched" mean that the content of one of the isomers or enantiomers is less than 100%, and the content of this isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, when a compound of the present disclosure has isomers, there are cases of "isomeric excess" or "enantiomeric excess". Said term "isomeric excess" or "enantiomeric excess" refers to the difference between the relative percentages of two isomers or two enantiomers. For example, if the content of one isomer or enantiomer is 90% and the content of the other isomer or enantiomer is 10%, then the isomeric or enantiomeric excess (ee value) is 80%.

The optically active (R)- and (9-isomers and D- and L-isomers may be prepared by chiral synthesis, or with chiral reagents, or by other conventional techniques. If an enantiomer of a certain compound of the present disclosure is desired, it may be prepared by asymmetric synthesis or derivatization that uses a chiral auxiliary, in which the resulting mixture of diastereomers is separated and the auxiliary group is cleaved to provide the desired pure enantiomer. Alternatively, when the molecule contains a basic functional group (such as amino) or an acidic functional group (such as carboxyl), a salt of the diastereomer is formed by the molecule and an appropriate optically active acid or base, then diastereomeric resolution is performed by conventional methods well known in the art, and the pure enantiomer is obtained by recovery. In addition, the separation between enantiomer and diastereomer is usually accomplished by using chromatography, which adopts a chiral stationary phase and is to optionally combined with a chemical derivatization method (for example, the formation of carbamate from amine). The compounds of the present disclosure may contain an atomic isotope in an unnatural proportion at one or more atoms constituting such compounds. For example, the compounds may be labeled with a radioisotope, such as tritium ($^3$H), iodine-125 ($^{125}$I) or C-14 ($^{14}$C). For another example, hydrogen may be substituted with heavy hydrogen to form a deuterated drug. The bond formed by deuterium and carbon is stronger than the bond formed by ordinary hydrogen and carbon. Compared with an undeuterated drug, a deuterated drug has advantages such as reduced toxicity and side effects, increased drug stability, strengthened efficacy, and prolonged biological half-life of drugs. All variations of the isotopic composition of the compounds of the present disclosure are included within the scope of the present disclosure regardless of the radioactivity. The term "pharmaceutically acceptable carrier" refers to any preparation or carrier medium capable of delivering an effective amount of the active substance of the present disclosure without interfering with the biological activity of the active substance, and exerts no toxic or side effects on the host or patient. Representative carriers include water, oils, vegetables and minerals, cream bases, lotion bases, ointment bases, etc. Such bases include suspending agents, tackifiers, penetration enhancers, and the like. Their preparations are well known to those skilled in the cosmetics field or the field of drugs for topical administration.

The term "excipient" generally refers to a carrier, a diluent and/or a medium required for the formulation of an effective pharmaceutical composition.

The wording "comprise" and the variants thereof, such as "comprises" or "comprising", should be understood as having an open and non-exclusive meaning, namely, "including but not limited to".

The term "treating" means administering a compound or a preparation described in the present application to prevent, ameliorate or eliminate a disease or one or more symptoms associated with the disease, and includes:

(i) preventing a disease or a disease state from occurring in a mammal, especially when such mammal is susceptible to the disease state but has not yet been diagnosed as having the disease state;

(ii) inhibiting a disease or a disease state, i.e. restraining its development; and (iii) alleviating a disease or a disease state, i.e. causing the regression of the disease or the disease state.

As for a drug or a pharmacologically active agent, the term "effective amount" or "therapeutically effective amount" refers to a sufficient amount of the drug or medicament that is not toxic but yet capable of achieving the intended effect. For the oral dosage form in the present disclosure, an "effective amount" of one active substance in a composition is the amount required to achieve the intended effect when used in combination with another active substance in the composition. The determination of an effective amount varies from person to person, depending on the age and the general condition of the subject as well as the specific active substance. An appropriate effective amount in a case may be determined by a person skilled in the art based on routine tests.

The term "active ingredient", "therapeutic agent", "active substance" or "active agent" refers to a chemical entity that may be effective in treating a target disorder, disease or condition.

"Optional" or "optionally" means that the event or situation described later may occur, but not necessarily, and such description includes a case where said event or situation occurs and a case where said event or situation does not occur.

The term "substituted" means that any one or more of the hydrogen atom(s) on a specific atom are replaced with a substituent, which may include heavy hydrogen or variants of hydrogen, as long as the valence state of the specific atom is normal and the substituted compound is stable. When the substituent is oxygen (i.e. =O), it means that two hydrogen atoms are substituted. Oxo does not occur on an aromatic group. The term "optionally substituted" means that it may or may not be substituted. Unless otherwise specified, the type and number of substituents may be arbitrary as long as the substitution is chemically feasible.

When any variable (such as R and ⌒) appears more than once in the composition or the structure of a compound, its definition in each case is independent. Thus, for example, if a group is substituted with 0 to 2 R, the group may optionally be substituted with up to two R, and there are independent options for R in each case. In addition, any combination of variables and/or variants thereof is allowed only in a case where such combination results in a stable compound.

When the number of a linking group is zero, such as —(CRR)$_0$—, it means that the linking group is a single bond.

When one of the variables is selected from a single bond, it means that the two groups linked by this variable are directly linked to each other. For example, when L in A-L-Z represents a single bond, the structure is actually A-Z.

When a substituent is absent, it means that the substituent does not exist. For example, when X in A-X is absent, it means that the structure is actually A. When a substituent may be linked to one or more atoms of a ring, such substituent may be bonded to any atom of the ring. For example, the structural unit

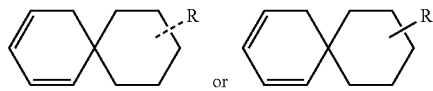

means a structural unit in which any position of cyclohexyl or cyclohexadiene may be substituted with the substituent R. When it is not specified that via which atom a listed substituent is linked to a substituted group, such substituent may be bonded via any atoms thereof. For example, pyridyl as a substituent may be linked to the substituted group via any carbon atom of the pyridine ring. When the linking direction of a listed linking group is not specified, the linking direction thereof is arbitrary. For example, when the linking group L in

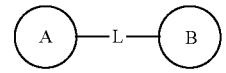

is -M-W-, the ring A and the ring B may be linked by -M-W- to either form

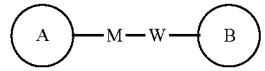

in the direction same as the left-to-right reading order, or form

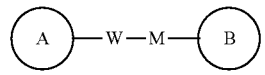

in the direction opposite to the left-to-right reading order. Combinations of said linking groups, substituents, and/or variants thereof are allowed only in a case where such combinations result in stable compounds.

Unless otherwise specified, the term "hetero" means a heteroatom or a heteroatom radical (i.e. a heteroatom-containing radical), including atoms other than carbon (C) and hydrogen (H), and radicals containing these heteroatoms, such as oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless otherwise specified, a "ring" means a substituted or unsubstituted cycloalkyl, heterocycloalkyl, cycloalkenyl, heterocycloalkenyl, cycloalkynyl, heterocycloalkynyl, aryl, or heteroaryl. The so-called "ring" includes a monocyclic ring, a bicyclic ring, a spiro ring, a fused ring, or a bridged ring. The number of atoms in a ring is usually defined as the number of ring members. For example, a "5- to 7-membered ring" means that 5 to 7 atoms are arranged around as a ring. Unless otherwise specified, the ring optionally contains 1 to 3 heteroatoms. Thus, the "5- to 7-membered ring" includes, for example, phenyl, pyridyl, and piperidinyl; in another aspect, the term "5- to 7-membered heterocycloalkyl ring" includes pyridyl and piperidinyl, but not phenyl. The term "ring" also includes a ring system comprising at least one ring, wherein each "ring" independently conforms to the above definition.

Unless otherwise specified, the term "heterocyclic ring" or "heterocyclyl" means a stable monocyclic, bicyclic or tricyclic ring containing a heteroatom or heteroatom radical, which may be saturated, partially unsaturated or unsaturated (aromatic), and contains carbon atoms and 1, 2, 3 or 4 cycloheteroatoms independently selected from N, O and S. Among them, any of the above heterocyclic rings may be fused to a benzene ring to form a bicyclic ring. The heteroatoms nitrogen and sulfur may be optionally oxidized (i.e. NO and S(O)$_p$, p is 1 or 2). The nitrogen atom may be substituted or unsubstituted (i.e. N or NR, wherein R is H or other substituents that have been defined herein). The heterocyclic ring may be attached to the pendant group of any heteroatom or carbon atom to form a stable structure. If the resulting compound is stable, the heterocyclic ring described herein may be substituted at the carbon or nitrogen position. The nitrogen atom in the heterocyclic ring is optionally quaternized. In a preferred embodiment, when the total number of S atom and O atom in the heterocyclic ring exceeds 1, these heteroatoms are not adjacent to each other. Another preferred embodiment is that the total number of S atom and O atom in the heterocyclic ring does not exceed 1. As used herein, the term "aromatic heterocyclic group" or "heteroaryl" means a stable 5-, 6-, or 7-membered monocyclic ring or bicyclic ring, or a 7-, 8-, 9-, or 10-membered bicyclic heterocyclic aromatic ring, which contains carbon atoms and 1, 2, 3 or 4 cycloheteroatoms independently selected from N, O and S. The nitrogen atom may be substituted or unsubstituted (i.e. N or NR, wherein R is H or other substituents that have been defined herein). The heteroatoms nitrogen and sulfur may be optionally oxidized (i.e. NO and S(O)$_p$, p is 1 or 2). It is noteworthy that the total number of S atom and O atom in the aromatic heterocyclic ring does not exceed 1. Bridged rings are also included in the definition of heterocyclic rings. A bridged ring is formed when two non-adjacent carbon atoms or nitrogen atoms are linked by one or more atoms (i.e. C, O N, or S). Preferred bridged rings include, but are not limited to: one carbon atom, two carbon atoms, one nitrogen atom, two nitrogen atoms, and one carbon-nitrogen group. It is noteworthy that a bridge always converts a monocyclic ring into a tricyclic ring. In a bridged ring, the substituent(s) in the ring may also appear in the bridge.

Examples of heterocyclic compounds include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazine, phenothiazine, benzoxanthinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolyl, thienyl, thienooxazolyl, thienothiazolyl, thienoimidazolyl, thienyl, triazinyl, 1H-1,2,3-triazolyl, 2H-1,2,3-triazolyl, 1H-1,2,4-triazolyl, 4H-1,2,4-triazolyl, and xanthenyl. Fused-ring compounds and spiro-ring compounds are also included.

Unless otherwise specified, the term "hydrocarbyl" or its subordinate concept(s) (such as alkyl, alkenyl, alkynyl, aryl, etc.) per se or as a part of another substituent represents a linear, branched, or cyclic hydrocarbon radical or a combination thereof, which may be fully saturated (such as alkyl), monounsaturated or polyunsaturated (such as alkenyl, alkynyl and aryl), may be mono-substituted or poly-substituted, may be monovalent (such as methyl), divalent (such as methylene) or polyvalent (such as methine), may include divalent or polyvalent radicals, and has a specified number of carbon atoms (for example, $C_1$-$C_{12}$ means 1 to 12 carbon atoms; $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; and $C_{3-12}$ is selected from $C_3$, $C_4$, $C_5$, $C_6$, $C_7$, $C_8$, $C_9$, $C_{10}$, $C_{11}$ and $C_{12}$). "Hydrocarbyl" includes, but is not limited to, an aliphatic hydrocarbyl and an aromatic hydrocarbyl. Said aliphatic hydrocarbyl includes those with chain structures and those with cyclic structures, and specifically includes, but is not limited to, alkyl, alkenyl and alkynyl. Said aromatic hydrocarbyl includes, but is not limited to, a 6- to 12-membered aromatic hydrocarbyl such as benzene, naphthalene, etc. In some examples, the term "hydrocarbyl" refers to a linear or branched radical or a combination thereof, which may be fully saturated, mono-unsaturated or poly-unsaturated, and may include divalent and polyvalent radicals. Examples of saturated hydrocarbon radicals include, but are not limited to: methyl; ethyl; n-propyl; isopropyl; n-butyl; t-butyl; isobutyl; sec-butyl; isobutyl; cyclohexyl; (cyclohexyl)methyl; cyclopropylmethyl; homologs of radicals such as n-pentyl, n-hexyl, n-heptyl, n-octyl; and isomers thereof. Unsaturated hydrocarbyl has one or more double bonds or triple bonds, and examples thereof include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl" or its subordinate concept(s) (such as heteroalkyl, heteroalkenyl, heteroalkynyl, heteroaryl, etc.) per se or in combination with another term refers to a stable linear, branched or cyclic hydrocarbon radical consisting of a certain number of carbon atoms and at least one heteroatom, or a combination thereof. In some examples, the term "heteroalkyl" per se or in combination with another term refers to a stable linear or branched alkyl radical consisting of a certain number of carbon atoms and at least one heteroatom, or a combination thereof. In a typical example, the heteroatom is selected from B, O, N and S, wherein the nitrogen atom and the sulfur atom are optionally oxidized, and the nitrogen heteroatom is optionally quaternized. The heteroatom or heteroatom radical may be located at any internal position of the heterohydrocarbyl, including the position where the hydrocarbyl is linked to the rest moiety of a molecule. However, the terms "alkoxy", "alkylamino" and "alkylthio" (or thioalkoxy) are used by convention and refer to those alkyl groups that are linked to the rest moiety of a molecule via an oxygen atom, an amino group, or a sulfur atom, respectively. Examples include, but are not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. At most two heteroatoms may appear consecutively, for example, —$CH_2$—NH—$OCH_3$.

Unless otherwise specified, the term "cyclohydrocarbyl", "heterocyclohydrocarbyl" or the subordinate concept(s) thereof (such as aryl, heteroaryl, cycloalkyl, heterocycloalkyl, cycloalkenyl, heterocycloalkenyl, cycloalkynyl, heterocycloalkynyl, etc.) per se or in combination with other terms refers to cyclized "hydrocarbyl" and "heterohydrocarbyl", respectively. In addition, in the case of heterohydrocarbyl or heterocyclohydrocarbyl (such as heteroalkyl, heterocycloalkyl), a heteroatom may occupy the position where the heterocyclic ring is attached to the rest moiety of a molecule. Examples of cyclohydrocarbyl include, but are not limited to, cyclopentyl, cyclohexyl, 1-cyclohexenyl, 3-cyclohexenyl, cycloheptyl, and the like. Non-limiting examples of heterocyclic groups include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindol-3-yl, tetrahydrothiophen-2-yl, tetrahydrothiophen-3-yl, 1-piperazinyl, and 2-piperazinyl.

Unless otherwise specified, the term "heterocycloalkyl" per se or in combination with other terms refers to a cyclized "heteroalkyl". In addition, in the case of "heterocycloalkyl", a heteroatom may occupy the position where the heterocycloalkyl is linked to the rest moiety of a molecule. In some embodiments, said heterocycloalkyl is a 4- to 6-membered heterocycloalkyl; in some other embodiments, said heterocycloalkyl is a 5- to 6-membered heterocycloalkyl. Examples of heterocycloalkyl include, but are not limited to, azetidinyl, oxetanyl, thietanyl, pyrrolidinyl, pyrazolidinyl, imidazolidinyl, tetrahydrothienyl, tetrahydrofuranyl, tetrahydropyranyl, piperidinyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl, oxepanyl,

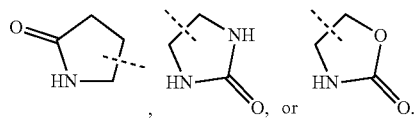
,

Unless otherwise specified, the term "alkyl" is used to represent a linear or branched saturated hydrocarbyl, which may be mono-substituted (such as —$CH_2F$) or poly-substituted (such as —$CF_3$), and may be monovalent (such as methyl), divalent (such as methylene) or polyvalent (such as methine). Examples of alkyl include methyl (Me), ethyl (Et), propyl (e.g. n-propyl and isopropyl), butyl (e.g. n-butyl, isobutyl, s-butyl and t-butyl), pentyl (e.g. n-pentyl, isopentyl and neopentyl), etc.

Unless otherwise specified, cycloalkyl includes any stable cyclic or polycyclic hydrocarbyl, of which any carbon atom is saturated, and which may be mono-substituted or poly-substituted and may be monovalent, divalent or polyvalent. Examples of these cycloalkyls include, but are not limited to, cyclopropyl, norbornanyl, [2.2.2]bicyclooctane, [4.4.0] bicyclodecane, and the like.

Unless otherwise specified, the term "halo" or "halogen" per se or as a part of another substituent means a fluorine atom, a chlorine atom, a bromine atom, or an iodine atom. In addition, the term "haloalkyl" is intended to include a monohaloalkyl and a polyhaloalkyl. For example, the term "halo($C_1$-$C_4$) alkyl" is intended to include, but is not limited to, trifluoromethyl, 2,2,2-trifluoroethyl, 4-chlorobutyl, 3-bromopropyl, and the like. Unless otherwise specified, examples of haloalkyl include, but are not limited to: trifluoromethyl, trichloromethyl, pentafluoroethyl, and pentachloroethyl.

Unless otherwise specified, the term "alkoxy" represents the above-mentioned alkyl having a specific number of carbon atoms which is linked via an oxygen bridge. Unless otherwise specified, $C_{1-6}$ alkoxy includes $C_1$ alkoxy, $C_2$ alkoxy, $C_3$ alkoxy, $C_4$ alkoxy, $C_5$ alkoxy, and $C_6$ alkoxy. Examples of alkoxy include, but are not limited to: methoxy, ethoxy, n-propoxy, isopropoxy, n-butoxy, sec-butoxy, tert-butoxy, n-pentoxy and S-pentoxy.

Unless otherwise specified, the term "alkylamino" refers to —NH-alkyl.

Unless otherwise specified, the term "alkylthio" refers to —S-alkyl.

Unless otherwise specified, the term "acyl" refers to alkyl-C(=O)—.

Unless otherwise specified, the term "alkylsulfonyl" refers to alkyl-S(=O)$_2$—.

Unless otherwise specified, the term "aryl" refers to a polyunsaturated aromatic hydrocarbon substituent, which may be mono-substituted or poly-substituted, may be monovalent, divalent or polyvalent, and may be monocyclic or polycyclic (such as comprising 1 to 3 rings, of which at least one ring is aromatic, and which are fused together or covalently linked).

Unless otherwise specified, the term "heteroaryl" refers to an aryl (or an aromatic ring) containing one to four heteroatoms. In an exemplary example, the heteroatom is selected from B, N, O, and S, wherein the nitrogen atom and the sulfur atom are optionally oxidized, and the nitrogen atom is optionally quaternized. A heteroaryl may be attached to the rest moiety of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl, benzothiazolyl, purinyl, benzoimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalinyl, 5-quinoxalinyl, 3-quinolyl, and 6-quinolyl. A substituent of any one of the above aryl and heteroaryl ring systems is selected from the acceptable substituents described below.

Unless otherwise specified, when used in combination with other terms (e.g. aryloxy, arylthio, arylalkyl), aryl includes the aryl and heteroaryl rings as defined above. Therefore, the term "arylalkyl" is intended to include those radicals in which an aryl is attached to an alkyl (e.g. benzyl, phenylethyl, pyridylmethyl, etc.), including those alkyl groups wherein a carbon atom (such as methylene) has been substituted with, for example, an oxygen atom, such as phenoxymethyl, 2-pyridyloxymethyl-3-(1-naphthoxy)propyl, etc.

Unless otherwise specified, $C_{n-n+m}$ or $C_n$-$C_{n+m}$ includes any specific case in which the number of the carbon atom is from n to n+m (for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{1-2}$), and also includes any range between n and n+m (for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, etc.). Similarly, n-membered to n+m-membered means that the number of the atoms in a ring is from n to n+m (for example, a 3- to 12-membered ring includes a 3-membered ring, a 4-membered ring, a 5-membered ring, a 6-membered ring, a 7-membered ring, a 8-membered ring, a 9-membered ring, a 10-membered ring, a 11-membered ring, and a 12-membered ring), and also includes any range between n and n+m (for example, a 3- to 12-membered ring includes a 3- to 6-membered ring, a 3- to 9-membered ring, a 5- to 6-membered ring, a 5- to 7-membered ring, a 6- to 7-membered ring, a 6- to 8-membered ring, a 6- to 10-membered rings, etc.).

The term "leaving group" refers to a functional group or an atom which may be substituted with another functional group or atom via a substitution reaction (e.g. nucleophilic substitution reaction). For example, representative leaving groups include triflate; chlorine, bromine and iodine; sulfonate group, such as mesylate, tosylate, p-bromobenzenesulfonate, p-tosylate, etc.; acyloxy, such as acetoxy, trifluoroacetoxy, etc.

The term "protecting group" includes, but is not limited to, "amino-protecting group", "hydroxy-protecting group" or "mercapto-protecting group". The term "amino-protecting group" refers to a protecting group suitable for preventing side reactions at the nitrogen position of an amino group. Representative amino-protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethoxycarbonyl, such as benzyloxycarbonyl (Cbz) and 9-fluorenylmethoxycarbonyl (Fmoc); arylmethyl, such as benzyl (Bn), triphenylmethyl (Tr), 1,1-di-(4'-methoxyphenyl)methyl; silyl, such as trimethylsilyl (TMS) and tert-butyldimethylsilyl (TBS), etc. The term "hydroxy-protecting group" refers to a protecting group suitable for preventing side reactions of hydroxy. Representative hydroxy-protecting groups include, but are not limited to: alkyl, such as methyl, ethyl, and t-butyl; acyl, such as alkanoyl (such as acetyl); arylmethyl, such as benzyl (Bn), p-methoxybenzyl (PMB), 9-fluorenylmethyl (Fm) and diphenylmethyl (DPM); silyl, such as trimethylsilyl (TMS) and tert-butyldimethylsilyl (TBS), etc.

The compounds of the present disclosure may be prepared by a variety of synthetic methods well known to a person skilled in the art, including the specific embodiments listed below, embodiments formed by combining said specific embodiments with other chemical synthesis methods, and equivalent alternatives well known to those skilled in the art. Preferred embodiments include, but are not limited to, the examples of the present disclosure.

The solvents used in the present disclosure are commercially available.

The following abbreviations are used in the present disclosure: DMF stands for N,N-dimethylformamide; DMA stands for N,N-dimethylacetamide; TEA stands for triethylamine; DIPEA stands for N,N-diisopropylethylamine; Pd(dppf)Cl$_2$ stands for [1,1'-bis(diphenylphosphino)ferrocene]palladium dichloride; Pd$_2$(dba)$_3$ stands for tris(dibenzylideneacetone)dipalladium; DPPF stands for 1,1'-bisdiphenylphosphinoferrocene; NBS stands for N-bromosuccinimide; POCl$_3$ stands for phosphorus oxychloride; HOBt stands for 1-hydroxybenzotriazole; HATU stands for 2-(7-oxybenzotriazol)-N,N,N',N'-tetramethyluronium hexafluorophosphate; EDCI stands for 1-(3-dimethylaminopropyl)-3-ethylcarbodiimide hydrochloride; DIAD stands for diisopropyl azodicarboxylate; Boc$_2$O stands for di-tert-butyl dicarbonate; and ODPH stands for O-diphenylphosphinylhydroxylamine.

Compounds are named artificially or by using ChemDraw® software, and the commercially available compounds are referred to as the names in the catalogs of suppliers.

DETAILED DESCRIPTION

The present disclosure is described in detail below by Examples, but it does not imply any disadvantageous limitation on the present disclosure. The present disclosure has been described in detail herein, and its specific embodiments are also disclosed therein. Various changes and improvements made to the specific embodiments of the present disclosure without departing from the spirit and scope of the present disclosure will be apparent to a person skilled in the art.

Reaction Scheme 1: Preparation of the compound represented by formula I

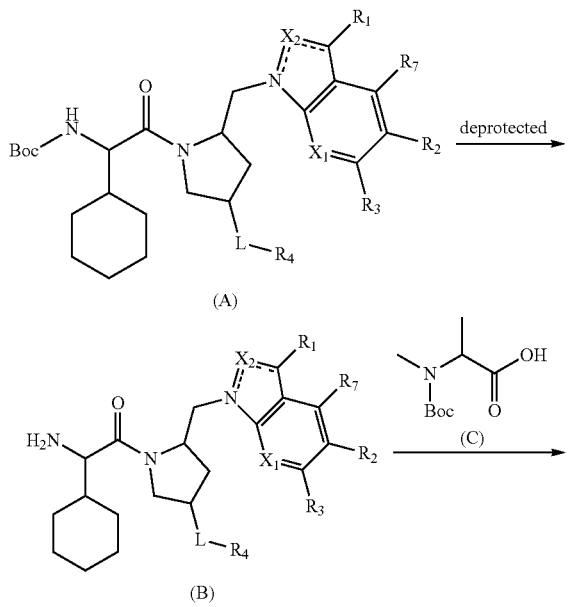

-continued

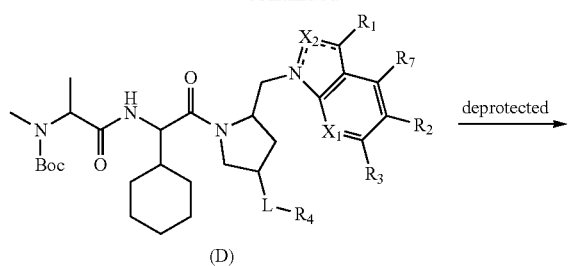

(D)

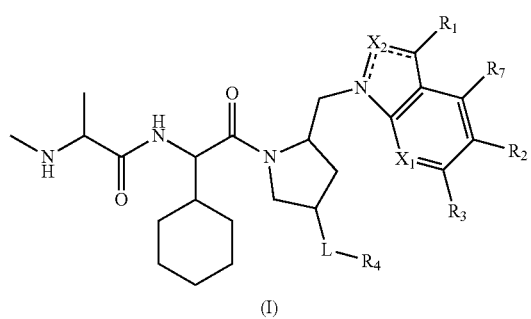

(I)

In the reactions shown in Reaction Scheme 1, Compound (A) is deprotected under an acidic condition (such as a hydrogen chloride/ethyl acetate solution) to obtain Compound (B); Compound (B) and Compound (C) undergo an acid-amine condensation reaction to obtain Compound (D), and this reaction requires a suitable condensing agent (such as HOBt), a suitable dehydrating agent (such as EDCI) and a suitable base (such as DIPEA) according to Reaction Scheme 1; and Compound (D) is then deprotected under an acidic condition (such as a hydrogen chloride/ethyl acetate solution) to obtain the compound represented by formula (I).

Reaction Scheme 2: Preparation of Compound (A) (X$_2$ is not CCl.)

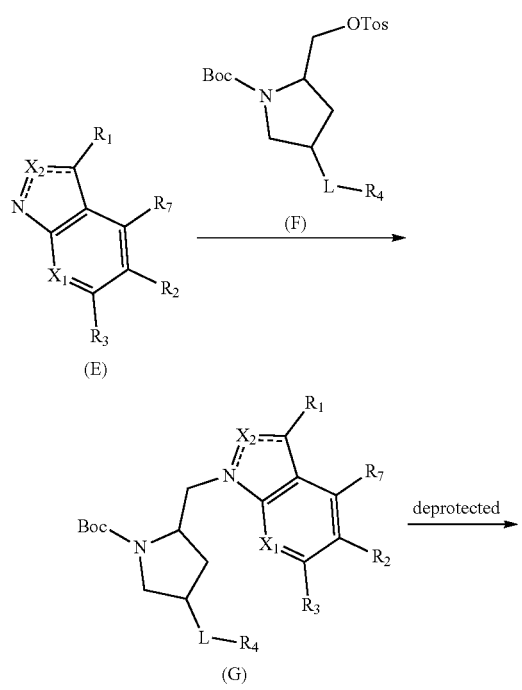

-continued

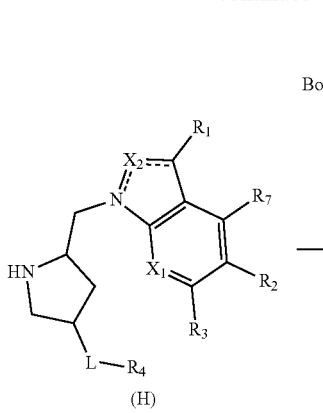

(H)

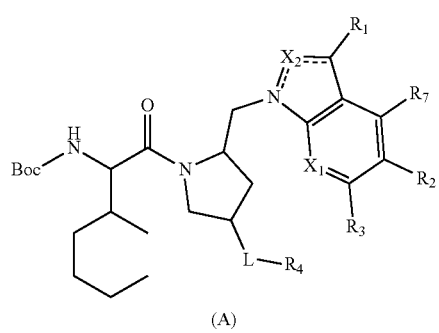

(A)

In the reactions shown in Reaction Scheme 2, Compound (G) may be prepared via a substitution reaction between Compound (E) and Compound (F), this reaction requires a suitable base (such as potassium carbonate) and is preferably carried out at a high temperature according to Reaction Scheme 2; Compound (G) is deprotected under an acidic condition (such as a hydrogen chloride/ethyl acetate solution) to obtain Compound (H); and Compound (A) may be prepared via an acid-amine condensation reaction between Compound (H) and Compound (I), and this reaction requires a suitable condensing agent (such as HOBt), a suitable dehydrating agent (such as EDCI) and a suitable base (such as DIPEA).

Reaction Scheme 3: Preparation of Compound (A) (here, X$_1$ is N and X$_2$ is CCl.)

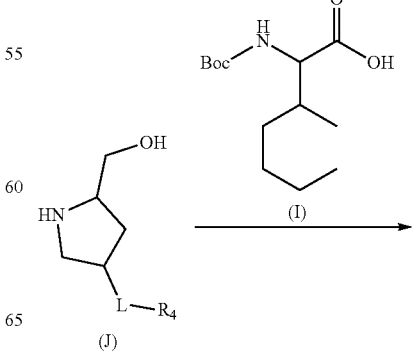

(J)

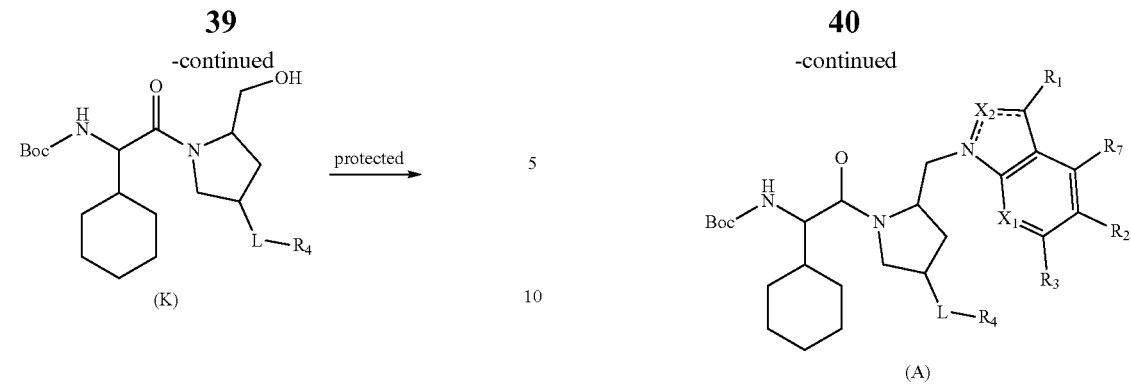

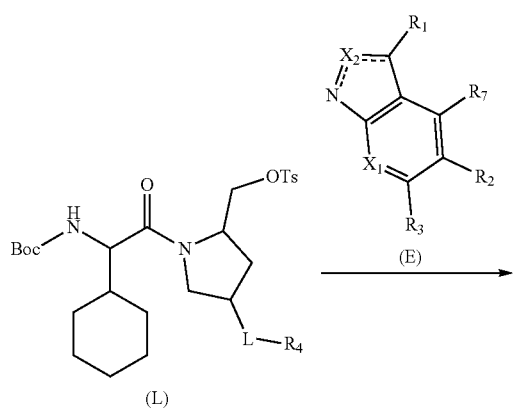

In the reactions shown in Reaction Scheme 3, Compound (K) may be prepared via an acid-amine condensation reaction between Compound (J) and Compound (I), and this reaction requires a suitable condensing agent (such as HATU) and a suitable base (such as DIPEA); Compound (K) is reacted with p-toluenesulfonyl chloride under a basic condition (such as TEA) to obtain Compound (L); and Compound (A) may be prepared via a substitution reaction between Compound (L) and Compound (E) under a basic condition (such as potassium carbonate), and according to Reaction Scheme 2, this reaction is preferably carried out at a high temperature.

Reaction Scheme 4: Preparation of Compound (E) (here, $X_1$ is N and $X_2$ is C.)

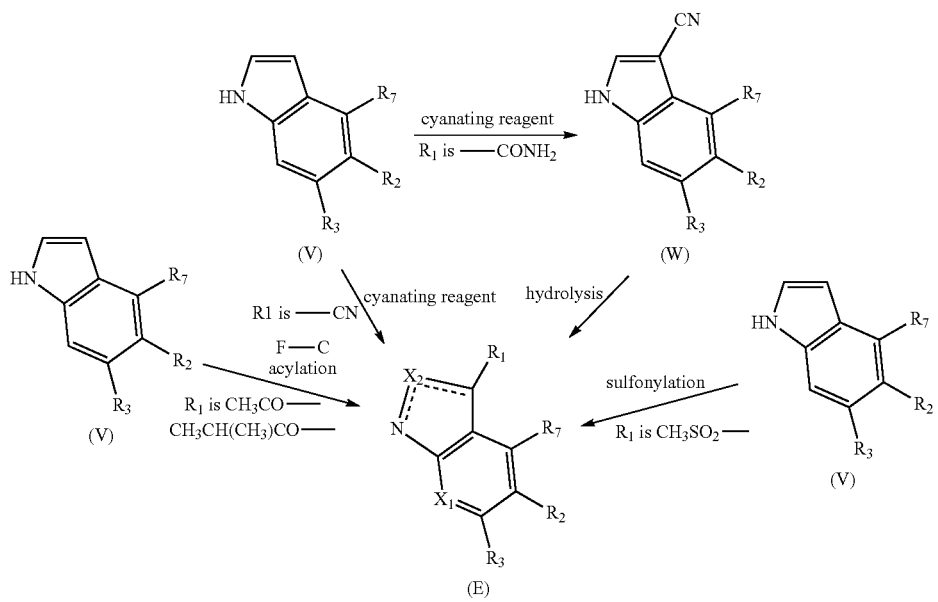

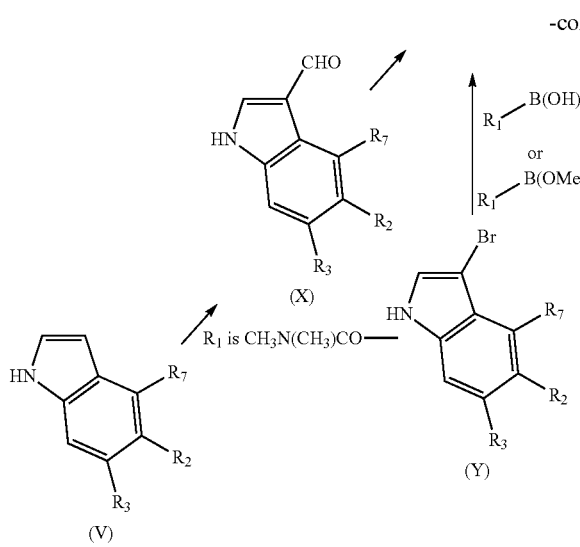
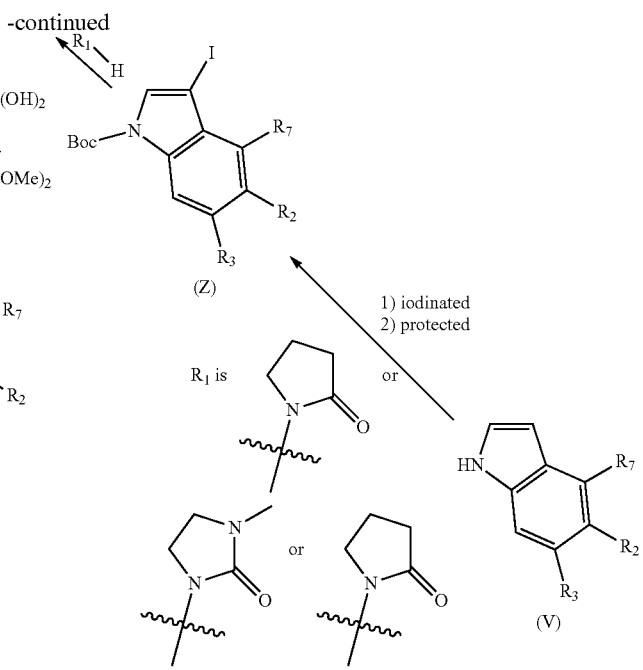
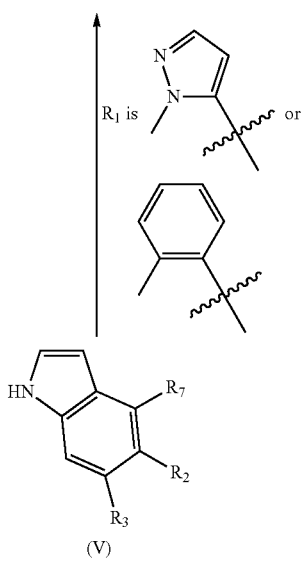

In the reactions shown in Reaction Scheme 4, when $R_1$ is $CH_3CO-$ or $CH_3CH(CH_3)CO-$, Compound (E) may be prepared via an F-C acylation reaction between Compound (V) and the corresponding acyl halide or anhydride, and this reaction requires a suitable catalyst (such as aluminum trichloride).

When $R_1$ is $-CN$, Compound (E) may be prepared by reacting Compound (V) with a cyanating reagent, this reaction requires a suitable cyanating reagent (such as chlorosulfonyl isocyanate), and according to Reaction Scheme 4, this reaction is preferably carried out at a low temperature.

When $R_1$ is $-CONH_2$, Compound (V) is reacted with a cyanating reagent to give Compound (W), this reaction requires a suitable cyanating reagent (such as chlorosulfonyl isocyanate), and according to Reaction Scheme 4, this reaction is preferably carried out at a low temperature; Compound (E) may be prepared via a hydrolysis reaction of Compound (W) under a basic condition, and this reaction requires a suitable base (such as potassium carbonate) and a suitable solvent (such as an ethanol/hydrogen peroxide mixed solvent).

When $R_1$ is $CH_3SO_2-$, Compound (E) may be prepared via a sulfonylation reaction between Compound (V) and methanesulfonyl chloride under a basic condition, this reaction requires a suitable base (such as potassium tert-butoxide) and a suitable catalyst (such as a solution of triethylborane in tetrahydrofuran), and according to Reaction Scheme 4, this reaction is preferably carried out at a low temperature.

When $R_1$ is $CH_3N(CH_3)CO-$, a Vilsmeier-Haack reaction of Compound (V) with $POCl_3$ and DMF gives Compound (X). Compound (E) may be prepared by reacting Compound (X) with dimethylamine, and this reaction requires a suitable catalyst (such as sodium cyanide) and a suitable oxidant (such as manganese dioxide).

When R₁ is

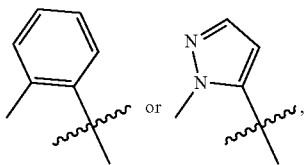

a halogenation reaction between Compound (V) and a brominating reagent gives Compound (Y), and this reaction requires a suitable brominating reagent (such as NBS). Compound (E) may be prepared via a Suzuki coupling reaction of Compound (Y) with the corresponding boric acid or boric acid ester, this reaction requires a suitable catalyst (such as Pd(dppf)Cl₂) and a suitable base (such as potassium phosphate), and according to Reaction Scheme 4, this reaction is preferably carried out at a high temperature.

When R₁ is

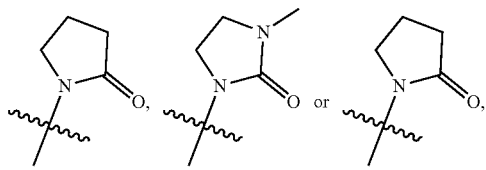

a halogenation reaction between Compound (V) and an iodinating reagent gives an intermediate compound and this reaction requires a suitable iodinating reagent (such as elemental iodine), and then the intermediate compound is reacted with Boc₂O to obtain Compound (Z) and this reaction requires a suitable catalyst (such as DMAP) and a suitable base (such as TEA). Compound (E) may be prepared via a Ullmann coupling reaction between Compound (Z) and the corresponding compound with a saturated five-membered aza-ring, this reaction requires a suitable catalyst (such as cuprous iodide), a suitable ligand (such as N,N-dimethylethylenediamine) and a suitable base (such as cesium carbonate), and according to Reaction Scheme 4, this reaction is preferably carried out at a high temperature.

Example 1

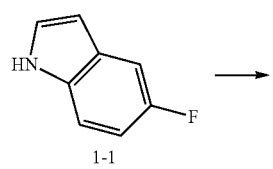

1-1

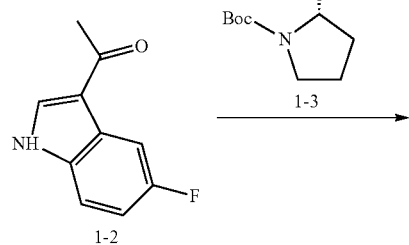

1-2

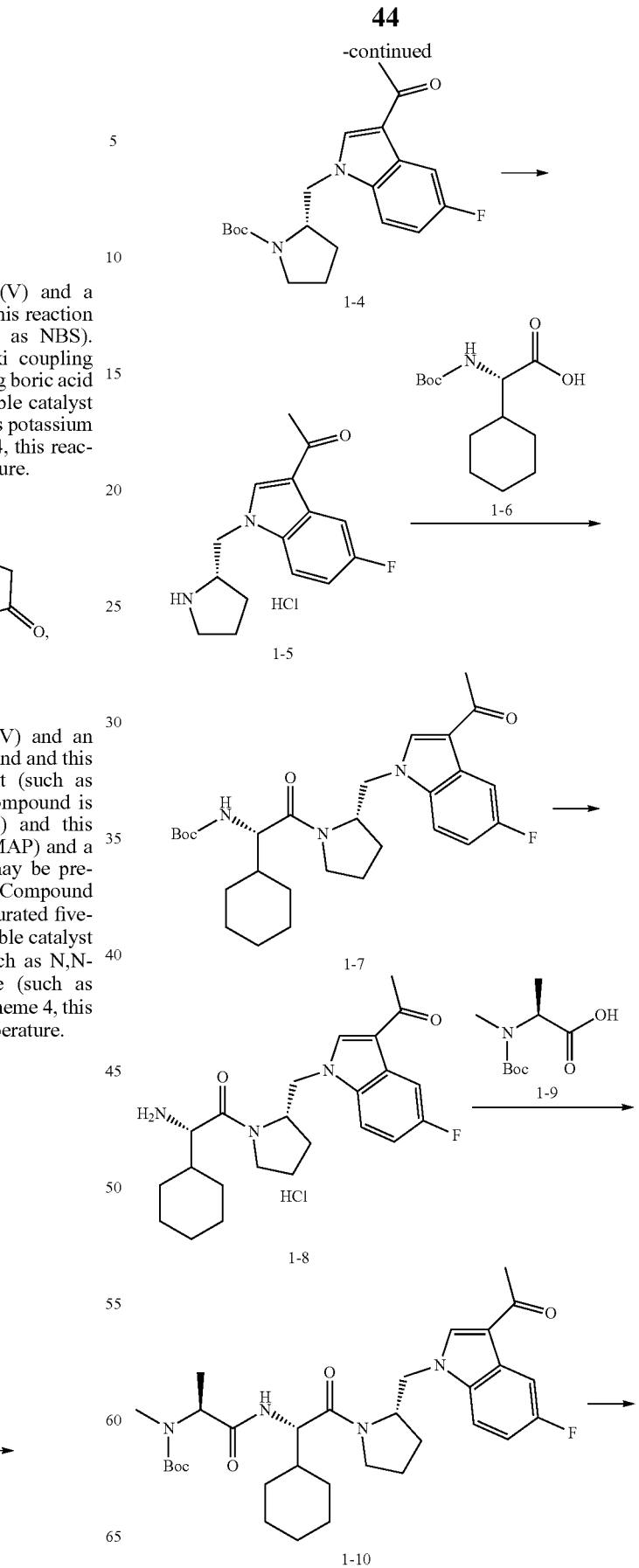

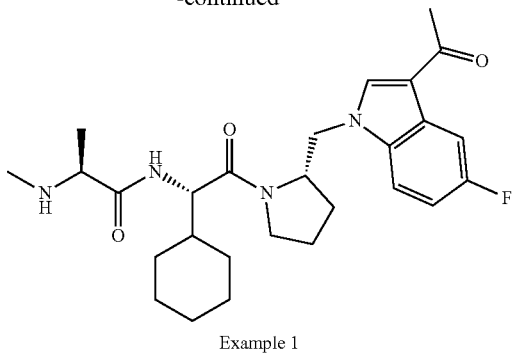

Example 1

Step 1:

Acetic anhydride (7.55 g, 74 mmol, 6.93 mL, 2.0 equiv.) was added dropwise into a suspension of ammonium chloride (7.92 g, 148 mmol, 5.17 mL, 4.0 equiv.) in 1,2-dichloroethane (100 mL) at 15° C. The mixture was stirred at 15° C. for 30 minutes, and a solution of Compound 1-1 (5.0 g, 37 mmol, 1.0 equiv.) in 1,2-dichloroethane (50 mL) was added into the mixture. The resulting mixture was stirred at 15° C. for 2 hours. Aluminum trichloride (9.87 g, 74 mmol, 2.0 equiv.) was added into the reaction solution, and the reaction solution was changed from heterogeneous to homogeneous. Acetic anhydride (3.78 g, 37 mmol, 3.47 mL, 1.0 equiv.) was further added into the reaction solution, and the reaction solution was stirred at 15° C. for 30 minutes. LCMS showed that the starting materials were reacted completely. The reaction solution was slowly poured into ice water (200 mL), and the resulting mixture was extracted with ethyl acetate (100 mL×2). The combined organic phases were washed with saline (100 mL), then the resulting mixture was subjected to liquid-liquid separation, and the resultant was concentrated under reduced pressure. The resulting residue was purified by silica gel column chromatography (petroleum ether:ethyl acetate=10:1 to 1:1) to obtain Compound 1-2. LCMS (ESI) m/z: 178.1 (M+1).

Step 2:

Compound 1-3 (7.11 g, 20.01 mmol, 3.0 equiv.) and potassium carbonate (4.61 g, 33.35 mmol, 5.0 equiv.) were added into a solution of Compound 1-2 (1.36 g, 6.67 mmol, 1.0 equiv.) in DMF (20 mL). Under the protection of nitrogen, the resulting mixture was heated to 100° C. and reacted for 15 hours. LCMS showed that the starting materials were not reacted completely. The reaction solution was heated to 120° C. and reacted for 2 hours. LCMS showed that the reaction was complete. Water (30 mL) was added into the reaction solution, and the resulting mixture was extracted with ethyl acetate (30 mL×3). The combined organic phases were washed with saline (30 mL) and then concentrated, and the resulting residue was purified by silica gel column chromatography (petroleum ether:ethyl acetate=10:1 to 3:1) to obtain Compound 1-4. LCMS (ESI) m/z: 361.1 (M+1).

Step 3:

A hydrogen chloride/ethyl acetate solution (4.0 mol/L, 20 mL, 21.57 equiv.) was added into a solution of Compound 1-4 (2.0 g, 3.71 mmol, 1.0 equiv.) in ethyl acetate (20 mL) at 0° C. After the resulting reaction solution was stirred at 15° C. for 1 hour, a large amount of solid precipitated, and LCMS showed that the reaction was complete. The reaction solution was filtered, and the filter cake was washed with ethyl acetate (10 mL) and then dried to obtain Compound 1-5. The crude product was directly used in the next step. $^1$H NMR (400 MHz, DMSO-$d_6$) δ 8.75 (s, 1H), 7.90-7.79 (m, 2H), 7.17 (dt, J=9.2, 2.6 Hz, 1H), 4.84-4.58 (m, 2H), 3.36-3.20 (m, 1H), 3.19-3.04 (m, 1H), 2.44 (d, J=2.8 Hz, 4H), 2.18-2.06 (m, 1H), 2.02 (br dd, J=7.9, 5.5 Hz, 1H), 1.88 (td, J=12.6, 7.9 Hz, 1H), 1.80-1.67 (m, 1H); LCMS (ESI) m/z: 261.1 (M+1).

Step 4:

Compound 1-6 (1.30 g, 5.05 mmol, 1.5 equiv.), HOBt (500.85 mg, 3.71 mmol, 1.1 equiv.), EDCI (710.56 mg, 3.71 mmol, 1.1 equiv.) and DIPEA (1.31 g, 10.11 mmol, 1.76 mL, 3 equiv.) were added into a solution of Compound 1-5 (1.0 g, 3.37 mmol, 1.0 equiv.) in dichloromethane (30 mL), and the resulting mixture was reacted at 15° C. for 16 hours. LCMS showed that the reaction was complete. The reaction solution was poured into water (50 mL), and the resulting mixture was extracted with dichloromethane (50 mL×3). The combined organic phases were concentrated, and the resulting residue was purified by silica gel column chromatography (petroleum ether:ethyl acetate=10:1 to 1:1) to obtain Compound 1-7. LCMS (ESI) m/z: 500.2 (M+1).

Step 5:

Hydrogen chloride/ethyl acetate (4.0 mol/L, 20 mL, 23.61 equiv.) was added into a solution of Compound 1-7 (1.75 g, 3.39 mmol, 1.0 equiv.) in ethyl acetate (20 mL) at 0° C. The mixture was reacted at 15° C. for 1 hour, and LCMS showed that the reaction was complete. The reaction solution was concentrated to obtain Compound 1-8, and the crude product was directly used in the next step. LCMS (ESI) m/z: 400.1 (M+1).

Step 6:

Compound 1-9 (1.05 g, 5.16 mmol, 1.5 equiv.), HOBt (511.41 mg, 3.78 mmol, 1.1 equiv.), EDCI (725.54 mg, 3.78 mmol, 1.1 equiv.) and DIPEA (1.33 g, 10.32 mmol, 1.8 mL, 3 equiv.) were added into a solution of Compound 1-8 (1.5 g, 3.44 mmol, 1.0 equiv.) in dichloromethane (30 mL), and the resulting reaction solution was reacted at 15° C. for 14 hours. LCMS showed that the reaction was complete. The reaction solution was poured into water (50 mL), the resulting mixture was extracted with dichloromethane (50 mL×3), and the combined organic phases were concentrated. The resulting residue was purified by silica gel column chromatography (petroleum ether:ethyl acetate=2:1 to 1:4) to obtain Compound 1-10. LCMS (ESI) m/z: 585.3 (M+1).

Step 7:

Hydrogen chloride/ethyl acetate (4.0 mol/L, 18.57 mL, 33.41 equiv.) was added into a solution of Compound 1-10 (1.30 g, 2.22 mmol, 1.0 equiv.) in ethyl acetate (20 mL) at 0° C. The resulting mixture was reacted at 15° C. for 1 hour. LCMS showed that the reaction was complete. The reaction solution was concentrated, and the resulting residue was purified by preparative HPLC (hydrochloric acid system, mobile phase: water (0.05% hydrochloric acid)-acetonitrile, gradient: acetonitrile: 15% to 25%) to obtain the hydrochloride of Example 1. $^1$H NMR (400 MHz, CD$_3$OD) δ 8.28 (s, 1H), 7.87 (dd, J=9.7, 2.4 Hz, 1H), 7.78 (dd, J=8.9, 4.2 Hz, 1H), 7.04 (dt, J=9.0, 2.4 Hz, 1H), 4.56-4.42 (m, 3H), 4.14-4.02 (m, 1H), 3.95 (q, J=6.8 Hz, 1H), 3.83 (q, J=8.4 Hz, 1H), 3.77-3.66 (m, 1H), 2.67 (s, 3H), 2.50 (s, 3H), 2.25-2.09 (m, 1H), 2.03-1.93 (m, 1H), 1.85-1.64 (m, 9H), 1.51 (d, J=7.0 Hz, 3H), 1.33-1.01 (m, 6H); LCMS (ESI) m/z: 485.2 (M+1).

Example 2

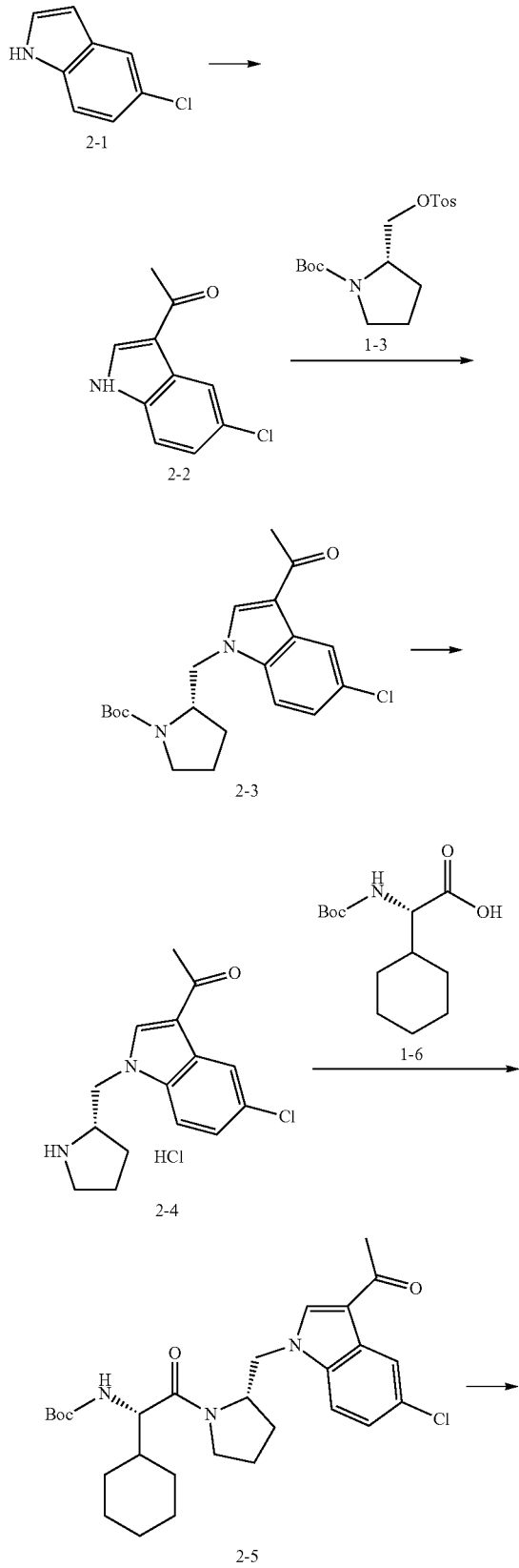

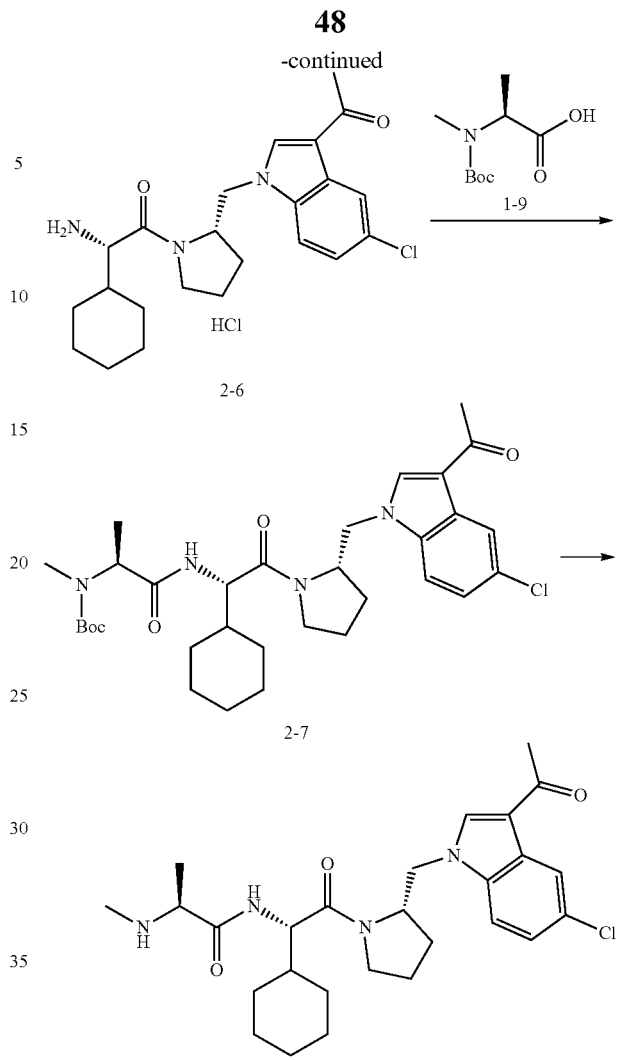

Example 2

Step 1:

Acetic anhydride (6.73 g, 65.97 mmol, 6.18 mL, 2.0 equiv.) was added into a suspension of ammonium chloride (3.53 g, 65.97 mmol, 2.31 mL, 2.0 equiv.) in 1,2-dichloroethane (10 mL) at 15° C., and the mixture was stirred at 15° C. for 15 minutes. Compound 2-1 (5.0 g, 32.98 mmol, 1.0 equiv.) was added into the mixture, and the resulting mixture was stirred at 15° C. for 2 hours. Aluminum trichloride (8.80 g, 65.97 mmol, 2.0 equiv.) was added into the reaction solution, and the reaction solution was stirred at 15° C. for 30 minutes. Acetic anhydride (3.37 g, 32.98 mmol, 3.09 mL, 1.0 equiv.) was further added into the reaction solution, and the reaction solution was stirred at 15° C. for 15 minutes. LCMS showed that the starting materials were reacted completely. The reaction solution was slowly poured into ice water, and the resulting mixture was extracted with ethyl acetate (100 mL×3). The extract liquor was dried over $Na_2SO_4$ and concentrated under reduced pressure. The resulting residue was purified by silica gel column chromatography (petroleum ether:ethyl acetate=1:1) to obtain Compound 2-2. LCMS (ESI) m/z: 194.1 (M+1).

Step 2:

Compound 2-2 (2.00 g, 10.33 mmol, 1.0 equiv.) and potassium carbonate (7.14 g, 51.65 mmol, 5.0 equiv.) were added into a solution of Compound 1-3 (7.54 g, 20.66 mmol, 2.0 equiv.) in DMF (70 mL), and the mixture was heated and stirred for 12 hours at 100° C. Water (300 mL) and ethyl acetate (300 mL) were added into the reaction solution, and the organic phase was washed with saline (100 mL), dried over $Na_2SO_4$, filtered, and concentrated under reduced pressure to obtain Compound 2-3. LCMS (ESI) m/z: 377.0 (M+1).

Step 3:

A hydrogen chloride/dioxane solution (4.0 mol/L, 20 mL, 26.04 equiv.) was added into a solution of Compound 2-3 (2.4 g, 3.07 mmol, 1.0 equiv.) in dioxane (20 mL), and the resulting reaction solution was stirred at 15° C. for 10 hours. LCMS showed that the reaction was complete. The reaction solution was filtered, and the filter cake was washed with ethyl acetate (10 mL×3) and then dried to obtain Compound 2-4. The crude product was directly used in the next step. LCMS (ESI) m/z: 277.1 (M+1).

Step 4:

DIPEA (857.20 mg, 6.63 mmol, 1.16 mL, 3 equiv.) and HATU (1.01 g, 2.65 mmol, 1.2 equiv.) were added into a solution of Compound 1-6 (625.81 mg, 2.43 mmol, 1.1 equiv.) in DMF (5 mL), and the mixture was stirred at 15° C. for 30 minutes. Compound 2-4 (700 mg, 2.21 mmol, 1.0 equiv., hydrochloride) was added into the reaction solution, and the reaction mixture was stirred at 15° C. for 1.5 hours. Water (30 mL) and ethyl acetate (40 mL) were added into the reaction solution. The organic phase was washed with citric acid (20 mL, 10% aqueous solution) and saline (20 mL), dried over $Na_2SO_4$, filtered, and concentrated under reduced pressure to obtain Compound 2-5. LCMS (ESI) m/z: 516.2 (M+1).

Step 5:

Hydrogen chloride/dioxane (4.0 mol/L, 18.33 mL, 34.40 equiv.) was added into a solution of Compound 2-5 (1.10 g, 2.13 mmol, 1.0 equiv.) in dioxane (10 mL), and the mixture was reacted at 15° C. for 1.5 hours. The reaction solution was filtered, and the filter cake was washed with ethyl acetate (20 mL) and then dried to obtain Compound 2-6. LCMS (ESI) m/z: 416.2 (M+1).

Step 6:

DIPEA (326.91 mg, 2.53 mmol, 440.58 μL, 3 equiv.), HATU (384.71 mg, 1.01 mmol, 1.2 equiv.) and Compound 2-6 (500 mg, 843.16 μmol, 1.0 equiv., hydrochloride) were added into a solution of Compound 1-9 (188.50 mg, 927.48 μmol, 1.1 equiv.) in DMF (5 mL), and the reaction mixture was stirred at 15° C. for 1 hour. Water (30 mL) and ethyl acetate (20 mL) were added into the reaction solution. The organic phase was washed with citric acid (20 mL, 10% aqueous solution) and saline (20 mL), dried over $Na_2SO_4$, filtered, and concentrated under reduced pressure to obtain Compound 2-7. The crude product was directly used in the next step. LCMS (ESI) m/z: 601.1 (M+1).

Step 7:

Trifluoroacetic acid (3 mL) was added into a solution of Compound 2-7 (500 mg, 787.28 μmol, 1.0 equiv.) in dichloromethane (10 mL) at 0° C., and the resulting mixture was reacted at 0° C. for 1 hour. LCMS showed that the reaction was complete. The reaction solution was concentrated, and the resulting residue was purified by preparative HPLC (hydrochloric acid) to obtain the hydrochloride of Example 2. LCMS (ESI) m/z: 501.4 (M+1). $^1$H NMR (400 MHz, DMSO-$d_6$) δ 9.50 (br s, 1H), 8.88 (br d, J=5.3 Hz, 1H), 8.78 (d, J=8.2 Hz, 1H), 8.47 (s, 1H), 8.15 (d, J=2.1 Hz, 1H), 7.89 (d, J=8.8 Hz, 1H), 7.32 (dd, J=2.1, 8.7 Hz, 1H), 4.48-4.33 (m, 3H), 4.10 (br dd, J=14.8, 9.9 Hz, 1H), 3.90-3.90 (m, 1H), 3.73-3.54 (m, 2H), 2.46-2.45 (m, 1H), 2.44 (s, 3H), 2.16-2.01 (m, 1H), 1.97-1.81 (m, 1H), 1.79-1.52 (m, 9H), 1.34 (d, J=6.8 Hz, 3H), 1.27-0.87 (m, 6H).

Example 3

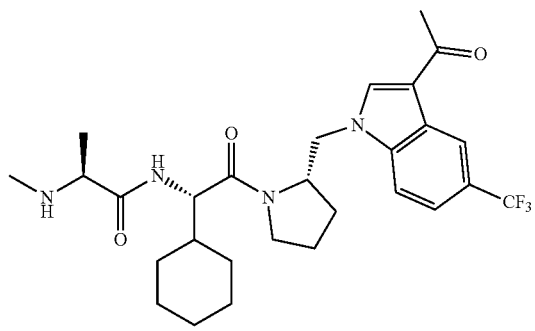 [SMILES: CN[C@@H](C)C(=O)N[C@H](C(=O)N1CCC[C@H]1Cn1cc(C(C)=O)c2cc(C(F)(F)F)ccc21)C1CCCCC1]

Please refer to Example 1 for the preparation method of Example 3. $^1$H NMR (400 MHz, CD$_3$OD) δ 8.57 (s, 1H), 8.41 (s, 1H), 7.97 (d, J=8.7 Hz, 1H), 7.55 (dd, J=8.7, 1.6 Hz, 1H), 4.64-4.54 (m, 2H), 4.48 (d, J=7.7 Hz, 1H), 4.25-4.12 (m, 1H), 3.95-3.81 (m, 2H), 3.79-3.69 (m, 1H), 2.67 (s, 3H), 2.55 (s, 3H), 2.26-2.12 (m, 1H), 2.09-1.97 (m, 1H), 1.91-1.59 (m, 9H), 1.50 (d, J=7.0 Hz, 3H), 1.36-0.97 (m, 6H); LCMS (ESI) m/z: 535.2 (M+1).

Example 4

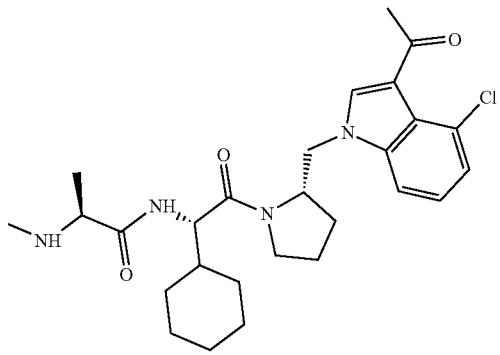 [SMILES: CN[C@@H](C)C(=O)N[C@H](C(=O)N1CCC[C@H]1Cn1cc(C(C)=O)c2c(Cl)cccc21)C1CCCCC1]

Please refer to Example 1 for the preparation method of Example 4. $^1$H NMR (400 MHz, DMSO-$d_6$) δ 9.32 (br s, 1H), 8.85 (br d, J=5.9 Hz, 1H), 8.78 (br d, J=8.2 Hz, 1H), 8.45 (s, 1H), 7.88 (d, J=7.1 Hz, 1H), 7.31-7.20 (m, 2H), 4.48-4.36 (m, 3H), 4.14-4.04 (m, 1H), 3.92-3.81 (m, 1H), 3.73-3.64 (m, 1H), 3.63-3.56 (m, 1H), 2.49-2.45 (m, 4H), 2.17-2.02 (m, 1H), 1.96-1.84 (m, 1H), 1.81-1.56 (m, 9H), 1.34 (d, J=6.8 Hz, 3H), 1.27-0.95 (m, 6H); LCMS (ESI) m/z: 501.4 (M+1).

Example 5

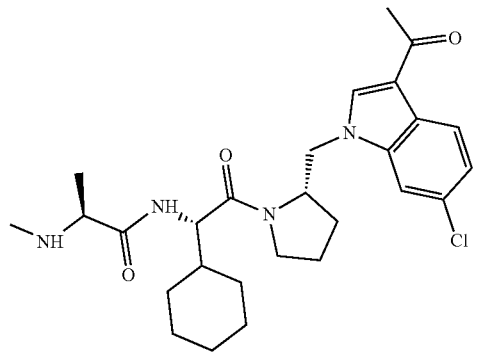 [SMILES: CN[C@@H](C)C(=O)N[C@H](C(=O)N1CCC[C@H]1Cn1cc(C(C)=O)c2ccc(Cl)cc21)C1CCCCC1]

Please refer to Example 1 for the preparation method of Example 5. ¹H NMR (400 MHz, DMSO-d$_6$) δ 9.50 (br s, 1H), 8.96-8.85 (m, 1H), 8.82 (d, J=8.3 Hz, 1H), 8.45 (s, 1H), 8.15 (d, J=8.5 Hz, 1H), 8.00 (d, J=1.6 Hz, 1H), 7.24 (dd, J=8.5, 1.8 Hz, 1H), 4.47-4.35 (m, 3H), 4.08 (dd, J=14.5, 9.9 Hz, 1H), 3.89-3.80 (m, 1H), 3.74-3.66 (m, 1H), 3.64-3.56 (m, 1H), 2.46 (br s, 1H), 2.44 (s, 3H), 2.18-2.05 (m, 1H), 1.96-1.84 (m, 1H), 1.79-1.57 (m, 9H), 1.35 (d, J=6.8 Hz, 3H), 1.27-0.95 (m, 6H); LCMS (ESI) m/z: 501.4 (M+1).

Example 6

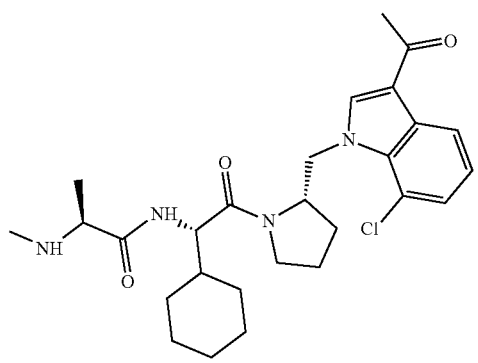 [SMILES: CN[C@@H](C)C(=O)N[C@H](C(=O)N1CCC[C@H]1Cn1cc(C(C)=O)c2cccc(Cl)c21)C1CCCCC1]

Please refer to Example 1 for the preparation method of Example 6. ¹H NMR (400 MHz, DMSO-d$_6$) δ 9.30 (br s, 1H), 8.80 (br s, 1H), 8.59 (br d, J=7.8 Hz, 1H), 8.39 (br s, 1H), 8.19 (br d, J=7.8 Hz, 1H), 7.37-7.07 (m, 2H), 4.87-4.59 (m, 2H), 4.57-4.29 (m, 2H), 3.79 (br s, 1H), 3.65 (br s, 2H), 2.43 (br s, 7H), 2.16-1.23 (m, 13H), 1.21-0.73 (m, 5H); LCMS (ESI) m/z: 501.3 (M+1).

Example 7

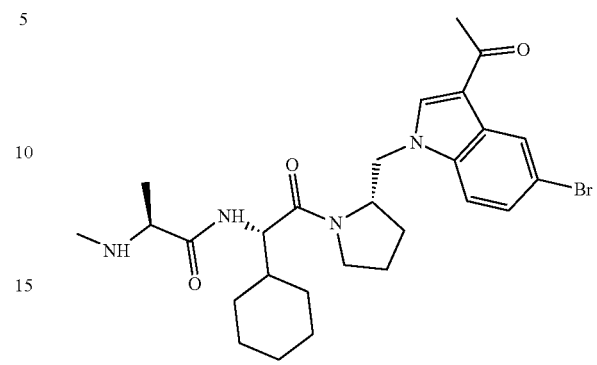

Please refer to Example 1 for the preparation method of Example 7. ¹H NMR (400 MHz, DMSO-d$_6$) δ 9.60-9.44 (m, 1H), 8.97-8.84 (m, 1H), 8.79 (br d, J=8.2 Hz, 1H), 8.46 (s, 1H), 8.31 (d, J=1.8 Hz, 1H), 7.84 (d, J=8.8 Hz, 1H), 7.43 (dd, J=8.8, 2.0 Hz, 1H), 4.47-4.35 (m, 3H), 4.18-3.98 (m, 1H), 3.85 (br d, J=4.8 Hz, 1H), 3.73-3.64 (m, 1H), 2.47-2.42 (m, 6H), 2.17-2.02 (m, 1H), 1.98-1.85 (m, 1H), 1.81-1.52 (m, 9H), 1.34 (d, J=6.8 Hz, 3H), 1.21-0.98 (m, 5H); LCMS (ESI) m/z: 547.2 (M+1).

Example 8

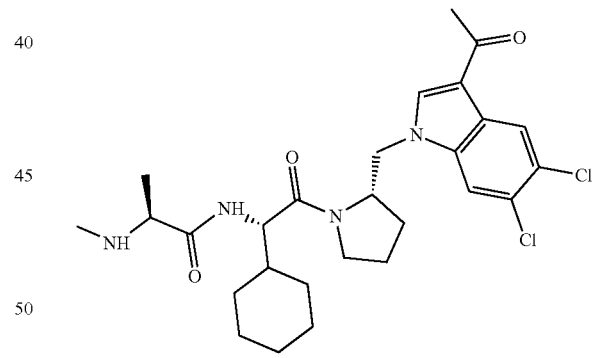

Please refer to Example 1 for the preparation method of Example 8. ¹H NMR (400 MHz, DMSO-d$_6$) δ 9.60-9.48 (m, 1H), 8.96-8.83 (m, 1H), 8.79 (d, J=8.3 Hz, 1H), 8.53 (s, 1H), 8.28 (s, 1H), 8.20 (s, 1H), 4.48-4.32 (m, 3H), 4.11 (br dd, J=13.3, 8.2 Hz, 1H), 3.83-3.77 (m, 1H), 3.73-3.65 (m, 1H), 3.64-3.52 (m, 1H), 2.47-2.43 (m, 6H), 2.21-2.03 (m, 1H), 1.96-1.84 (m, 1H), 1.77-1.72 (m, 2H), 1.67-1.55 (m, 5H), 1.34 (d, J=6.8 Hz, 3H), 1.26-0.86 (m, 6H); LCMS (ESI) m/z: 535.3 (M+1).

Example 9

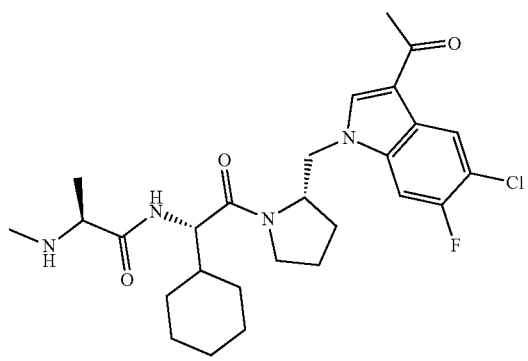 [SMILES: CN[C@@H](C)C(=O)N[C@H](C(=O)N1CCC[C@H]1Cn1cc(C(C)=O)c2cc(Cl)c(F)cc21)C1CCCCC1]

Example 11

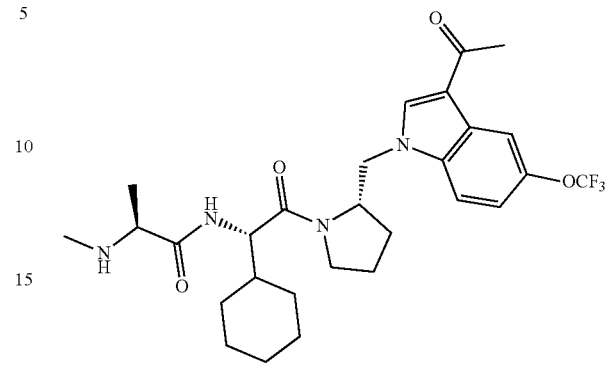

Please refer to Example 1 for the preparation method of Example 9. $^1$H NMR (400 MHz, DMSO-$d_6$) δ 0.89-1.27 (m, 6H) 1.34 (d, J=6.85 Hz, 3H), 1.58-1.70 (m, 5H), 1.73-1.80 (m, 2H), 1.86-1.97 (m, 1H), 2.05-2.19 (m, 1H), 2.42-2.47 (m, 6H), 3.50-3.74 (m, 2H), 3.79-3.91 (m, 1H), 4.11 (dd, J=13.75, 8.50 Hz, 1H), 4.26-4.46 (m, 3H), 7.98 (d, J=10.15 Hz, 1H), 8.19-8.24 (m, 1H), 8.49 (s, 1H), 8.75 (d, J=8.19 Hz, 1H), 8.86 (br d, J=5.62 Hz, 1H), 9.43 (br s, 1H); LCMS (ESI) m/z: 519.3 (M+1).

Please refer to Example 1 for the preparation method of Example 11. $^1$H NMR (400 MHz, DMSO-$d_6$) δ 0.96-1.19 (m, 5H), 1.30-1.42 (m, 3H), 1.53-1.80 (m, 1H), 1.53-1.82 (m, 7H), 1.90 (br s, 1H), 2.02-2.17 (m, 1H), 2.41-2.48 (m, 6H), 3.57-3.63 (m, 1H), 3.83-3.91 (m, 1H), 4.07-4.19 (m, 1H), 4.37-4.46 (m, 2H), 7.28 (br d, J=8.19 Hz, 1H), 7.97 (d, J=8.93 Hz, 1H), 8.03-8.13 (m, 1H), 8.55 (s, 1H), 8.79 (br d, J=7.95 Hz, 1H), 8.90 (br s, 1H), 9.60 (br s, 1H); LCMS (ESI) m/z: 551.3 (M+1).

Example 10

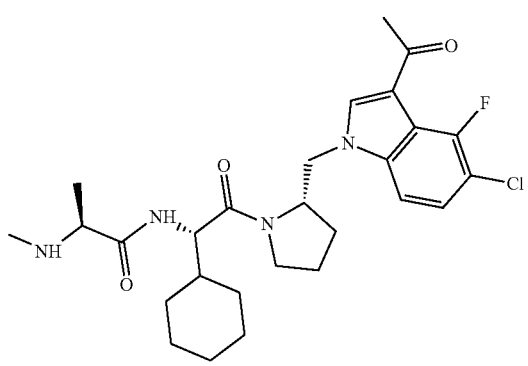 [SMILES: CN[C@@H](C)C(=O)N[C@H](C(=O)N1CCC[C@H]1Cn1cc(C(C)=O)c2c(F)c(Cl)ccc21)C1CCCCC1]

Example 12

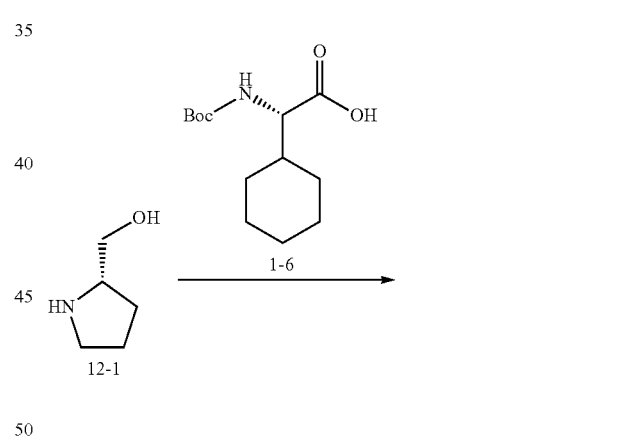

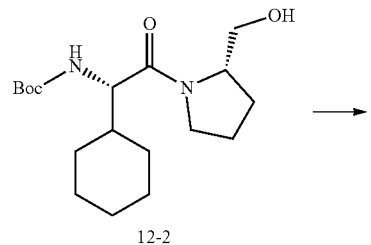

Please refer to Example 1 for the preparation method of Example 10. $^1$H NMR (400 MHz, DMSO-$d_6$) δ 9.63-9.35 (m, 1H), 8.88 (br d, J=5.3 Hz, 1H), 8.76 (br d, J=8.1 Hz, 1H), 8.55-8.43 (m, 1H), 7.73 (d, J=8.8 Hz, 1H), 7.41 (dd, J=8.4, 6.7 Hz, 1H), 4.47-4.29 (m, 3H), 4.19-4.05 (m, 1H), 3.95-3.78 (m, 1H), 3.16 (s, 3H), 2.47-2.43 (m, 5H), 2.21-2.02 (m, 1H), 1.90 (br d, J=3.3 Hz, 1H), 1.84-1.46 (m, 9H), 1.33 (br d, J=6.7 Hz, 3H), 1.22-0.91 (m, 5H); LCMS (ESI) m/z: 519.3 (M+1).

-continued

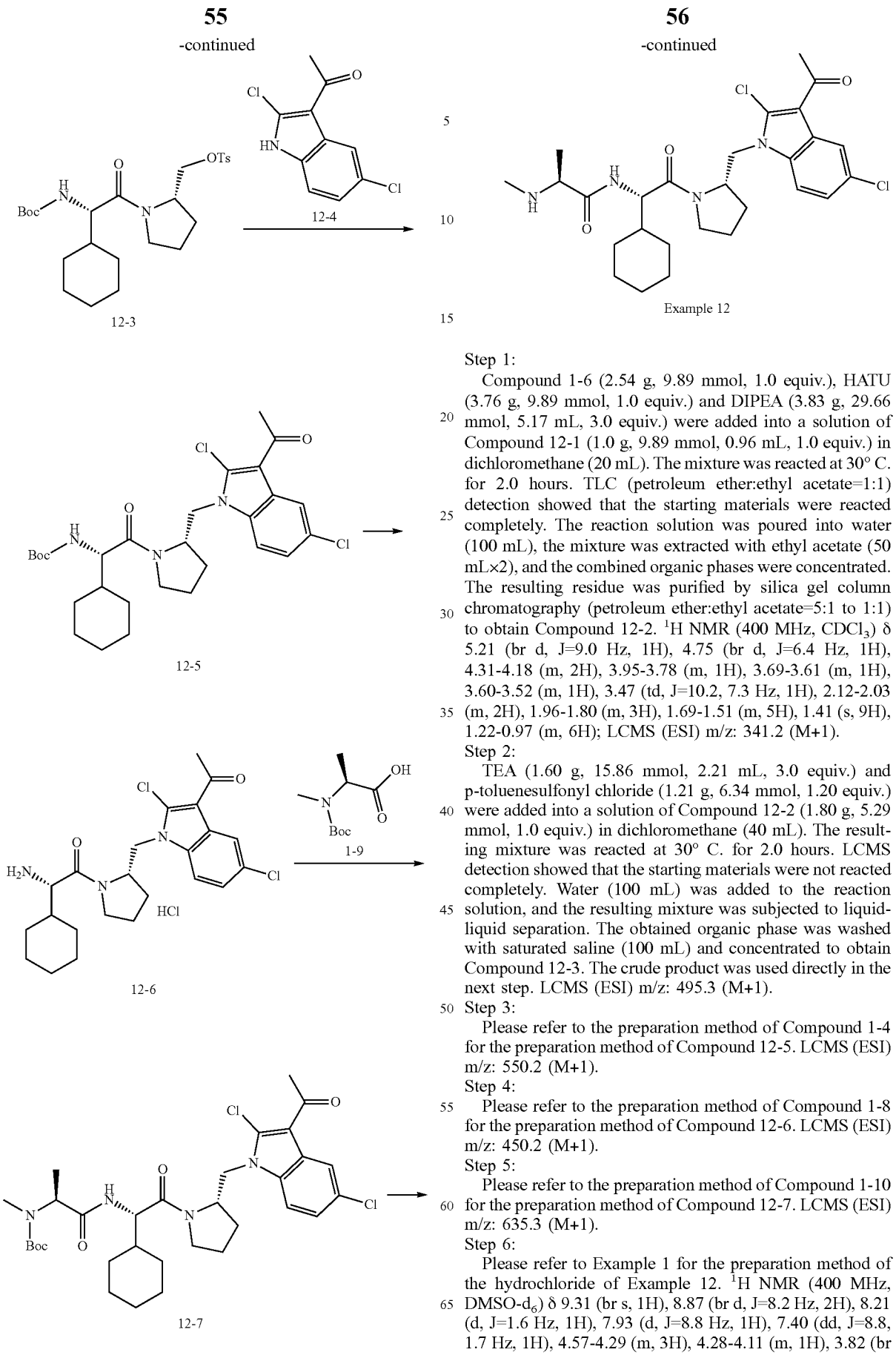

Example 12

Step 1:
Compound 1-6 (2.54 g, 9.89 mmol, 1.0 equiv.), HATU (3.76 g, 9.89 mmol, 1.0 equiv.) and DIPEA (3.83 g, 29.66 mmol, 5.17 mL, 3.0 equiv.) were added into a solution of Compound 12-1 (1.0 g, 9.89 mmol, 0.96 mL, 1.0 equiv.) in dichloromethane (20 mL). The mixture was reacted at 30° C. for 2.0 hours. TLC (petroleum ether:ethyl acetate=1:1) detection showed that the starting materials were reacted completely. The reaction solution was poured into water (100 mL), the mixture was extracted with ethyl acetate (50 mL×2), and the combined organic phases were concentrated. The resulting residue was purified by silica gel column chromatography (petroleum ether:ethyl acetate=5:1 to 1:1) to obtain Compound 12-2. $^1$H NMR (400 MHz, CDCl$_3$) δ 5.21 (br d, J=9.0 Hz, 1H), 4.75 (br d, J=6.4 Hz, 1H), 4.31-4.18 (m, 2H), 3.95-3.78 (m, 1H), 3.69-3.61 (m, 1H), 3.60-3.52 (m, 1H), 3.47 (td, J=10.2, 7.3 Hz, 1H), 2.12-2.03 (m, 2H), 1.96-1.80 (m, 3H), 1.69-1.51 (m, 5H), 1.41 (s, 9H), 1.22-0.97 (m, 6H); LCMS (ESI) m/z: 341.2 (M+1).

Step 2:
TEA (1.60 g, 15.86 mmol, 2.21 mL, 3.0 equiv.) and p-toluenesulfonyl chloride (1.21 g, 6.34 mmol, 1.20 equiv.) were added into a solution of Compound 12-2 (1.80 g, 5.29 mmol, 1.0 equiv.) in dichloromethane (40 mL). The resulting mixture was reacted at 30° C. for 2.0 hours. LCMS detection showed that the starting materials were not reacted completely. Water (100 mL) was added to the reaction solution, and the resulting mixture was subjected to liquid-liquid separation. The obtained organic phase was washed with saturated saline (100 mL) and concentrated to obtain Compound 12-3. The crude product was used directly in the next step. LCMS (ESI) m/z: 495.3 (M+1).

Step 3:
Please refer to the preparation method of Compound 1-4 for the preparation method of Compound 12-5. LCMS (ESI) m/z: 550.2 (M+1).

Step 4:
Please refer to the preparation method of Compound 1-8 for the preparation method of Compound 12-6. LCMS (ESI) m/z: 450.2 (M+1).

Step 5:
Please refer to the preparation method of Compound 1-10 for the preparation method of Compound 12-7. LCMS (ESI) m/z: 635.3 (M+1).

Step 6:
Please refer to Example 1 for the preparation method of the hydrochloride of Example 12. $^1$H NMR (400 MHz, DMSO-d$_6$) δ 9.31 (br s, 1H), 8.87 (br d, J=8.2 Hz, 2H), 8.21 (d, J=1.6 Hz, 1H), 7.93 (d, J=8.8 Hz, 1H), 7.40 (dd, J=8.8, 1.7 Hz, 1H), 4.57-4.29 (m, 3H), 4.28-4.11 (m, 1H), 3.82 (br s, 2H), 2.60 (s, 3H), 2.11-1.93 (m, 2H), 1.81-1.51 (m, 8H), 1.44-0.90 (m, 12H); LCMS (ESI) m/z: 535.2 (M+1).
Example 13
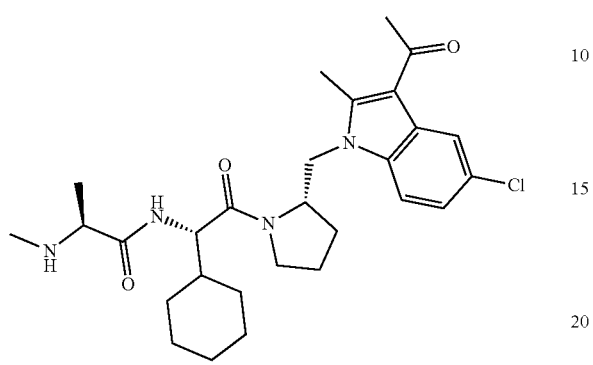
Please refer to Example 1 for the preparation method of the hydrochloride of Example 13. ¹H NMR (400 MHz, DMSO-$d_6$) δ 0.92-1.16 (m, 5H), 1.33 (br d, J=6.72 Hz, 3H), 1.47-1.68 (m, 8H), 1.91 (br d, J=6.48 Hz, 1H), 2.16-2.32 (m, 1H), 2.44 (br t, J=5.01 Hz, 3H), 2.53 (s, 3H), 2.80 (s, 3H), 3.59-3.63 (m, 1H), 3.65-3.72 (m, 1H), 3.85 (br dd, J=11.55, 6.79 Hz, 1H), 4.17-4.45 (m, 4H), 7.23 (dd, J=8.68, 1.59 Hz, 1H), 7.80 (d, J=8.80 Hz, 1H), 8.02 (d, J=1.71 Hz, 1H), 8.73 (br d, J=8.19 Hz, 1H), 8.86 (br s, 1H), 9.45 (br s, 1H); LCMS (ESI) m/z: 515.2 (M+1).
Example 14
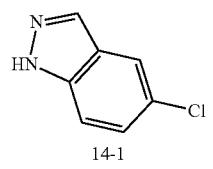
14-1
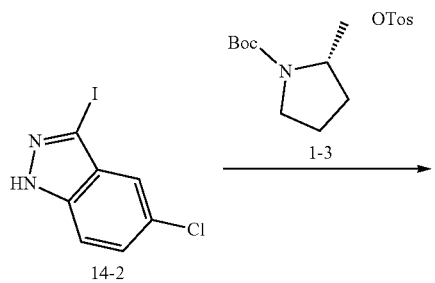
14-2
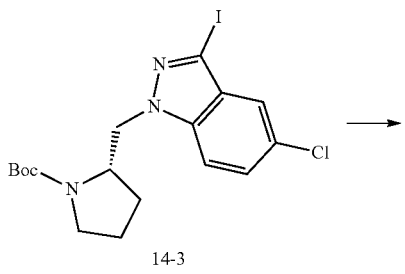
14-3
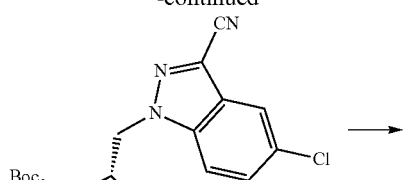
14-4
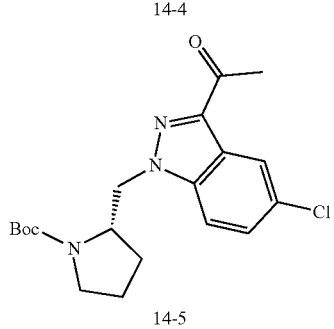
14-5
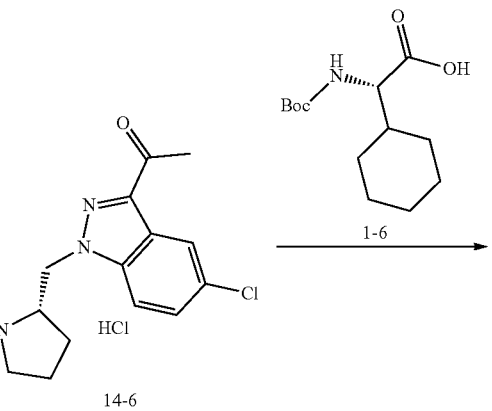
14-6
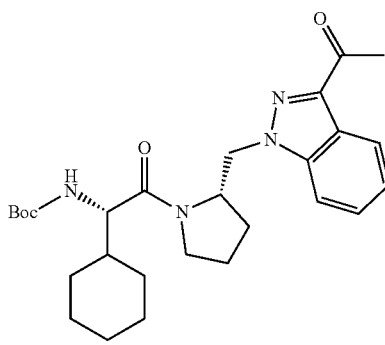
14-7
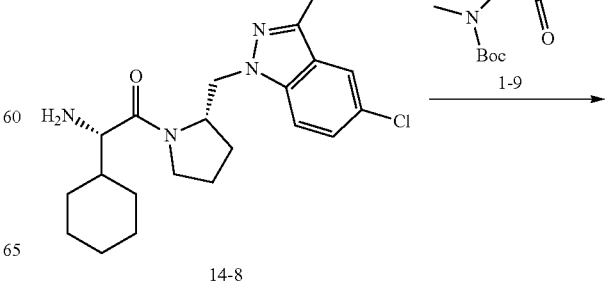
14-8

-continued

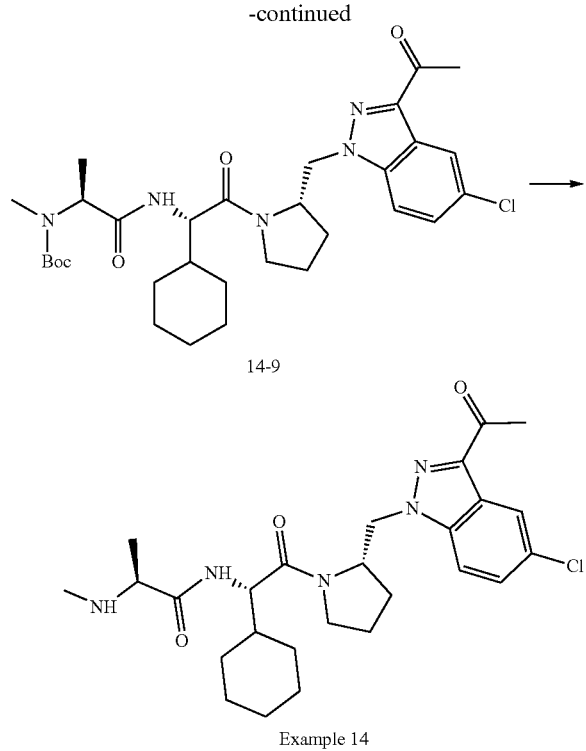

14-9

Example 14

Step 1:

Iodine (13.31 g, 52.43 mmol, 10.56 mL, 2.0 equiv.) and potassium hydroxide (5.88 g, 104.86 mmol, 4 equiv.) were added into a solution of Compound 14-1 (4 g, 26.22 mmol, 1.0 equiv.) in DMA (100 mL) at 0° C. The resulting mixture was reacted at 20° C. for 12 hours. LCMS showed that the reaction was complete. A saturated aqueous sodium sulfite solution (200 mL) was added into the reaction solution, and the resulting mixture was extracted with ethyl acetate (200 mL×2). The combined organic phases were washed with saturated saline (200 mL) and then concentrated. The resulting residue was slurried with petroleum ether (5 mL) to obtain Compound 14-2. $^1$H NMR (400 MHz, DMSO-d$_6$) δ 13.71 (br s, 1H), 7.60 (d, J=8.8 Hz, 1H), 7.47-7.38 (m, 2H).

Step 2:

Please refer to the preparation method of Compound 1-4 for the preparation method of Compound 14-3. $^1$H NMR (400 MHz, DMSO-d$_6$) δ 7.66 (d, J=8.9 Hz, 1H), 7.54-7.41 (m, 2H), 4.56-4.41 (m, 2H), 4.23-4.05 (m, 1H), 3.29-3.01 (m, 2H), 1.93-1.57 (m, 4H), 1.37 (br s, 5H), 1.11 (br s, 4H); LCMS (ESI) m/z: 484.1 (M+23).

Step 3:

Under the protection of nitrogen, zinc cyanide (0.72 g, 6.12 mmol, 0.388 mL, 0.6 equiv.), Pd$_2$(dba)$_3$ (0.93 g, 1.02 mmol, 0.1 equiv.), zinc powder (1.33 g, 20.42 mmol, 2.0 equiv.) and DPPF (1.13 g, 2.04 mmol, 0.2 equiv.) were added into a solution of Compound 14-3 (4.80 g, 10.21 mmol, 1.0 equiv.) in DMF (100 mL). The resulting mixture was heated to 100° C. and reacted for 2 hours. LCMS showed that the reaction was complete. The reaction solution was cooled and then filtered. The filter cake was washed with ethyl acetate (50 mL) and the filtrate was concentrated. The resulting residue was purified by silica gel column chromatography (petroleum ether:ethyl acetate=10:1 to 3:1) to obtain Compound 14-4. LCMS (ESI) m/z: 383.2 (M+23).

Step 4:

Methylmagnesium bromide (3 mol/L, 1.48 mL, 2 equiv.) was added into a solution of Compound 14-4 (0.8 g, 2.22 mmol, 1 equiv.) in tetrahydrofuran (20 mL) at 0° C., and the resulting mixture was reacted at 20° C. for 2 hours. LCMS showed that the reaction was complete. The reaction solution was slowly poured into water (100 mL), and the mixture was extracted with ethyl acetate (50 mL×2). The combined organic phases were washed with saturated saline (100 mL), then the resulting mixture was subjected to liquid-liquid separation, and the organic phase was concentrated to obtain Compound 14-5. The crude product was used directly in the next step. LCMS (ESI) m/z: 378.1 (M+1).

Step 5:

Please refer to the preparation method of Compound 1-5 for the preparation method of Compound 14-6. LCMS (ESI) m/z: 278.1 (M+1).

Step 6:

Please refer to the preparation method of Compound 1-7 for the preparation method of Compound 14-7. LCMS (ESI) m/z: 539.4 (M+23).

Step 7:

Please refer to the preparation method of Compound 1-8 for the preparation method of Compound 14-8. LCMS (ESI) m/z: 417.1 (M+1).

Step 8:

Please refer to the preparation method of Compound 1-10 for the preparation method of Compound 14-9. LCMS (ESI) m/z: 624.3 (M+23).

Step 9:

Please refer to Example 1 for the preparation method of Example 14. $^1$H NMR (400 MHz, DMSO-d$_6$) δ 9.06-8.79 (m, 2H), 8.70 (br d, J=8.2 Hz, 1H), 8.17-8.10 (m, 1H), 7.97 (br d, J=8.9 Hz, 1H), 7.56 (br d, J=8.7 Hz, 1H), 4.71 (br dd, J=13.2, 3.8 Hz, 1H), 4.58-4.44 (m, 2H), 4.38 (br t, J=7.6 Hz, 1H), 3.85 (br d, J=5.1 Hz, 2H), 2.62 (s, 3H), 1.92-1.74 (m, 5H), 1.72-1.49 (m, 8H), 1.31 (br d, J=6.7 Hz, 3H), 1.13 (br d, J=13.7 Hz, 4H), 1.04-0.91 (m, 2H); LCMS (ESI) m/z: 502.1 (M+1).

Example 15

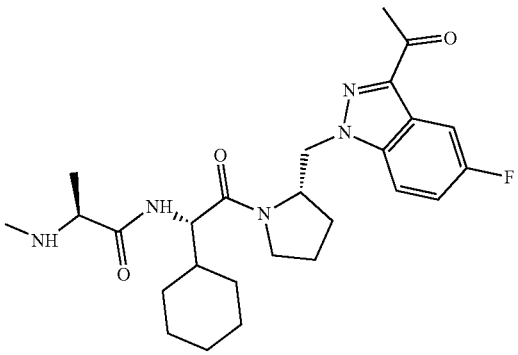 [SMILES: CN[C@@H](C)C(=O)N[C@H](C(=O)N1CCC[C@H]1Cn1nc(C(C)=O)c2cc(F)ccc21)C1CCCCC1]

Please refer to Example 14 for the preparation method of Example 15. $^1$H NMR (400 MHz, DMSO-d$_6$) δ 9.56 (br s, 1H), 8.87 (br s, 1H), 8.80-8.60 (m, 1H), 8.14-7.94 (m, 1H), 7.85-7.68 (m, 1H), 7.58-7.40 (m, 1H), 4.78-4.30 (m, 4H), 3.96-3.74 (m, 1H), 3.64-3.58 (m, 2H), 2.61 (s, 1H), 2.47-2.38 (m, 3H), 1.94-1.52 (m, 11H), 1.39-1.26 (m, 3H), 1.24-0.87 (m, 6H); LCMS (ESI) m/z: 486.3 (M+1).

Example 16

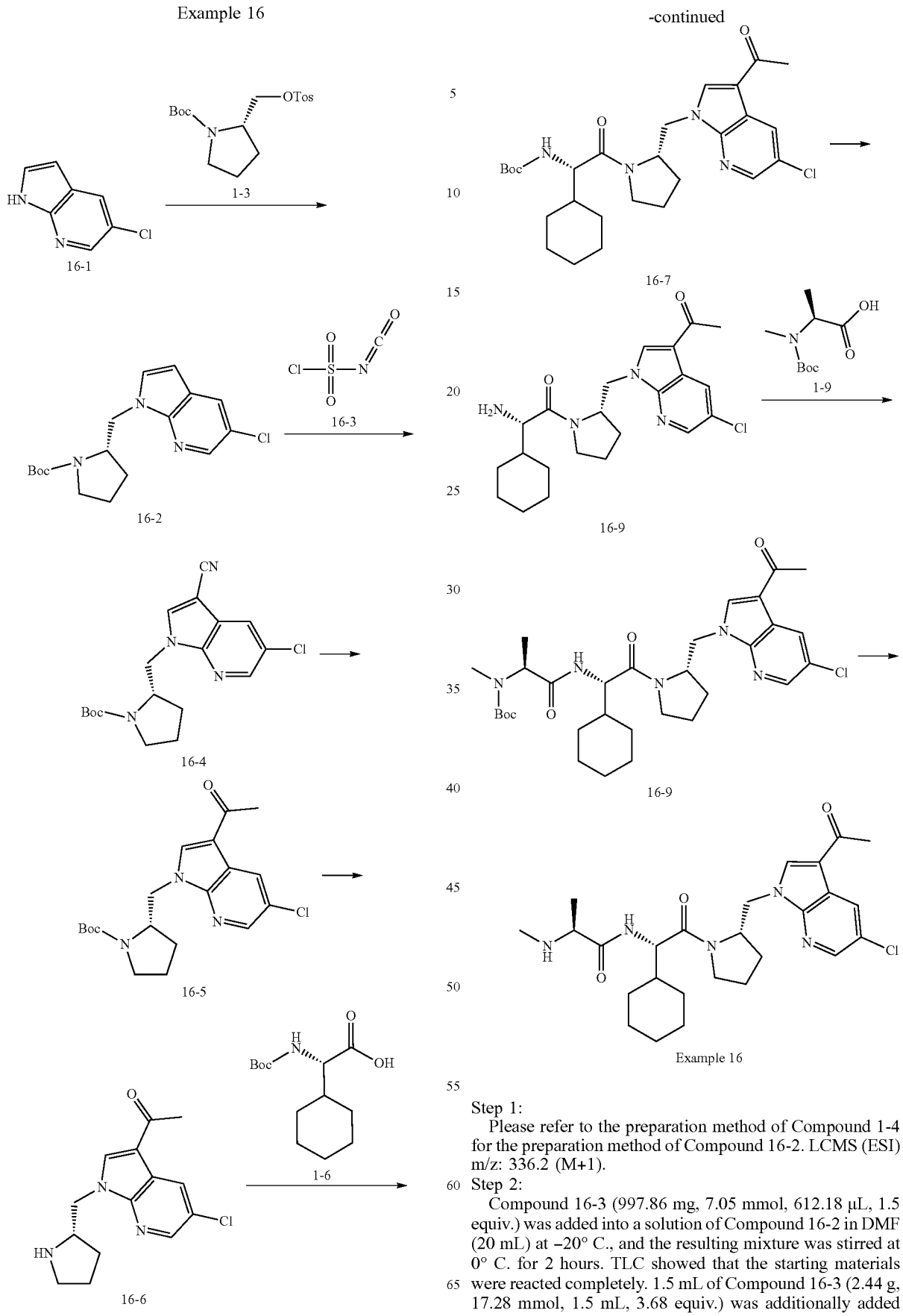

Example 16

Step 1:
Please refer to the preparation method of Compound 1-4 for the preparation method of Compound 16-2. LCMS (ESI) m/z: 336.2 (M+1).

Step 2:
Compound 16-3 (997.86 mg, 7.05 mmol, 612.18 μL, 1.5 equiv.) was added into a solution of Compound 16-2 in DMF (20 mL) at −20° C., and the resulting mixture was stirred at 0° C. for 2 hours. TLC showed that the starting materials were reacted completely. 1.5 mL of Compound 16-3 (2.44 g, 17.28 mmol, 1.5 mL, 3.68 equiv.) was additionally added into the above reaction solution at −20° C., and the resulting mixture was stirred at 0° C. for 0.5 hour. LCMS showed that the starting materials were reacted completely. Water (50 mL) was added into the reaction mixture, and the resulting mixture was filtered. The filter cake was washed with water (20 mL×2) and then dried in vacuum. The resulting residue was purified by silica gel column chromatography (petroleum ether:ethyl acetate=50:1 to 10:1) to obtain Compound 16-3. $^1$H NMR (400 MHz, DMSO-d$_6$) δ 0.98 (br s, 5H), 1.14-1.31 (m, 4H), 1.80 (br d, J=17.85 Hz, 4H), 3.17-3.31 (m, 2H), 4.12-4.30 (m, 2H), 4.35-4.44 (m, 1H), 8.24-8.39 (m, 1H), 8.42-8.57 (m, 2H); LCMS (ESI) m/z: 361.1 (M+1).

Step 3:
Please refer to the preparation method of Compound 14-5 for the preparation method of Compound 16-5. LCMS (ESI) m/z: 378.2 (M+1).

Step 4:
Please refer to the preparation method of Compound 1-5 for the preparation method of Compound 16-6. LCMS (ESI) m/z: 278.0 (M+1).

Step 5:
Please refer to the preparation method of Compound 1-7 for the preparation method of Compound 16-7. LCMS (ESI) m/z: 539.4 (M+23).

Step 6:
Please refer to the preparation method of Compound 1-8 for the preparation method of Compound 16-8. LCMS (ESI) m/z: 417.3 (M+1).

Step 7:
Please refer to the preparation method of Compound 1-10 for the preparation method of Compound 16-9. LCMS (ESI) m/z: 624.1 (M+23).

Step 8:
Please refer to Example 1 for the preparation method of Example 16. $^1$H NMR (400 MHz, DMSO-d$_6$) δ 1.02-1.14 (m, 6H), 1.35-1.49 (m, 2H), 1.58 (br s, 4H), 1.66-1.80 (m, 4H), 1.87 (br d, J=6.72 Hz, 2H), 2.09-2.20 (m, 3H), 2.46 (s, 3H), 2.93 (dt, J=13.57, 6.79 Hz, 1H), 3.54 (br d, J=9.90 Hz, 2H), 3.62-3.70 (m, 1H), 4.21-4.41 (m, 2H), 4.48 (br dd, J=13.51, 7.03 Hz, 1H), 4.68 (br d, J=3.18 Hz, 1H), 7.80 (br d, J=8.80 Hz, 1H), 8.32-8.40 (m, 1H), 8.40-8.47 (m, 1H), 8.55-8.66 (m, 1H); LCMS (ESI) m/z: 502.1 (M+1).

Example 17

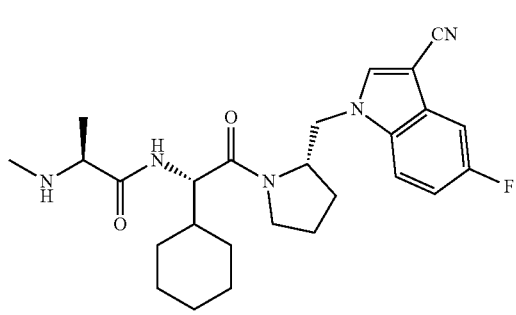 [SMILES: CN[C@@H](C)C(=O)N[C@H](C(=O)N1CCC[C@H]1Cn1cc(C#N)c2cc(F)ccc21)C1CCCCC1]

Please refer to Example 16 and Example 1 for the preparation method of Example 17. $^1$H NMR (400 MHz, CD$_3$OD) δ 8.53 (br d, J=7.6 Hz, 1H), 8.06 (s, 1H), 7.88 (dd, J=8.9, 4.2 Hz, 1H), 7.32 (dd, J=8.8, 2.3 Hz, 1H), 7.14 (dt, J=9.1, 2.3 Hz, 1H), 4.57-4.45 (m, 3H), 4.21-4.08 (m, 1H), 3.92 (q, J=6.8 Hz, 1H), 3.86-3.78 (m, 1H), 3.76-3.65 (m, 1H), 2.67 (s, 3H), 2.22-2.07 (m, 1H), 2.04-1.96 (m, 1H), 1.83-1.63 (m, 8H), 1.50 (d, J=6.8 Hz, 3H), 1.3-1.02 (m, 6H); LCMS (ESI) m/z: 468.2 (M+1).

Example 18

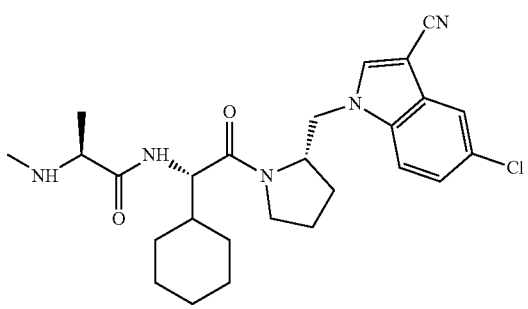 [SMILES: CN[C@@H](C)C(=O)N[C@H](C(=O)N1CCC[C@H]1Cn1cc(C#N)c2cc(Cl)ccc21)C1CCCCC1]

Please refer to Example 16 and Example 1 for the preparation method of Example 18. $^1$H NMR (400 MHz, DMSO-d$_6$) δ 9.60-9.41 (m, 1H), 8.86 (br d, J=4.6 Hz, 1H), 8.69 (d, J=8.3 Hz, 1H), 8.37 (s, 1H), 7.94 (d, J=8.8 Hz, 1H), 7.66 (d, J=1.8 Hz, 1H), 7.39 (dd, J=8.8, 2.0 Hz, 1H), 4.41 (br d, J=2.8 Hz, 1H), 4.38 (br d, J=6.5 Hz, 1H), 4.23-4.12 (m, 1H), 3.88-3.79 (m, 1H), 3.70-3.53 (m, 2H), 2.44 (br t, J=5.1 Hz, 3H), 2.15-2.01 (m, 1H), 1.90 (br d, J=4.3 Hz, 1H), 1.75-1.52 (m, 8H), 1.32 (d, J=6.8 Hz, 3H), 1.25-0.89 (m, 6H); LCMS (ESI) m/z: 484.4 (M+1).

Example 19

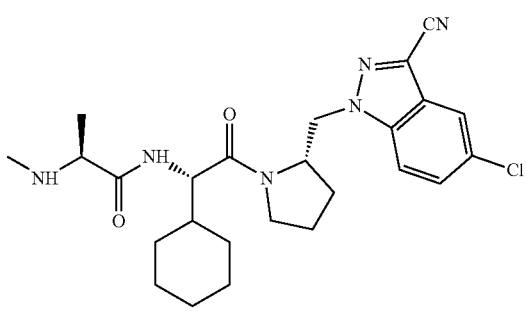 [SMILES: CN[C@@H](C)C(=O)N[C@H](C(=O)N1CCC[C@H]1Cn1nc(C#N)c2cc(Cl)ccc21)C1CCCCC1]

Please refer to Example 14 for the preparation method of Example 19. $^1$H NMR (400 MHz, CD$_3$OD) δ 7.93 (d, J=9.0 Hz, 1H), 7.83 (d, J=1.1 Hz, 1H), 7.54 (dd, J=8.9, 1.5 Hz, 1H), 4.77-4.70 (m, 1H), 4.68-4.61 (m, 1H), 4.57 (br s, 1H), 4.48 (br d, J=7.0 Hz, 1H), 3.88 (q, J=7.0 Hz, 1H), 3.84-3.74 (m, 1H), 3.65-3.54 (m, 1H), 2.68-2.62 (m, 3H), 1.97-1.85 (m, 3H), 1.83-1.66 (m, 7H), 1.47 (d, J=7.0 Hz, 3H), 1.37-1.00 (m, 5H); LCMS (ESI) m/z: 485.1 (M+1).

Example 20

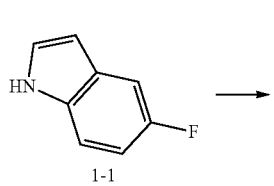

-continued

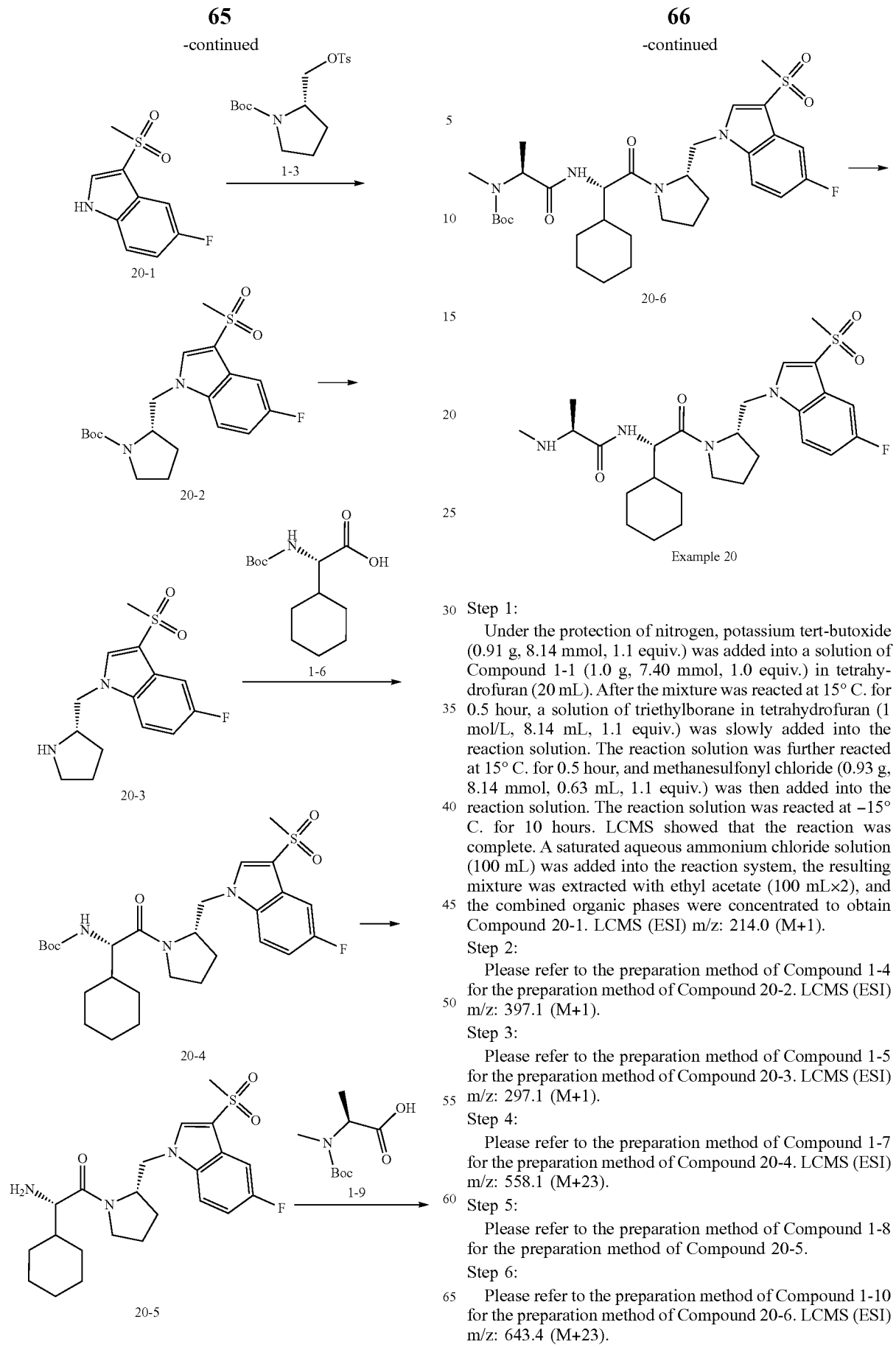

Example 20

Step 1:
Under the protection of nitrogen, potassium tert-butoxide (0.91 g, 8.14 mmol, 1.1 equiv.) was added into a solution of Compound 1-1 (1.0 g, 7.40 mmol, 1.0 equiv.) in tetrahydrofuran (20 mL). After the mixture was reacted at 15° C. for 0.5 hour, a solution of triethylborane in tetrahydrofuran (1 mol/L, 8.14 mL, 1.1 equiv.) was slowly added into the reaction solution. The reaction solution was further reacted at 15° C. for 0.5 hour, and methanesulfonyl chloride (0.93 g, 8.14 mmol, 0.63 mL, 1.1 equiv.) was then added into the reaction solution. The reaction solution was reacted at −15° C. for 10 hours. LCMS showed that the reaction was complete. A saturated aqueous ammonium chloride solution (100 mL) was added into the reaction system, the resulting mixture was extracted with ethyl acetate (100 mL×2), and the combined organic phases were concentrated to obtain Compound 20-1. LCMS (ESI) m/z: 214.0 (M+1).

Step 2:
Please refer to the preparation method of Compound 1-4 for the preparation method of Compound 20-2. LCMS (ESI) m/z: 397.1 (M+1).

Step 3:
Please refer to the preparation method of Compound 1-5 for the preparation method of Compound 20-3. LCMS (ESI) m/z: 297.1 (M+1).

Step 4:
Please refer to the preparation method of Compound 1-7 for the preparation method of Compound 20-4. LCMS (ESI) m/z: 558.1 (M+23).

Step 5:
Please refer to the preparation method of Compound 1-8 for the preparation method of Compound 20-5.

Step 6:
Please refer to the preparation method of Compound 1-10 for the preparation method of Compound 20-6. LCMS (ESI) m/z: 643.4 (M+23).

Step 7:

Please refer to Example 1 for the preparation method of Example 20. $^1$H NMR (400 MHz, DMSO-d$_6$) δ 9.61-9.37 (m, 1H), 8.96-8.83 (m, 1H), 8.79 (d, J=8.2 Hz, 1H), 8.23-8.19 (m, 1H), 7.98 (dd, J=9.2, 4.4 Hz, 1H), 7.52 (dd, J=9.4, 2.5 Hz, 1H), 7.26 (dt, J=9.2, 2.5 Hz, 1H), 4.51-4.32 (m, 3H), 4.15 (dd, J=13.2, 8.6 Hz, 1H), 3.98-3.79 (m, 1H), 3.20 (s, 3H), 2.46 (t, J=5.3 Hz, 3H), 2.08 (td, J=12.2, 8.7 Hz, 1H), 1.95-1.82 (m, 1H), 1.77-1.49 (m, 9H), 1.37-1.30 (m, 3H), 1.26-0.91 (m, 6H); LCMS (ESI) m/z: 521.3 (M+1).

Example 21

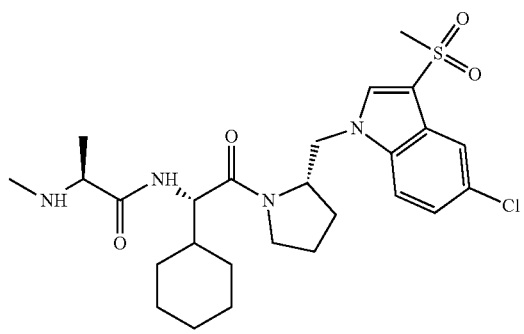 [SMILES: CN[C@@H](C)C(=O)N[C@H](C(=O)N1CCC[C@H]1Cn1cc(S(C)(=O)=O)c2cc(Cl)ccc21)C1CCCCC1]

Please refer to Example 20 for the preparation method of Example 21. $^1$H NMR (400 MHz, CD$_3$OD) δ 8.03 (s, 1H), 7.91-7.80 (m, 2H), 7.32 (dd, J=8.7, 1.9 Hz, 1H), 4.59-4.43 (m, 2H), 4.21-4.10 (m, 1H), 3.94 (q, J=6.8 Hz, 1H), 3.82 (q, J=8.5 Hz, 1H), 3.74-3.63 (m, 1H), 3.18 (s, 3H), 2.67 (s, 3H), 2.16-2.02 (m, 1H), 2.01-1.94 (m, 1H), 1.85-1.72 (m, 6H), 1.71-1.59 (m, 2H), 1.50 (d, J=7.0 Hz, 3H), 1.34-1.01 (m, 6H); LCMS (ESI) m/z: 537.1 (M+1).

Example 22

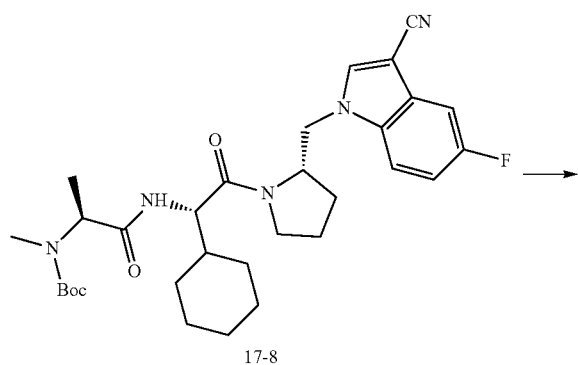

17-8

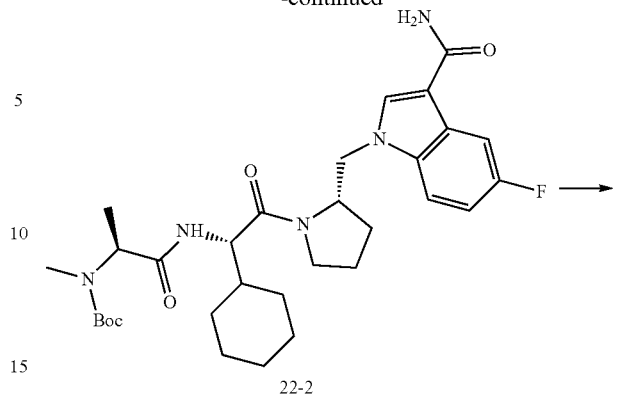

22-2

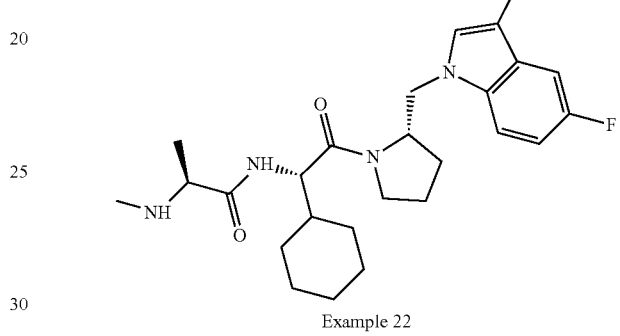

Example 22

Step 1:

Potassium carbonate (85.21 mg, 616.53 μmol, 2.0 equiv.) and hydrogen peroxide (9.44 g, 83.26 mmol, 8 mL, concentration: 30%, 270.09 equiv.) were added into a solution of Compound 17-8 (175 mg, 308.27 μmol, 1.0 equiv.) in ethanol (8 mL), and the resulting reaction solution was reacted at 50° C. for 1 hour. LCMS showed that the reaction was complete. Water (40 mL) was added into the reaction solution, and the resulting mixture was extracted with ethyl acetate (30 mL). The combined organic phases were washed with saturated saline (20 mL), dried over anhydrous sodium sulfate, and then filtered. The filtrate was concentrated under reduced pressure to obtain Compound 22-2. LCMS (ESI) m/z: 586.6 (M+1).

Step 2:

Please refer to Example 1 for the preparation method of Example 22. $^1$H NMR (400 MHz, DMSO-d$_6$) δ 9.48 (br s, 1H), 8.88 (br s, 1H), 8.81 (br d, J=7.9 Hz, 1H), 8.16 (s, 1H), 7.87-7.78 (m, 2H), 7.13-7.06 (m, 1H), 4.44-4.36 (m, 2H), 4.32 (br d, J=4.1 Hz, 1H), 4.03 (br dd, J=13.5, 9.6 Hz, 1H), 3.86 (br d, J=4.9 Hz, 2H), 3.63-3.53 (m, 1H), 2.44 (br s, 1H), 2.15-2.02 (m, 1H), 1.91 (br s, 1H), 1.77-1.58 (m, 9H), 1.35 (br d, J=6.8 Hz, 3H), 1.21-0.99 (m, 6H); LCMS (ESI) m/z: 486.5 (M+1).

Example 23

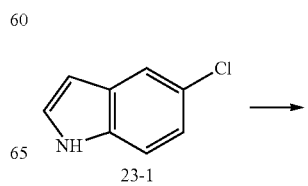

23-1

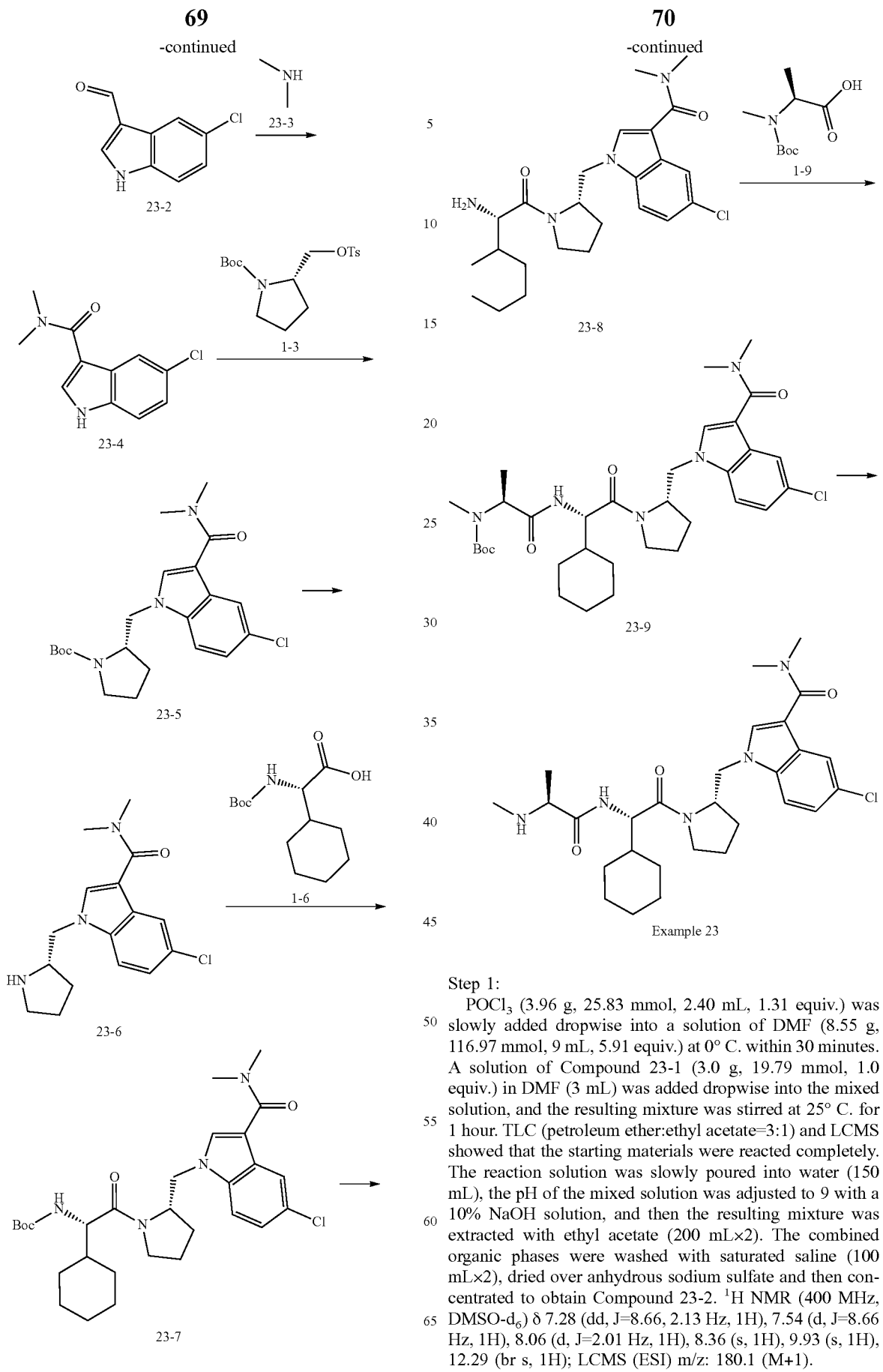

Step 1:

POCl$_3$ (3.96 g, 25.83 mmol, 2.40 mL, 1.31 equiv.) was slowly added dropwise into a solution of DMF (8.55 g, 116.97 mmol, 9 mL, 5.91 equiv.) at 0° C. within 30 minutes. A solution of Compound 23-1 (3.0 g, 19.79 mmol, 1.0 equiv.) in DMF (3 mL) was added dropwise into the mixed solution, and the resulting mixture was stirred at 25° C. for 1 hour. TLC (petroleum ether:ethyl acetate=3:1) and LCMS showed that the starting materials were reacted completely. The reaction solution was slowly poured into water (150 mL), the pH of the mixed solution was adjusted to 9 with a 10% NaOH solution, and then the resulting mixture was extracted with ethyl acetate (200 mL×2). The combined organic phases were washed with saturated saline (100 mL×2), dried over anhydrous sodium sulfate and then concentrated to obtain Compound 23-2. $^1$H NMR (400 MHz, DMSO-d$_6$) δ 7.28 (dd, J=8.66, 2.13 Hz, 1H), 7.54 (d, J=8.66 Hz, 1H), 8.06 (d, J=2.01 Hz, 1H), 8.36 (s, 1H), 9.93 (s, 1H), 12.29 (br s, 1H); LCMS (ESI) m/z: 180.1 (M+1).

Step 2:

Compound 23-3 (2 mol/L, 33.41 mL, 4.0 equiv.) was added into a solution of Compound 23-2 (3 g, 16.70 mmol, 1.0 equiv.) and sodium cyanide (163.72 mg, 3.34 mmol, 0.2 equiv.) in DMF (30 mL), and the resulting mixture was stirred at 30° C. for 10 minutes. Manganese dioxide (36.30 g, 417.59 mmol, 25.0 equiv.) was added in portions into the mixture, and the resulting mixture was further stirred at 30° C. for 14 hours. LCMS showed that the starting materials were reacted completely. The reaction mixture was filtered, and the filter cake was washed with ethyl acetate (100 mL×2). The combined organic phases were successively washed with a saturated ferrous sulfate solution (50 mL×2) and saline (100 mL), dried over anhydrous sodium sulfate and then concentrated to obtain Compound 23-4. The crude product was used directly in the next step. LCMS (ESI) m/z: 223.2 (M+1).

Step 3:

Please refer to the preparation method of Compound 1-4 for the preparation method of Compound 23-5. LCMS (ESI) m/z: 406.0 (M+1).

Step 4:

Please refer to the preparation method of Compound 1-5 for the preparation method of Compound 23-6. $^1$H NMR (400 MHz, DMSO-$d_6$) δ 1.62-1.77 (m, 1H), 1.80-1.92 (m, 1H), 1.94-2.04 (m, 1H), 2.06-2.17 (m, 1H), 3.04-3.15 (m, 6H) 3.20-3.31 (m, 1H), 3.86 (br s, 1H), 4.52-4.56 (m, 1H), 4.61 (br dd, J=14.87, 5.08 Hz, 2H), 4.69-4.77 (m, 1H), 4.69-4.77 (m, 1H), 7.26 (dd, J=8.72, 2.07 Hz, 1H), 7.79 (d, J=8.78 Hz, 1H), 7.90 (d, J=2.01 Hz, 1H), 8.26 (s, 1H), 9.35 (br s, 1H), 10.04 (br s, 1H); LCMS (ESI) m/z: 306.1 (M+1).

Step 5:

Please refer to the preparation method of Compound 1-7 for the preparation method of Compound 23-7. LCMS (ESI) m/z: 545.4 (M+1)

Step 6:

Please refer to the preparation method of Compound 1-8 for the preparation method of Compound 23-8. LCMS (ESI) m/z: 445.0 (M+1).

Step 7:

Please refer to the preparation method of Compound 1-10 for the preparation method of Compound 23-9. LCMS (ESI) m/z: 630.3 (M+1).

Step 8:

Please refer to Example 1 for the preparation method of Example 23. $^1$H NMR (400 MHz, CD$_3$OD) δ 1.00-1.30 (m, 5H), 1.47-1.54 (m, 3H), 1.61 (br d, J=12.23 Hz, 1H), 1.65-1.87 (m, 7H), 1.99 (br s, 1H), 2.06-2.23 (m, 1H), 2.64-2.71 (m, 3H), 3.1-3.30 (m, 6H), 3.72 (br d, J=6.48 Hz, 1H), 3.83 (q, J=8.48 Hz, 1H), 3.90-4.02 (m, 1H), 4.09-4.20 (m, 1H), 4.46 (br d, J=7.46 Hz, 1H), 4.51-4.62 (m, 2H), 7.24-7.30 (m, 1H), 7.74 (s, 1H), 7.80 (d, J=9.05 Hz, 1H), 7.92 (br s, 1H); LCMS (ESI) m/z: 530.3 (M+1).

Example 24

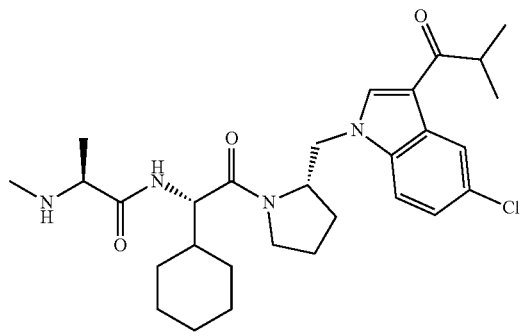 [SMILES: CN[C@@H](C)C(=O)N[C@H](C(=O)N1CCC[C@H]1Cn1cc(C(=O)C(C)C)c2cc(Cl)ccc21)C1CCCCC1]

Please refer to Example 1 for the preparation method of Example 24. $^1$H NMR (400 MHz, CD$_3$OD) δ 8.36-8.23 (m, 2H), 7.79 (d, J=8.8 Hz, 1H), 7.27 (dd, J=8.8, 2.0 Hz, 1H), 4.60-4.44 (m, 3H), 4.21-4.05 (m, 1H), 3.97-3.77 (m, 2H), 3.71 (qd, J=10.0, 4.0 Hz, 1H), 3.44 (spt, J=6.8 Hz, 1H), 2.67 (s, 3H), 2.23-2.07 (m, 1H), 2.06-1.96 (m, 1H), 1.85-1.64 (m, 8H), 1.50 (d, J=7.1 Hz, 3H), 1.27-1.05 (m, 10H); LCMS (ESI) m/z: 551.3 (M+23).

Example 25

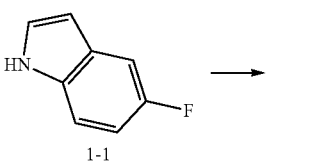

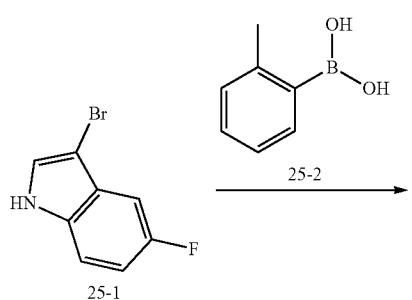

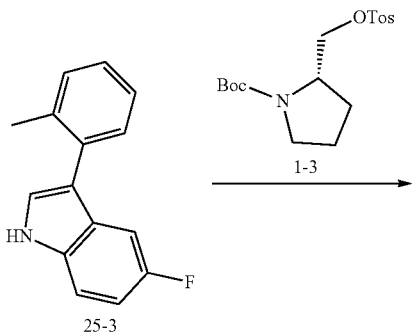

-continued

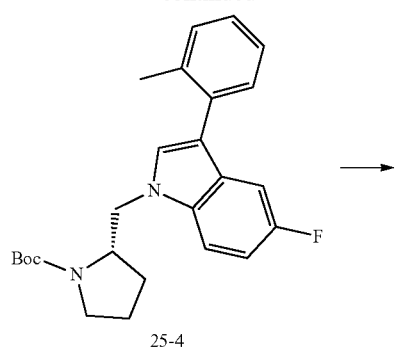
25-4

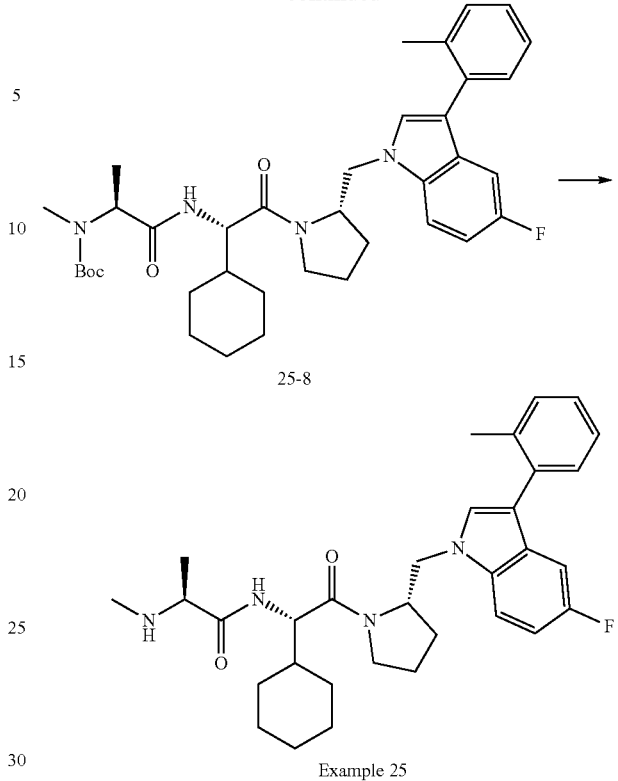
25-8

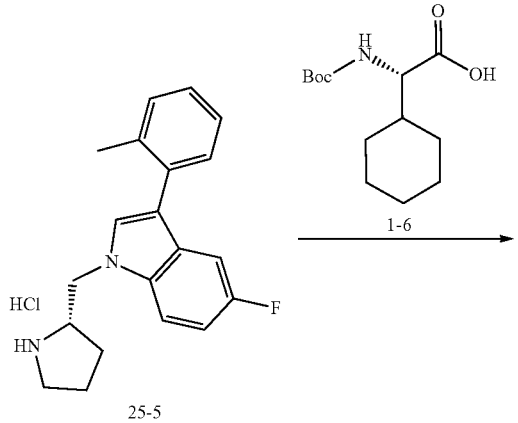
25-5

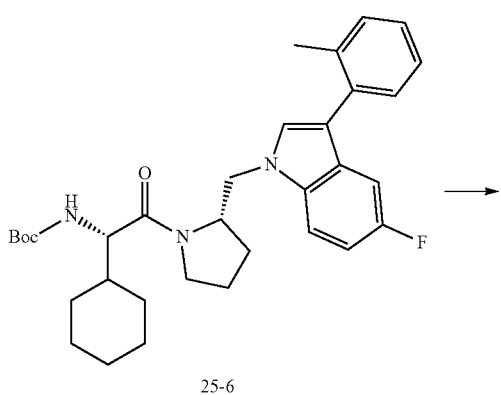
25-6

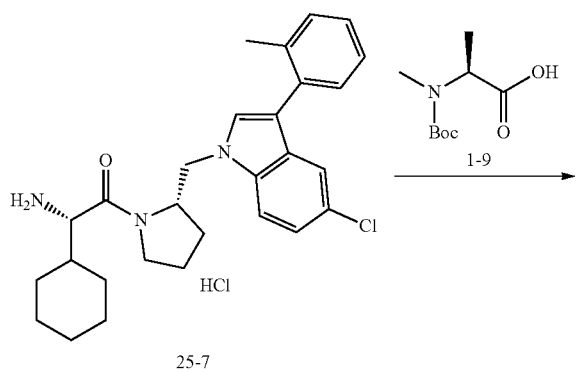
25-7

-continued

Example 25

Step 1:

NBS (276.58 mg, 1.55 mmol, 1.05 equiv.) was added in portions into a solution of Compound 1-1 (0.2 g, 1.48 mmol, 1.0 equiv.) in DMF (2 mL), and the resulting mixture was stirred at 15° C. for 1 hour. TLC (petroleum ether:ethyl acetate=3:1) showed that the starting materials were reacted completely, and LCMS showed that a product was formed. A saturated sodium sulfite solution (2 mL) was added into the reaction solution, and the mixture was extracted with ethyl acetate (2 mL×3). The combined organic phases were concentrated to obtain Compound 25-1, and the crude product was directly used in the next step. LCMS (ESI) m/z: 211.9 (M-1).

Step 2:

Under the protection of nitrogen, Compound 25-2 (1.91 g, 14.02 mmol, 2.0 equiv.), potassium phosphate (2.98 g, 14.02 mmol, 2.0 equiv.) and Pd(dppf)Cl$_2$ (512.80 mg, 700.82 μmol, 0.1 equiv.) were added into a mixed solution of Compound 25-1 (1.5 g, 7.01 mmol, 1.0 equiv.) in tetrahydrofuran (18 mL) and water (3.0 mL), and the resulting mixture was heated to 80° C. and stirred for 16 hours. LCMS showed that the starting materials were reacted completely. The reaction solution was dried over anhydrous sodium sulfate and then filtered, and the filtrate was concentrated under reduced pressure. The resulting residue was purified by silica gel column chromatography (petroleum ether:ethyl acetate=1:0 to 5:1) to obtain Compound 25-3. $^1$H NMR (400 MHz, DMSO-d$_6$) δ 8.07-7.86 (m, 1H), 7.52 (d, J=2.4 Hz, 1H), 7.46-7.40 (m, 1H), 7.37-7.30 (m, 1H), 7.26-7.21 (m, 2H), 7.13-7.05 (m, 2H), 6.99 (dt, J=9.1, 2.3, 1H), 2.29 (s, 3H); LCMS (ESI) m/z: 224.0 (M-1).

Step 3:

Please refer to the preparation method of Compound 1-4 for the preparation method of Compound 25-4. $^1$H NMR (400 MHz, CDCl$_3$) δ 7.43-7.24 (m, 5H), 7.22-7.13 (m, 1H), 7.13-7.07 (m, 1H), 7.05-6.97 (m, 1H), 4.49-4.36 (m, 1H), 4.31-4.24 (m, 1H), 3.50-3.33 (m, 1H), 3.26-3.11 (m, 1H), 2.35 (s, 3H), 1.95-1.85 (m, 1H), 1.83-1.71 (m, 2H), 1.59-1.46 (m, 11H); LCMS (ESI) m/z: 431.3 (M+23).

Step 4:

Please refer to the preparation method of Compound 1-5 for the preparation method of Compound 25-5. LCMS (ESI) m/z: 309.2 (M+1).

Step 5:

Please refer to the preparation method of Compound 1-7 for the preparation method of Compound 25-6. LCMS (ESI) m/z: 548.1 (M+1).

Step 6:

Please refer to the preparation method of Compound 1-8 for the preparation method of Compound 25-7. LCMS (ESI) m/z: 448.2 (M+1).

Step 7:

Please refer to the preparation method of Compound 1-10 for the preparation method of Compound 25-8. LCMS (ESI) m/z: 633 (M+1).

Step 8:

Please refer to Example 1 for the preparation method of Example 25. $^1$H NMR (400 MHz, CD$_3$OD) δ 7.70 (dd, J=8.9, 4.1 Hz, 1H), 7.31 (dd, J=4.7, 3.2 Hz, 2H), 7.27 (s, 1H), 7.25-7.19 (m, 2H), 7.03-6.94 (m, 2H), 4.62-4.47 (m, 3H), 4.21-4.07 (m, 1H), 3.97-3.88 (m, 1H), 3.86-3.74 (m, 1H), 3.70-3.59 (m, 1H), 2.68 (s, 3H), 2.28 (s, 3H), 2.09-1.57 (m, 11H), 1.52 (d, J=6.9 Hz, 3H), 1.39-1.02 (m, 6H); LCMS (ESI) m/z: 533.2 (M+1).

Example 26

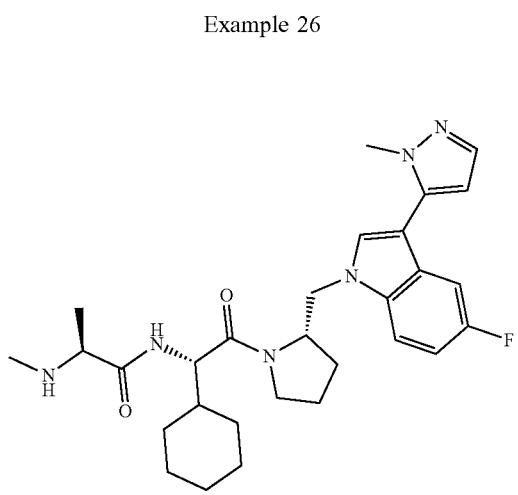

Please refer to Example 25 for the preparation method of Example 26. $^1$H NMR (400 MHz, CD$_3$OD) δ 8.23-8.14 (m, 1H), 8.03-7.93 (m, 1H), 7.88 (dd, J=8.9, 4.3 Hz, 1H), 7.39 (br d, J=9.4 Hz, 1H), 7.12 (dt, J=9.1, 2.4 Hz, 1H), 6.94-6.85 (m, 1H), 4.65-4.56 (m, 2H), 4.48 (d, J=7.5 Hz, 1H), 4.25-4.08 (m, 4H), 4.00-3.91 (m, 1H), 3.90-3.80 (m, 1H), 3.79-3.68 (m, 1H), 2.67 (s, 3H), 2.30-2.13 (m, 1H), 2.05-1.95 (m, 1H), 1.90-1.60 (m, 8H), 1.51 (d, J=7.0 Hz, 3H), 1.38-1.01 (m, 6H); LCMS (ESI) m/z: 523.3 (M+1).

Example 27

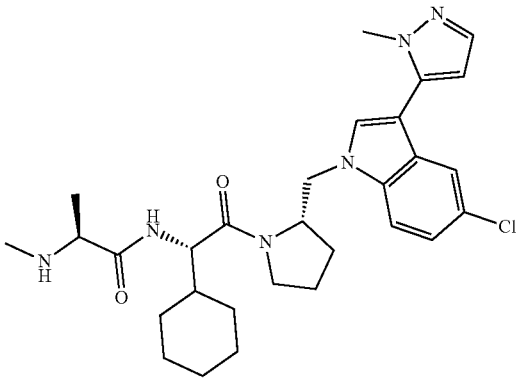 [SMILES: CN[C@@H](C)C(=O)N[C@H](C(=O)N1CCC[C@H]1Cn1cc(-c2ccnn2C)c2cc(Cl)ccc21)C1CCCCC1]

Please refer to Example 25 for the preparation method of Example 27. $^1$H NMR (400 MHz, DMSO-d$_6$) δ 7.83-7.95 (m, 2H), 7.82 (s, 1H), 7.53-7.59 (m, 1H), 7.47-7.53 (m, 1H), 7.29 (dd, J=8.78, 2.01 Hz, 1H), 6.48 (d, J=1.76 Hz, 1H), 4.34-4.53 (m, 3H), 4.10 (dd, J=13.05, 8.03 Hz, 1H), 3.86-3.89 (m, 3H), 3.61 (br d, J=8.03 Hz, 2H), 2.97 (q, J=6.69 Hz, 1H), 2.17 (s, 3H), 1.98-2.07 (m, 1H), 1.78-1.92 (m, 2H), 1.51-1.77 (m, 9H), 1.14 (br s, 1H), 1.09 (d, J=6.78 Hz, 4H), 0.89-1.04 (m, 2H); LCMS (ESI) m/z: 539.3 (M+1).

Example 28

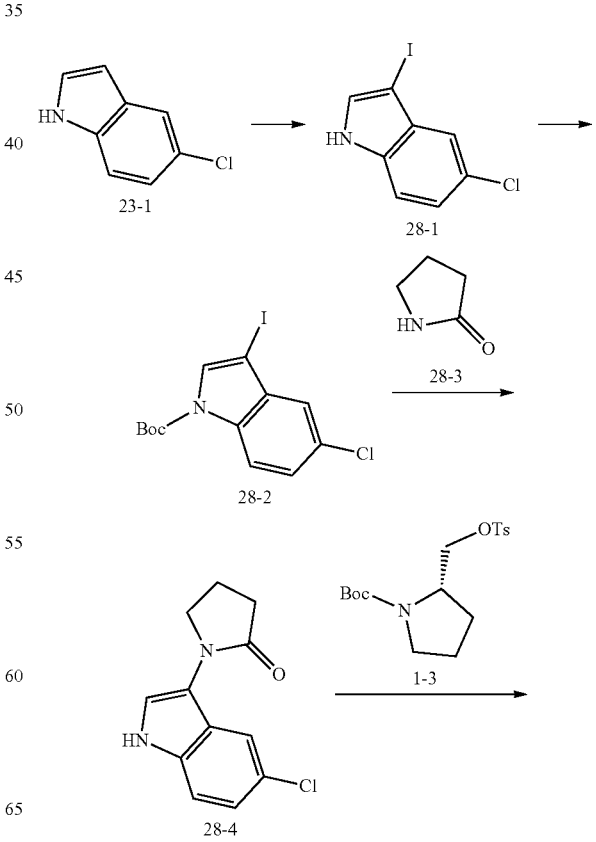

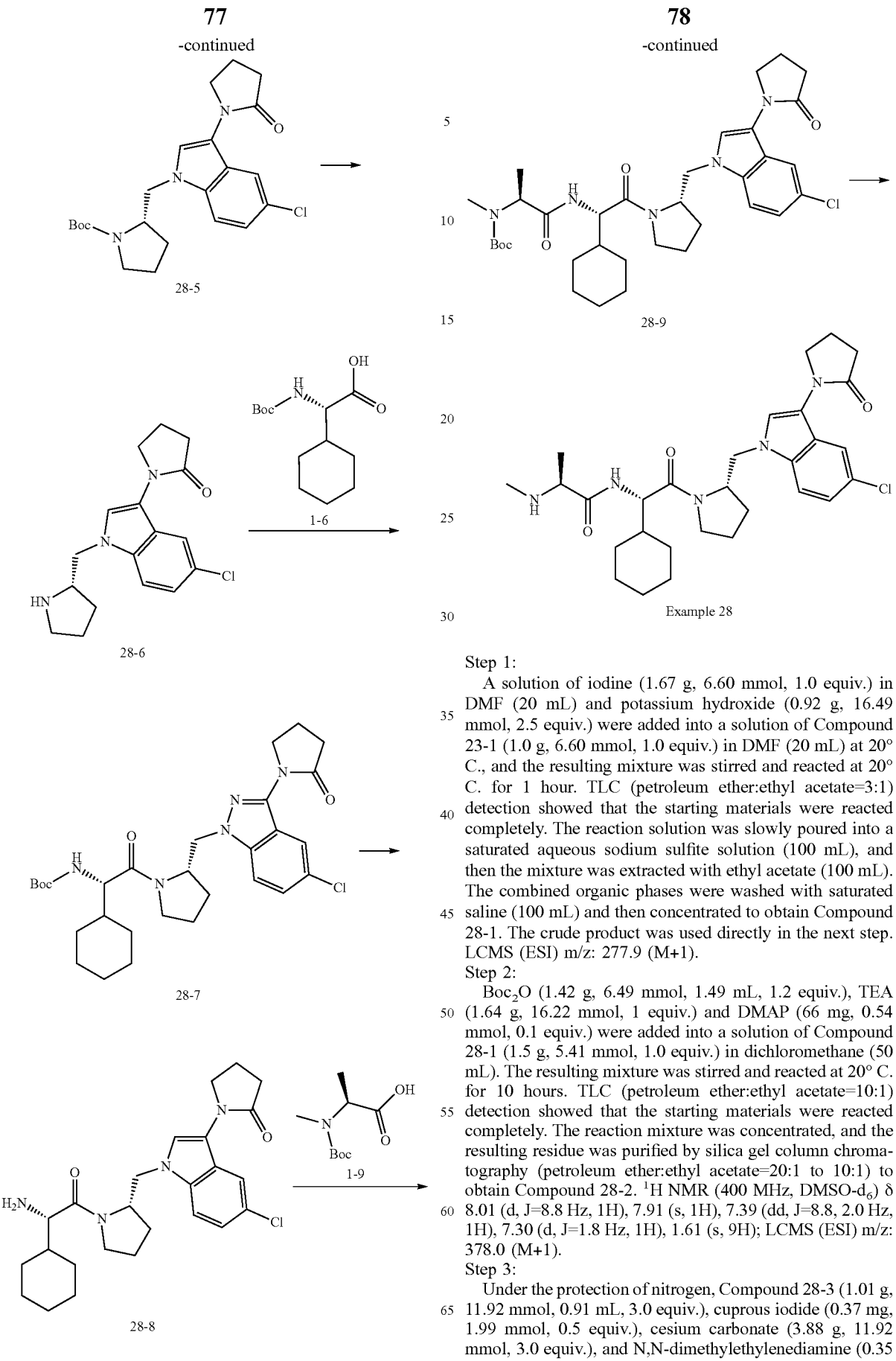

Step 1:
A solution of iodine (1.67 g, 6.60 mmol, 1.0 equiv.) in DMF (20 mL) and potassium hydroxide (0.92 g, 16.49 mmol, 2.5 equiv.) were added into a solution of Compound 23-1 (1.0 g, 6.60 mmol, 1.0 equiv.) in DMF (20 mL) at 20° C., and the resulting mixture was stirred and reacted at 20° C. for 1 hour. TLC (petroleum ether:ethyl acetate=3:1) detection showed that the starting materials were reacted completely. The reaction solution was slowly poured into a saturated aqueous sodium sulfite solution (100 mL), and then the mixture was extracted with ethyl acetate (100 mL). The combined organic phases were washed with saturated saline (100 mL) and then concentrated to obtain Compound 28-1. The crude product was used directly in the next step. LCMS (ESI) m/z: 277.9 (M+1).

Step 2:
$Boc_2O$ (1.42 g, 6.49 mmol, 1.49 mL, 1.2 equiv.), TEA (1.64 g, 16.22 mmol, 1 equiv.) and DMAP (66 mg, 0.54 mmol, 0.1 equiv.) were added into a solution of Compound 28-1 (1.5 g, 5.41 mmol, 1.0 equiv.) in dichloromethane (50 mL). The resulting mixture was stirred and reacted at 20° C. for 10 hours. TLC (petroleum ether:ethyl acetate=10:1) detection showed that the starting materials were reacted completely. The reaction mixture was concentrated, and the resulting residue was purified by silica gel column chromatography (petroleum ether:ethyl acetate=20:1 to 10:1) to obtain Compound 28-2. $^1H$ NMR (400 MHz, DMSO-$d_6$) δ 8.01 (d, J=8.8 Hz, 1H), 7.91 (s, 1H), 7.39 (dd, J=8.8, 2.0 Hz, 1H), 7.30 (d, J=1.8 Hz, 1H), 1.61 (s, 9H); LCMS (ESI) m/z: 378.0 (M+1).

Step 3:
Under the protection of nitrogen, Compound 28-3 (1.01 g, 11.92 mmol, 0.91 mL, 3.0 equiv.), cuprous iodide (0.37 mg, 1.99 mmol, 0.5 equiv.), cesium carbonate (3.88 g, 11.92 mmol, 3.0 equiv.), and N,N-dimethylethylenediamine (0.35 g, 3.97 mmol, 1.0 equiv.) were added into a solution of Compound 28-2 (1.5 g, 3.97 mmol, 1.0 equiv.) in dioxane (40 mL). The reaction solution was heated to 80° C. and reacted for 2.0 hours. LCMS showed that the starting materials were reacted completely. The reaction solution was cooled to 20° C. and filtered. The filter cake was washed with ethyl acetate (50 mL), and the filtrate was concentrated. The resulting residue was purified by silica gel column chromatography (petroleum ether:ethyl acetate=5:1 to 1:1) to obtain Compound 28-4. $^1$H NMR (400 MHz, CDCl$_3$) δ 8.97 (br s, 1H), 7.53 (d, J=1.8 Hz, 1H), 7.19-7.01 (m, 3H), 3.92 (t, J=7.0 Hz, 2H), 2.64 (t, J=8.2 Hz, 2H), 2.32-2.24 (m, 2H); LCMS (ESI) m/z: 234.1 (M+1).

Step 4:

Please refer to the preparation method of Compound 1-4 for the preparation method of Compound 28-5. $^1$H NMR (400 MHz, CDCl$_3$) δ 7.61 (br d, J=6.1 Hz, 1H), 7.48 (br d, J=8.7 Hz, 1H), 7.44-7.38 (m, 1H), 7.32 (br d, J=8.7 Hz, 1H), 7.15 (dd, J=8.8, 1.9 Hz, 1H), 4.22-4.13 (m, 1H), 3.98 (br t, J=7.0 Hz, 2H), 3.45-3.15 (m, 2H), 2.95 (s, 1H), 2.87 (s, 1H), 2.59 (t, J=8.1 Hz, 2H), 2.30-2.16 (m, 2H), 1.93-1.65 (m, 4H), 1.50 (s, 10H); LCMS (ESI) m/z: 418.2 (M+1).

Step 5:

Please refer to the preparation method of Compound 1-5 for the preparation method of Compound 28-6. LCMS (ESI) m/z: 318.1 (M+1).

Step 6:

Please refer to the preparation method of Compound 1-7 for the preparation method of Compound 28-7. LCMS (ESI) m/z: 557.3 (M+1).

Step 7:

Please refer to the preparation method of Compound 1-8 for the preparation method of Compound 28-8. LCMS (ESI) m/z: 457.2 (M+1).

Step 8:

Please refer to the preparation method of Compound 1-10 for the preparation method of Compound 28-9. LCMS (ESI) m/z: 642.3 (M+1).

Step 9:

Please refer to Example 1 for the preparation method of Example 28. $^1$H NMR (400 MHz, DMSO-d$_6$) δ 9.41 (br s, 1H), 9.08-8.72 (m, 2H), 7.84-7.49 (m, 3H), 7.26-7.09 (m, 1H), 4.51-4.23 (m, 3H), 4.10-3.79 (m, 4H), 3.72-3.51 (m, 1H), 2.46 (br s, 6H), 2.14 (br d, J=6.0 Hz, 2H), 1.95 (br s, 1H), 1.90-1.54 (m, 9H), 1.35 (br d, J=6.2 Hz, 3H), 1.29-0.94 (m, 6H); LCMS (ESI) m/z: 542.3 (M+1).

Example 29

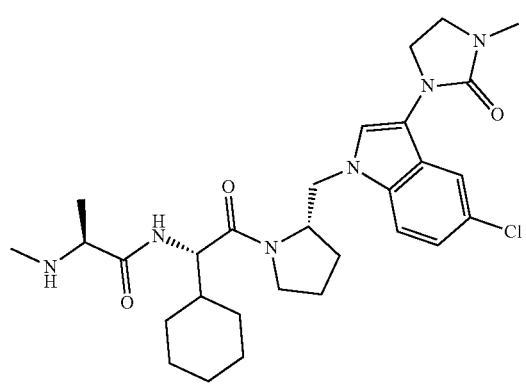

Please refer to Example 28 for the preparation method of Example 29. $^1$H NMR (400 MHz, CD$_3$OD) δ 7.67 (d, J=8.8 Hz, 1H), 7.57 (d, J=1.8 Hz, 1H), 7.31 (s, 1H), 7.15 (dd, J=8.7, 1.9 Hz, 1H), 4.59-4.38 (m, 4H), 4.08-3.98 (m, 1H), 3.96-3.90 (m, 1H), 3.88-3.81 (m, 2H), 3.81-3.74 (m, 1H), 3.72-3.64 (m, 1H), 3.61-3.53 (m, 2H), 2.89 (s, 4H), 2.67 (s, 3H), 1.93 (br d, J=9.7 Hz, 2H), 1.88-1.66 (m, 9H), 1.52-1.49 (m, 3H), 1.36-1.08 (m, 6H); LCMS (ESI) m/z: 557.3 (M+1).

Example 30

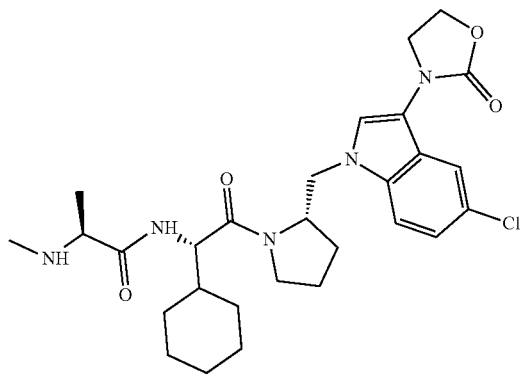 [SMILES: CN[C@@H](C)C(=O)N[C@H](C(=O)N1CCC[C@H]1Cn1cc(N2CCOC2=O)c2cc(Cl)ccc21)C1CCCCC1]

Please refer to Example 28 for the preparation method of Example 30. $^1$H NMR (400 MHz, CD$_3$OD) δ 7.70 (d, J=8.8 Hz, 1H), 7.63 (d, J=2.0 Hz, 1H), 7.45 (s, 1H), 7.21-7.14 (m, 1H), 4.60-4.55 (m, 2H), 4.54-4.43 (m, 3H), 4.12 (dt, J=8.1, 3.5 Hz, 2H), 4.07-3.98 (m, 1H), 3.97-3.89 (m, 1H), 3.84-3.75 (m, 1H), 3.73-3.64 (m, 1H), 2.67 (s, 3H), 2.00-1.89 (m, 2H), 1.87-1.76 (m, 6H), 1.71 (br d, J=10.8 Hz, 2H), 1.51 (d, J=7.0 Hz, 3H), 1.36-1.06 (m, 6H); LCMS (ESI) m/z: 544.3 (M+1).

Example 31

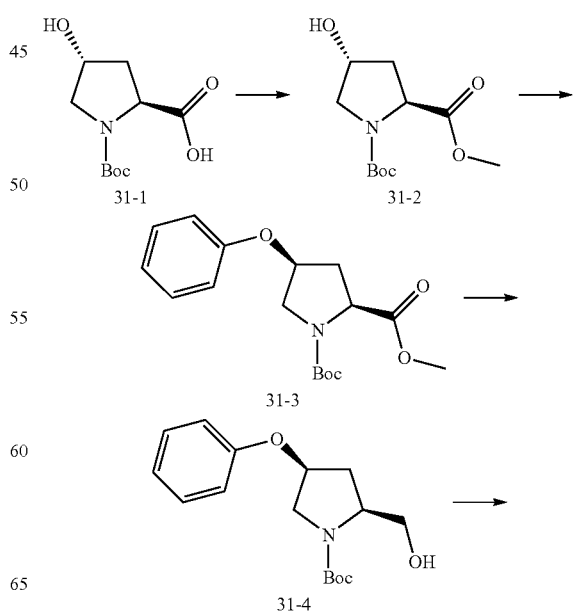

-continued

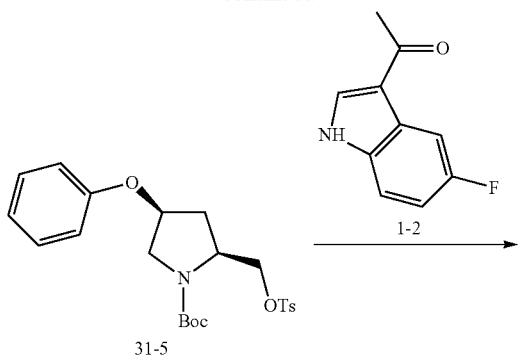

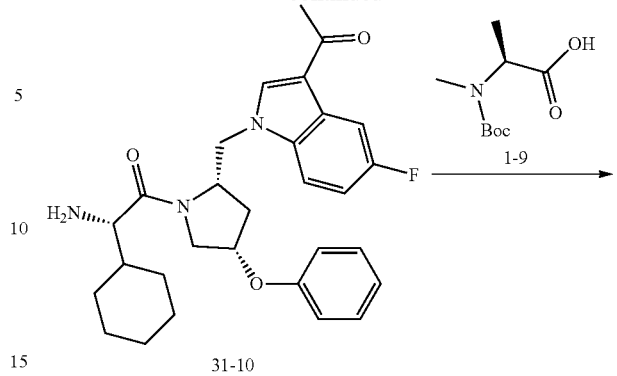

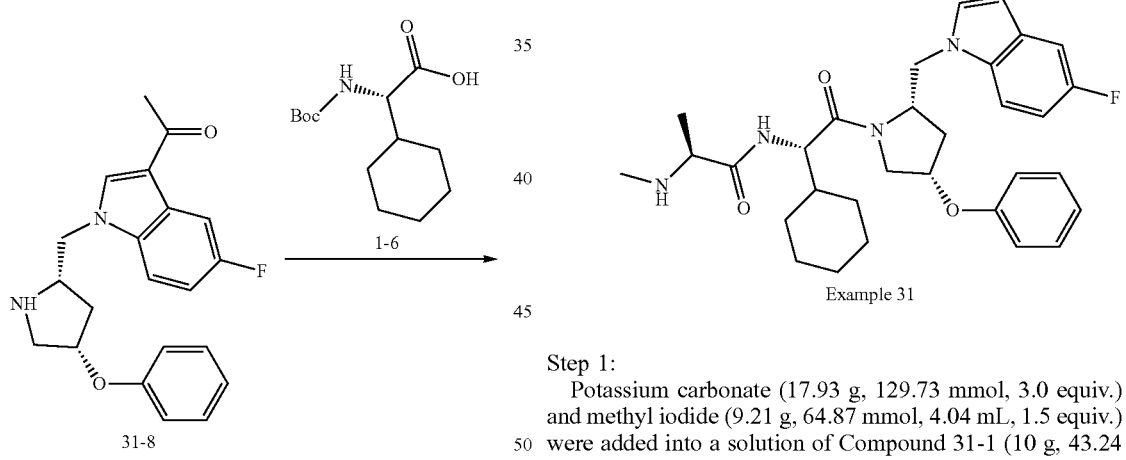

Step 1:
Potassium carbonate (17.93 g, 129.73 mmol, 3.0 equiv.) and methyl iodide (9.21 g, 64.87 mmol, 4.04 mL, 1.5 equiv.) were added into a solution of Compound 31-1 (10 g, 43.24 mmol, 1.0 equiv.) in DMF (100 mL), and the resulting mixture was reacted at 15° C. for 5 hours. TLC (petroleum ether:ethyl acetate=1:1) showed that the reaction was complete. Water (100 mL) was added into the reaction solution, and the resulting mixture was extracted with ethyl acetate (100 mL×2). The combined organic phases were washed with saturated saline (100 mL×3) and then concentrated to obtain Compound 31-2. The crude product was used directly in the next step.

Step 2:
Under the protection of nitrogen, phenol (3.8 g, 40.36 mmol, 3.55 mL, 1.1 equiv.), triphenylphosphine (10.59 g, 40.36 mmol, 1.1 equiv.) and DIAD (8.16 g, 40.36 mmol, 7.85 mL, 1.1 equiv.) were added into a solution of Compound 31-2 (9.0 g, 36.69 mmol, 1.0 equiv.) in tetrahydrofuran (150 mL). The resulting mixture was stirred at 15° C. for 12 hours. LCMS showed that the reaction was complete.

The reaction solution was concentrated, water (100 mL) and ethyl acetate (200 mL) were added into the resulting residue, and the resulting mixture was subjected to liquid-liquid separation. The organic phase was washed with saturated saline (100 mL×2) and then concentrated to obtain Compound 31-3. The crude product was used directly in the next step. LCMS (ESI) m/z: 322.2 (M+1).

Step 3:
Lithium aluminum hydride (1.59 g, 42.01 mmol, 1.5 equiv.) was added into a solution of Compound 31-3 (9 g, 28.01 mmol, 1.0 equiv.) in tetrahydrofuran (100 mL) at 0° C., and the resulting mixture was reacted at 15° C. for 2 hours. LCMS showed that the reaction was complete. To the reaction solution, water (3 mL), a 30% sodium hydroxide solution (6 mL) and water (3 mL) were successively added dropwise to quench the reaction. The resulting mixture was filtered, the filter cake was washed with ethyl acetate (100 mL), and the filtrate was concentrated. The resulting residue was purified by silica gel column chromatography (petroleum ether:ethyl acetate=10:to 2:1) to obtain Compound 31-4. LCMS (ESI) m/z: 316.2 (M+23).

Step 4:
Pyridine (4.04 g, 51.13 mmol, 4.13 mL, 3.0 equiv.) and p-toluenesulfonyl chloride (6.50 g, 34.09 mmol, 2.0 equiv.) were added into a solution of Compound 31-4 (5 g, 17.04 mmol, 1.0 equiv.) in dichloromethane (150 mL) at 0° C., and the resulting mixture was stirred at 15° C. for 10 hours. LCMS showed that the reaction was complete. The reaction solution was concentrated, and the resulting residue was purified by silica gel column chromatography (petroleum ether:ethyl acetate=20:1 to 3:1) to obtain Compound 31-5. LCMS (ESI) m/z: 470.2 (M+23).

Step 5:
Please refer to the preparation method of Compound 1-4 for the preparation method of Compound 31-7. LCMS (ESI) m/z: 453.1 (M+1).

Step 6:
Please refer to the preparation method of Compound 1-5 for the preparation method of Compound 31-8.

Step 7:
Please refer to the preparation method of Compound 1-7 for the preparation method of Compound 31-9. LCMS (ESI) m/z: 592.1 (M+1).

Step 8:
Please refer to the preparation method of Compound 1-8 for the preparation method of Compound 31-10.

Step 9:
Please refer to the preparation method of Compound 1-10 for the preparation method of Compound 31-11. LCMS (ESI) m/z: 677.2 (M+1).

Step 10:
Please refer to Example 1 for the preparation method of Example 31. $^1$H NMR (400 MHz, DMSO-$d_6$) δ 9.60-9.34 (m, 1H), 8.98-8.83 (m, 1H), 8.80 (d, J=7.8 Hz, 1H), 7.98 (s, 1H), 7.83 (dd, J=9.8, 2.6 Hz, 1H), 7.73 (dd, J=9.0, 4.5 Hz, 1H), 7.44-7.34 (m, 2H), 7.15-7.08 (m, 3H), 7.07-7.01 (m, 1H), 5.22 (br s, 1H), 4.73-4.56 (m, 2H), 4.37 (t, J=7.6 Hz, 1H), 4.33-4.22 (m, 1H), 4.10 (dd, J=11.8, 4.6 Hz, 1H), 3.93-3.83 (m, 2H), 2.45 (br t, J=5.2 Hz, 4H), 2.31 (s, 3H), 2.21-2.09 (m, 1H), 2.00 (br d, J=14.2 Hz, 1H), 1.71-1.55 (m, 6H), 1.35 (d, J=6.8 Hz, 3H), 1.22-0.92 (m, 6H); LCMS (ESI) m/z: 577.2 (M+1).

The compounds involved in the present disclosure are IAP inhibitors. The following experimental results confirm that the compounds listed in the present patent application are IAP inhibitors and may be used as potential anticancer drugs. $IC_{50}$ used herein refers to a concentration of a certain reagent, and 50% of the maximum inhibition may be achieved when the reagent is used in said concentration.

Experimental Example I

Binding Experiment of cIAP1 BIR3 and XIAP BIR3

Experimental Materials:
Buffer system for the test (a buffer for cIAP1 BIR3 or XIAP BIR3): 100 mM potassium phosphate, pH 7.5; 0.1% BSA; 0.005% Triton X-100; and 1% dimethyl sulfoxide.
Probe: ARPFAQ-K(5-FAM)-NH$_2$.
Targets:
cIAP1-BIR3-his: RBC Cat #APT-11-370, the BIR3 domain of human cIAP1 (covering amino acids 258 to 363; cIAP1 BIR3), as a GST-fusion protein expressed and purified from E. coli.
XIAP-BIR3-his: RBC Cat #APT-11-374, the BIR3 domain of XIAP (covering amino acids 255 to 356; XIAP BIR3), as a GST-fusion protein expressed and purified from E. coli.
Reaction conditions: 5 nM ARPFAQ-K(5-FAM)-NH$_2$, 20 nM cIAP1 BIR3 and 30 nM XIAP BIR3.

Steps of Experiment:
First, a fresh buffer for cIAP1 BIR3 or XIAP BIR3 was prepared, a cIAP1 BIR3 or XIAP BIR3 solution (2-fold diluted) was added thereto, and then a compound to be tested which had been dissolved in 100% DMSO was added into the buffer solution containing cIAP1 BIR3 or XIAP BIR3 by an acoustic technique. Thereafter, the probe (2-fold diluted) was added, and the resultant was mixed and incubated in the dark at room temperature for 60 minutes. The fluorescence polarization was measured and the mP value was calculated. Finally, the $IC_{50}$ value was obtained.

Results of Experiment:
As shown in Table 1.

Conclusion of Experiment:
The compounds of the present disclosure exhibited cIAP1 BIR3-binding activity and were selective for cIAP1 and XIAP.

Experimental Example II

In-Vitro Cell Viability Test

Experimental Materials:
RPMI 1640 medium (Invitrogen-22400089); fetal bovine serum (Invitrogen-10099141); Trypsin, 0.05% (1×) with EDTA 4Na (Invitrogen-25300062); luminescent cell viability assay kit (Promega-G7573); Dulbecco's phosphate buffered saline (HyClone-SH30028.01B); and 384-well plate (Corning-6007680). Envision Multi-label Analyzer.

Experimental Method:
1. 30 μL of MDA-MB-231 cell suspension, which contained 250 MDA-MB-231 cells, was added into the wells of a 384-microwell plate.
2. 20 μL of a test compound (the test compounds were formulated at a high concentration of 10 μM, the test compounds were subjected to a 5-fold gradient dilution, and each compound was diluted to 10 concentration gradients) was added, and then the cell plate was put back into a carbon dioxide incubator to be incubated for 7 days.
3. The cell plate was kept flat at room temperature for 30 minutes.
4. 20 μL of a Promega CellTiter-Glo reagent was added into each well of the cell plate.

5. After 10 minutes, the Envision Multi-label Analyzer was used for data reading.
Results of Experiment: See Table 1.
Conclusion of Experiment:
 The compounds of the present disclosure had anti-proliferative activity on MDA-MB-231 cells.

TABLE 1

| Test Compounds | cIAP1 BIR3 IC$_{50}$ (nM) | XIAP BIR3 IC$_{50}$ (nM) | MDA-MB-231 Cell IC$_{50}$ (nM) |
|---|---|---|---|
| Example 1 | 3.7 | 74.7 | 70.0 |
| Example 2 | 5.0 | 29.9 | 54.8 |
| Example 3 | 1.0 | 18.1 | 16.0 |
| Example 4 | 2.6 | 97.0 | 220.0 |
| Example 5 | 2.6 | 95.9 | 75.0 |
| Example 6 | 58.3 | 9.3 | 497.0 |
| Example 7 | 4.9 | 45.0 | 16.6 |
| Example 8 | 5.6 | 40.3 | 75.0 |
| Example 9 | 5.7 | 20.0 | 26.0 |
| Example 10 | 4.5 | 27.2 | 32.4 |
| Example 11 | 5.2 | 139.0 | 74.8 |
| Example 13 | 5.0 | 30.6 | 44.3 |
| Example 14 | 6.2 | 49.9 | 57.7 |
| Example 15 | 4.0 | 258.0 | 93.0 |
| Example 16 | 8.4 | 346.0 | 109.3 |
| Example 17 | 1.9 | 80.7 | 79.0 |
| Example 18 | 5.1 | 42.5 | 22.5 |
| Example 19 | 4.6 | 129.0 | 43.1 |
| Example 20 | 1.1 | 53.9 | 75.0 |
| Example 21 | 4.2 | 37.4 | 16.4 |
| Example 22 | 3.0 | 42.0 | 85.0 |
| Example 23 | 4.6 | 21.3 | 45.2 |
| Example 24 | 4.1 | 19.2 | 73.0 |
| Example 25 | 6.8 | 208.0 | 1153.0 |
| Example 26 | 1.1 | 60.0 | 181.0 |
| Example 27 | 4.4 | 46.4 | 282.1 |
| Example 28 | 5.2 | 27.3 | 36.7 |
| Example 29 | 6.1 | 31.4 | 134.0 |
| Example 30 | 4.4 | 21.6 | 47.6 |
| Example 31 | 3.7 | 49.1 | 1461.0 |

Experimental Example III

In-Vivo Drug Efficacy Study 1

The in-vivo drug efficacy experiments were carried out in BALB/c nude mice implanted subcutaneously with human tumor cell line-derived xenograft (CDX) derived from patients suffering from MDA-MB-231 triple-negative breast cancer.
Experimental Operation:
 BALB/c nude mice, female, 6 to 8 weeks old, weighing about 18 to 22 g, were kept in a special pathogen-free environment and in separated ventilated cages (3 mice per cage). All cages, bedding and water were disinfected before use. All animals had free access to standard certified commercial laboratory diets. A total of 48 mice purchased from Shanghai BK Laboratory Animal Co., LTD were used for the study. Each mouse was inoculated subcutaneously in the right flank with tumor cells (10×10$^6$ cells in 0.2 mL of a phosphate buffer) for tumor growth. The administration was initiated when the average tumor volume reached about 147 cubic millimeters. The test compounds were orally administered daily at a dose of 30 mg/kg. Tumor volumes were measured with a two-dimensional caliper every 3 days. The volume was measured in cubic millimeters and calculated by the following formula: V=0.5 a×b$^2$, where a and b were the long and short diameters of a tumor, respectively. Anti-tumor efficacy was determined by dividing the average increase in tumor volume of animals treated with a compound by the average increase in tumor volume of untreated animals.
Results of Experiment: See Table 2.
Conclusion of Experiment:
 In the MDA-MB-231 triple-negative breast cancer CDX model used for in-vivo drug efficacy study, the compounds of the present disclosure exhibited drug efficacy.

TABLE 2

| Examples | Dose (mg/kg) | Tumor Volume (mm$^3$) | | | |
|---|---|---|---|---|---|
| | | Day 0 | Day 6 | Day 13 | Day 20 |
| Blank Control | 0 | 148 | 475 | 1225 | 1750 |
| Example 2 | 30 | 147 | 214 | 282 | 810 |

Experimental Example IV

In-Vivo Drug Efficacy Study 2

The in-vivo drug efficacy experiments were carried out in BALB/c nude mice implanted subcutaneously with human tumor cell line-derived xenograft (CDX) derived from patients suffering from MDA-MB-231 triple-negative breast cancer.
Experimental Operation:
 BALB/c nude mice, female, 6 to 8 weeks old, weighing about 18 to 22 g, were kept in a special pathogen-free environment and in separated ventilated cages (3 mice per cage). All cages, bedding and water were disinfected before use. All animals had free access to standard certified commercial laboratory diets. A total of 48 mice purchased from Shanghai BK Laboratory Animal Co., LTD were used for the study. Each mouse was inoculated subcutaneously in the right flank with tumor cells (10×10$^6$ cells in 0.2 mL of a phosphate buffer) for tumor growth. The administration was initiated when the average tumor volume reached about 110 cubic millimeters. The test compounds were orally administered daily at a dose of 30 mg/kg. Tumor volumes were measured with a two-dimensional caliper every 3 days. The volume was measured in cubic millimeters and calculated by the following formula: V=0.5 a×b$^2$, where a and b were the long and short diameters of a tumor, respectively. Anti-tumor efficacy was determined by dividing the average increase in tumor volume of animals treated with a compound by the average increase in tumor volume of untreated animals.
Conclusion of Experiment:
 In the MDA-MB-231 triple-negative breast cancer CDX model used for in-vivo drug efficacy study, the compounds of the present disclosure exhibited relatively good drug efficacy.

TABLE 3

| Examples | Dose (mg/kg) | Tumor volume (mm$^3$) | | | |
|---|---|---|---|---|---|
| | | Day 0 | Day 5 | Day 12 | Day 20 |
| Blank Control | 0 | 110 | 261 | 526 | 772 |
| Example 2 | 30 | 110 | 111 | 86 | 177 |

What is claimed is:
 1. A compound represented by formula (I) or a pharmaceutically acceptable salt thereof,

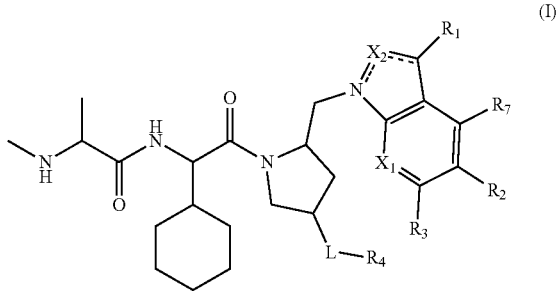

(I)

wherein, $X_1$ is $C(R_5)$ or N;

$X_2$ is $C(R_6)$, N, O, or S;

⫽ are each independently a single bond or a double bond;

L is a single bond or —O—;

$R_1$ is —C(=O)NH$_2$, CN, $C_{1-5}$ alkyl, $C_{1-5}$ heteroalkyl, phenyl, 5- to 6-membered heteroaryl, or 5- to 6-membered heterocycloalkyl; said $C_{1-5}$ alkyl, $C_{1-5}$ heteroalkyl, phenyl, 5- to 6-membered heteroaryl or 5- to 6-membered heterocycloalkyl is optionally substituted with 1, 2 or 3 R;

$R_2$ is H, halogen, CN, COOH, —C(=O)NH$_2$, $C_{1-4}$ alkyl, or $C_{1-4}$ heteroalkyl; said $C_{1-4}$ alkyl or $C_{1-4}$ heteroalkyl is optionally substituted with 1, 2 or 3 R;

$R_3$ and $R_7$ are each independently H, halogen or $C_{1-4}$ alkyl; said $C_{1-4}$ alkyl is optionally substituted with 1, 2 or 3 R;

$R_4$ is H, phenyl, or 5- to 6-membered heteroaryl;

$R_5$ is H or halogen;

$R_6$ is H, halogen, $C_{1-4}$ alkyl, $C_{1-4}$ heteroalkyl, CN, or COOH; said $C_{1-4}$ alkyl or $C_{1-4}$ heteroalkyl is optionally substituted with 1, 2 or 3 R;

R is halogen, OH, CN, CH$_3$, CH$_3$CH$_2$, CH$_3$CH$_2$CH$_2$, CH(CH$_3$)$_2$, OCH$_3$, OCF$_3$, CHF$_2$, CH$_2$F, or NH$_2$; and said $C_{1-4}$ heteroalkyl, $C_{1-5}$ heteroalkyl, 5- to 6-membered heterocycloalkyl and 5- to 6-membered heteroaryl each contain 1, 2 or 3 heteroatoms or heteroatom radicals independently selected from the group consisting of —NH—, —O—, —S—, N, —C(=O)O—, —C(=O)—, —C(=O)NH—, —C(=S)—, —S(=O)—, —S(=O)$_2$—, —C(=NH)—, —S(=O)$_2$NH—, —S(=O)NH—, and —NHC(=O)NH—.

2. The compound according to claim 1 or a pharmaceutically acceptable salt thereof, which is a compound of formula (I'):

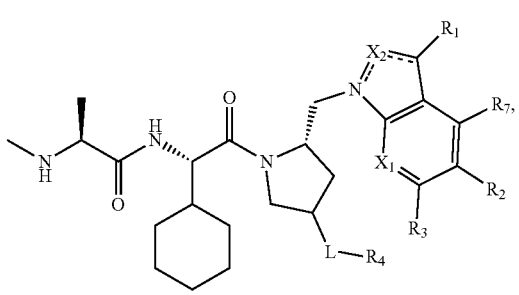

(I')

wherein ⫽, $X_1$, $X_2$, L, $R_1$, $R_2$, $R_3$, $R_4$ and $R_7$ are as defined in claim 1.

3. The compound according to claim 1 or a pharmaceutically acceptable salt thereof, wherein $X_2$ is $C(R_6)$ or N.

4. The compound according to claim 1 or a pharmaceutically acceptable salt thereof, wherein $R_1$ is —C(=O)NH$_2$, CN, CH$_3$, CH$_3$CH$_2$, $C_{1-5}$ alkyl-C(=O)—, $C_{1-4}$ alkyl-C(=O)—, $C_{1-5}$ alkyl-S(=O)$_2$—, $C_{1-5}$ alkyl-N(H)C(=O)—, $C_{1-4}$ alkyl-N(H)C(=O)—, (C$_{1-2}$ alkyl)$_2$-N—C(=O)—, phenyl,

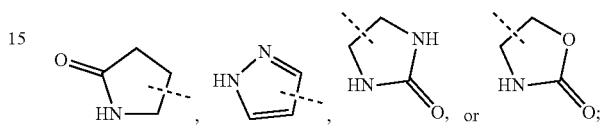

said CH$_3$, CH$_3$CH$_2$, $C_{1-5}$ alkyl-C(=O)—, $C_{1-4}$ alkyl-C(=O)—, $C_{1-5}$ alkyl-S(=O)$_2$—, $C_{1-5}$ alkyl-N(H)C(=O)—, $C_{1-4}$ alkyl-N(H)C(=O)—, (C$_{1-2}$ alkyl)$_2$-N—C(=O)—, phenyl,

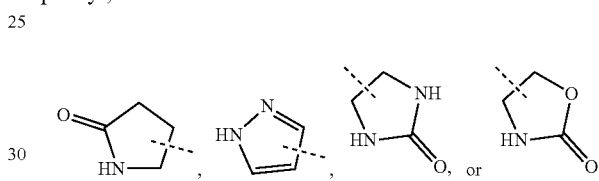

is optionally substituted with 1, 2 or 3 R.

5. The compound according to claim 1 or a pharmaceutically acceptable salt thereof, wherein $R_1$ is

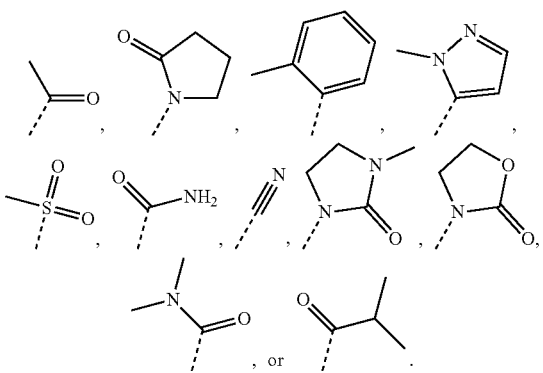

6. The compound according to claim 1 or a pharmaceutically acceptable salt thereof, wherein $R_2$ is H, halogen, $C_{1-4}$ alkyl, or $C_{1-4}$ alkyl-O—; said $C_{1-4}$ alkyl or $C_{1-4}$ alkyl-O— is optionally substituted with 1, 2 or 3 halogens.

7. The compound according to claim 6 or a pharmaceutically acceptable salt thereof, wherein $R_2$ is H, F, Cl, Br, CF$_3$, or OCF$_3$.

8. The compound according to claim 1 or a pharmaceutically acceptable salt thereof, wherein $R_3$ and $R_7$ are each independently H, F, or Cl.

9. The compound according to claim 1 or a pharmaceutically acceptable salt thereof, wherein $R_4$ is H or

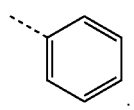

10. The compound according to claim 1 or a pharmaceutically acceptable salt thereof, wherein $R_5$ is H or Cl.

11. The compound according to claim 1 or a pharmaceutically acceptable salt thereof, wherein $R_6$ is H, Cl, or $CH_3$.

12. The compound according to claim 1 or a pharmaceutically acceptable salt thereof, wherein a structural unit

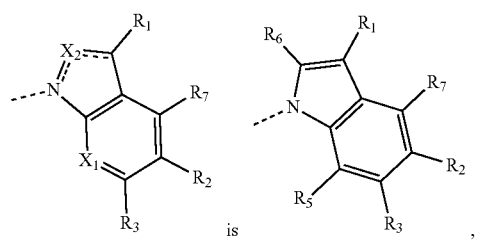

is

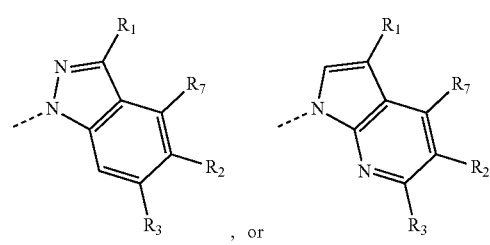

, or

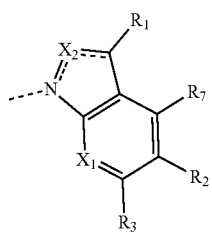

.

13. The compound according to claim 1 or a pharmaceutically acceptable salt thereof, wherein a structural unit

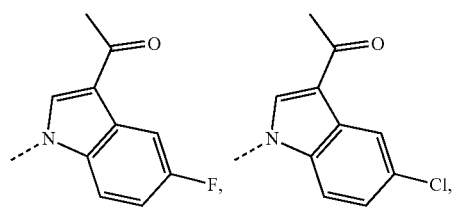

is

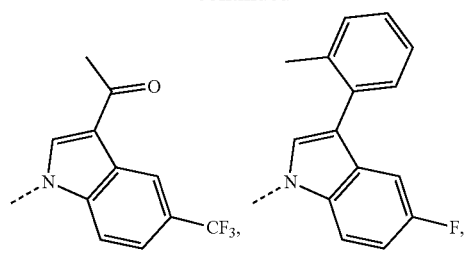

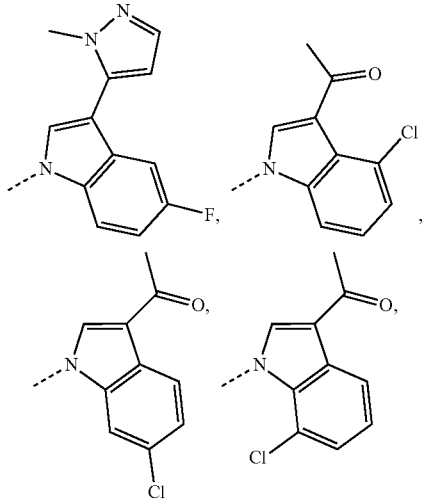

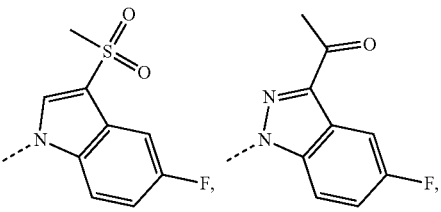

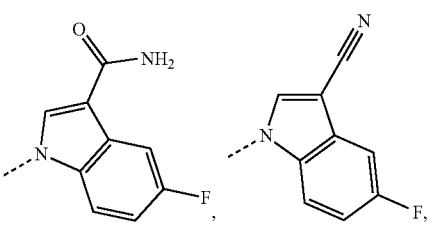

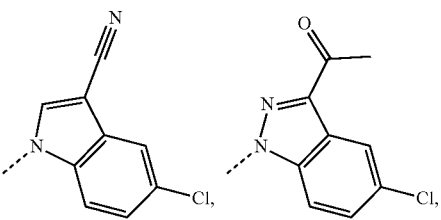

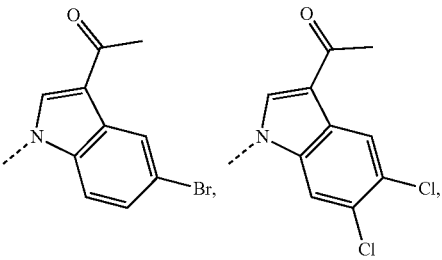

-continued
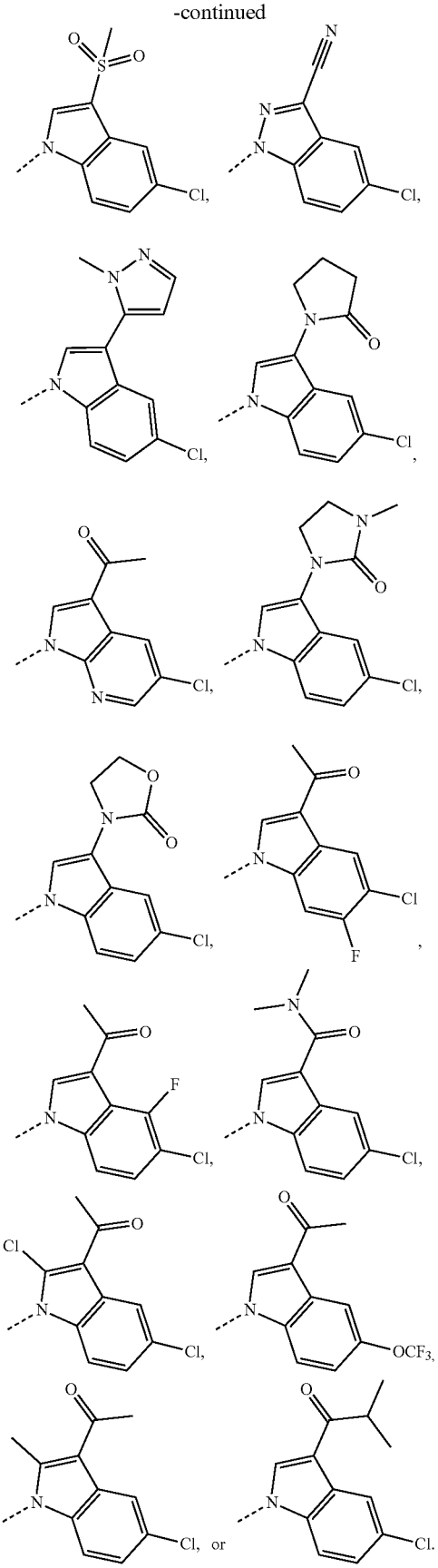
14. The compound according to claim 1 or a pharmaceutically acceptable salt thereof, which is a compound of formula (II) or (III):
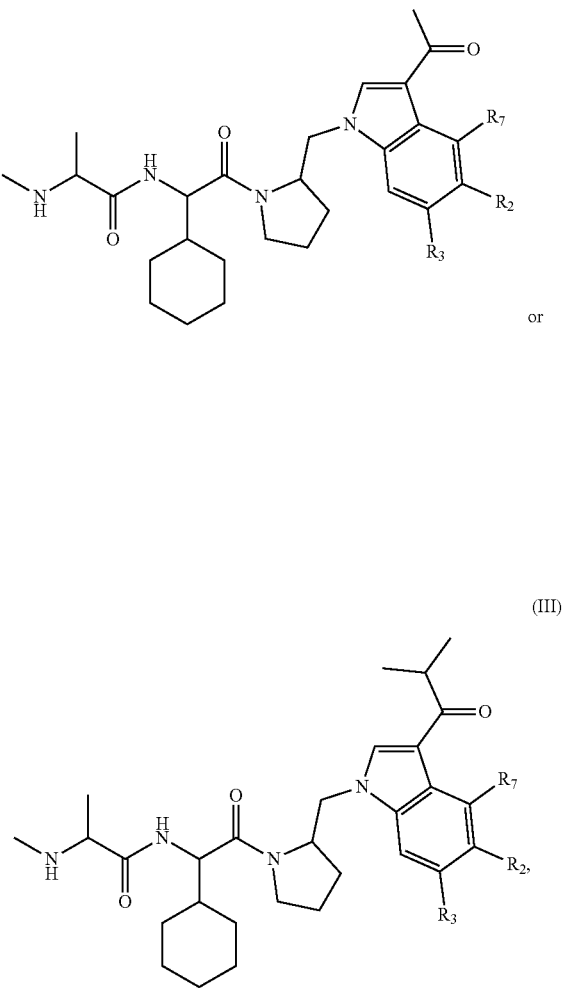
wherein $R_2$, $R_3$ and $R_7$ are as defined in claim 1.
15. The compound according to claim 2 or a pharmaceutically acceptable salt thereof, which is a compound of formula (II') or (III'):
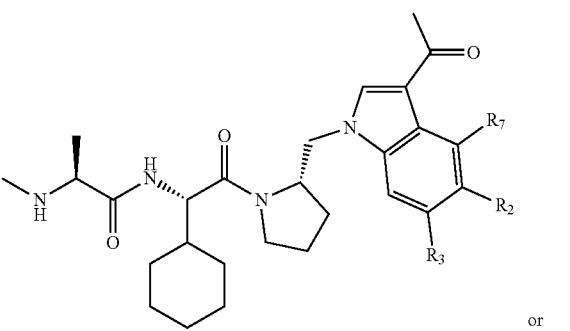
or -continued
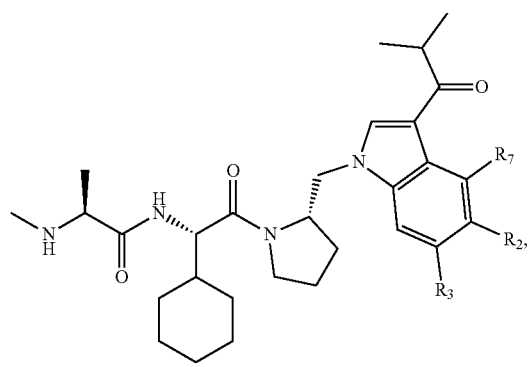
wherein R₂, R₃ and R₇ are as defined in claim 2.
16. A compound or a pharmaceutically acceptable salt thereof, which is
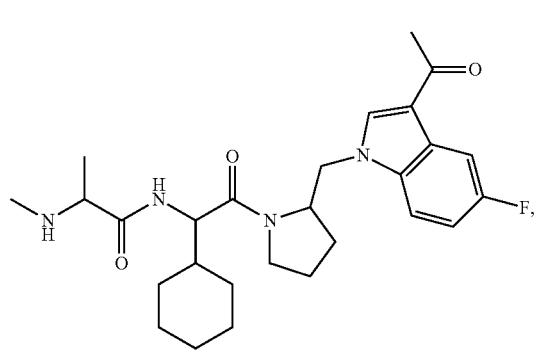
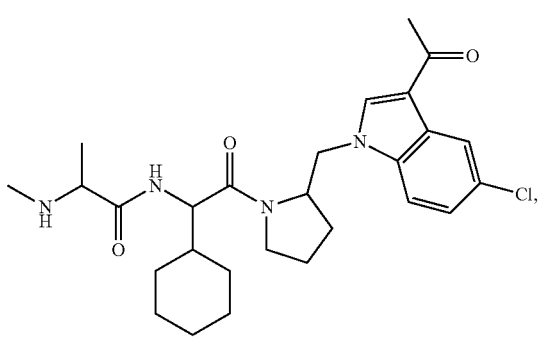
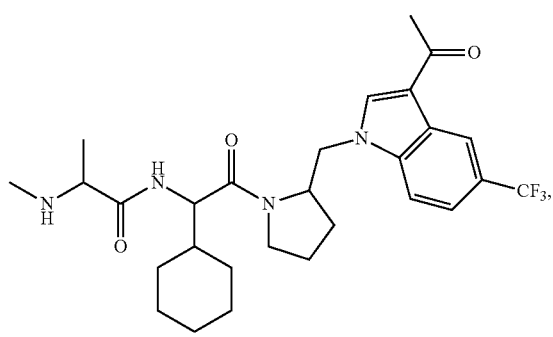
-continued
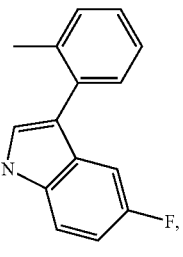
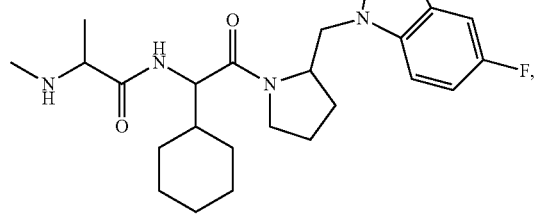
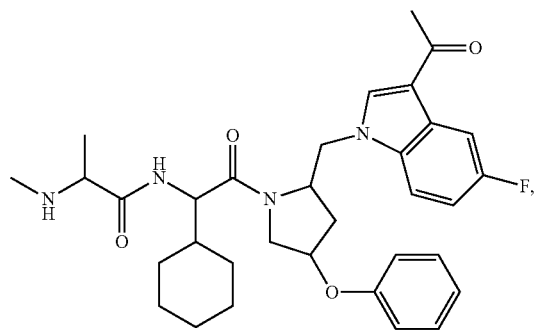
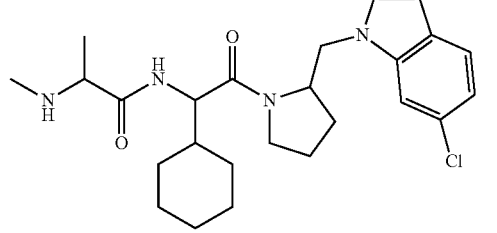

95
-continued
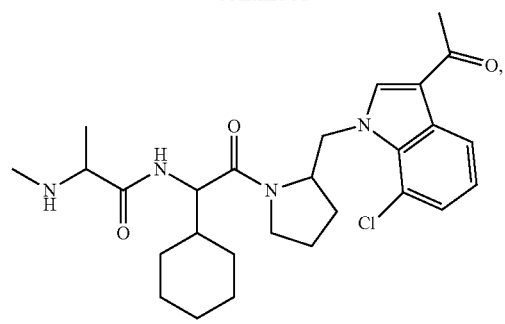
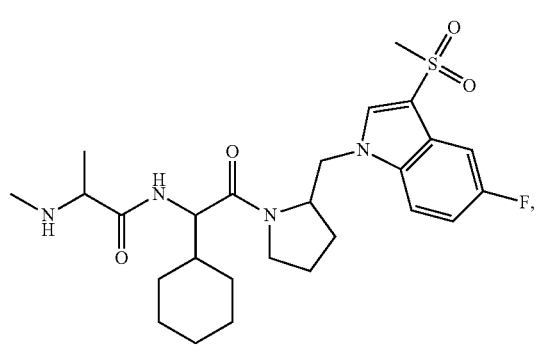
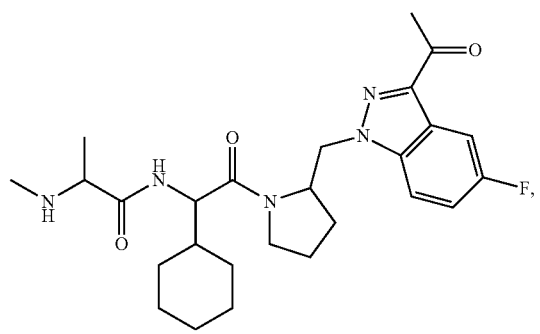
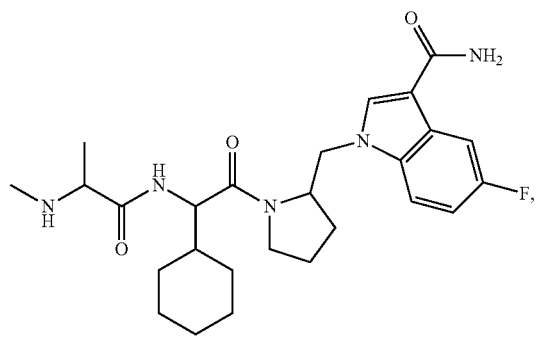
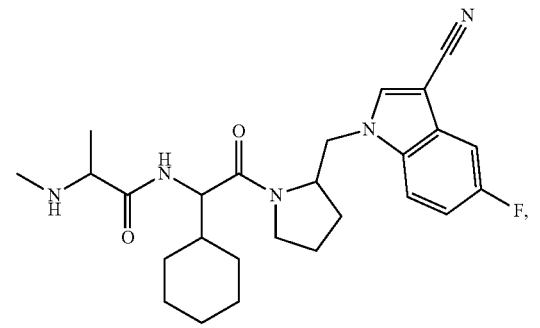
96
-continued
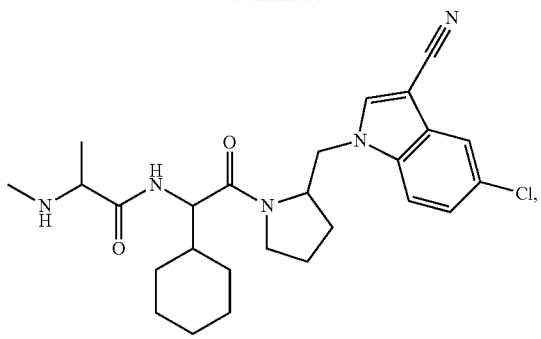
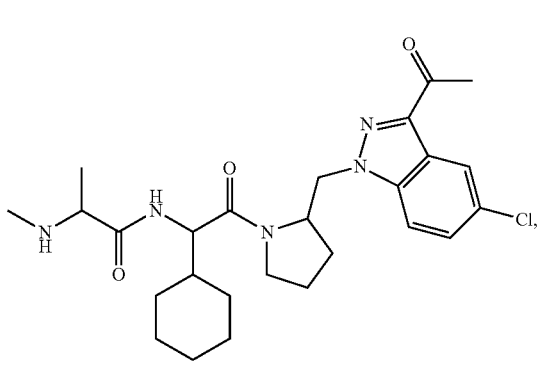
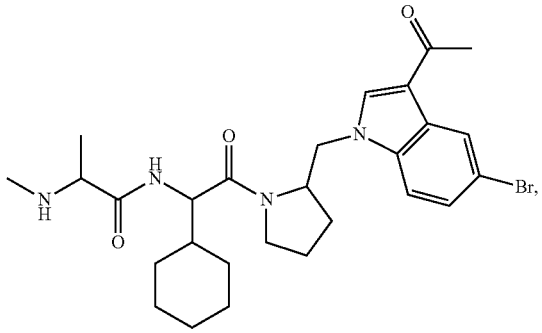
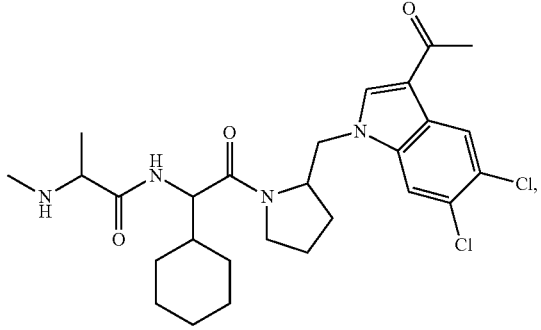
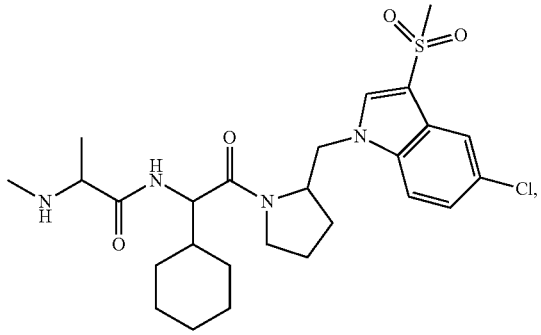

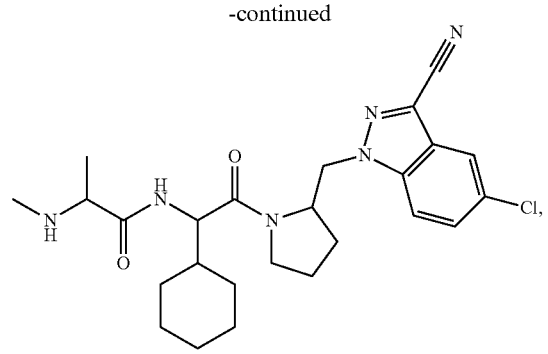
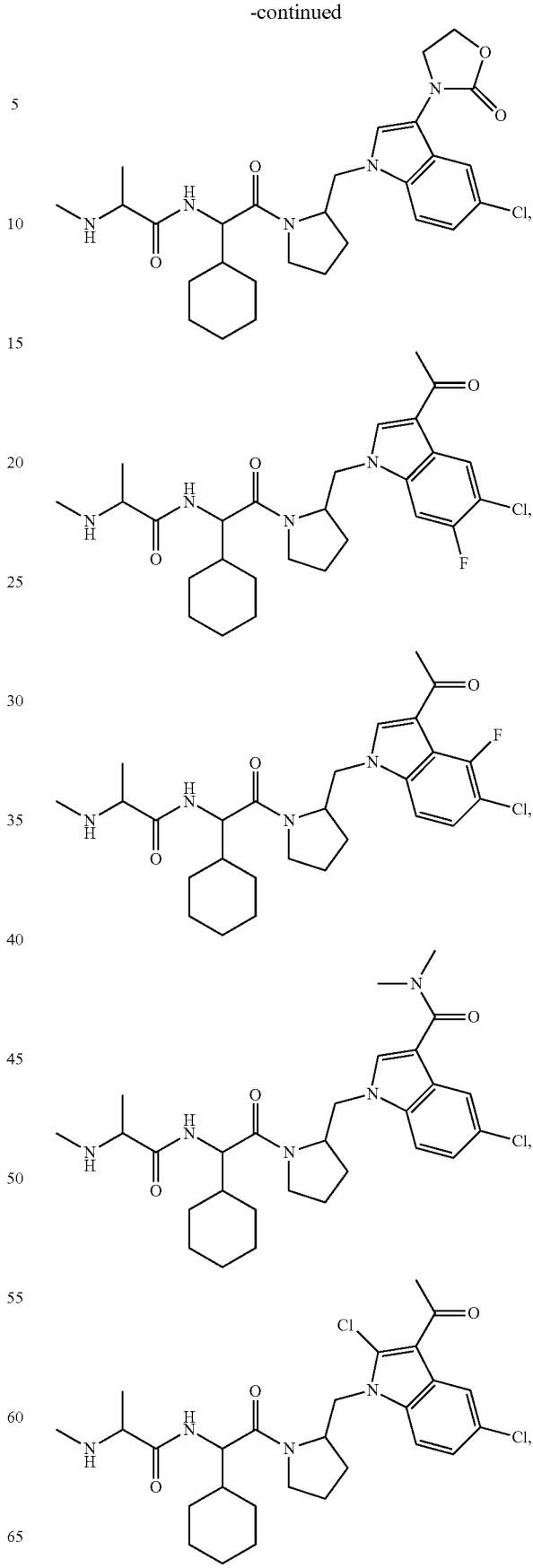

99
-continued
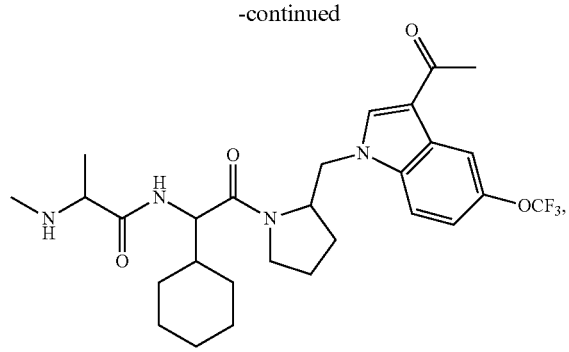
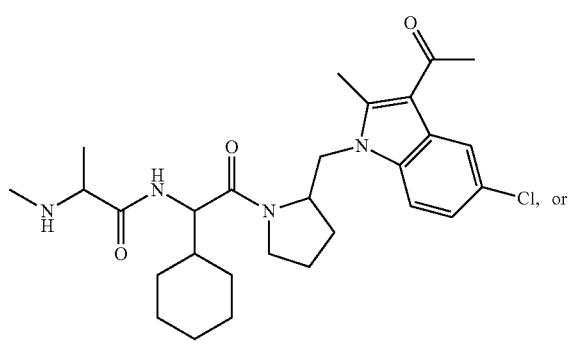
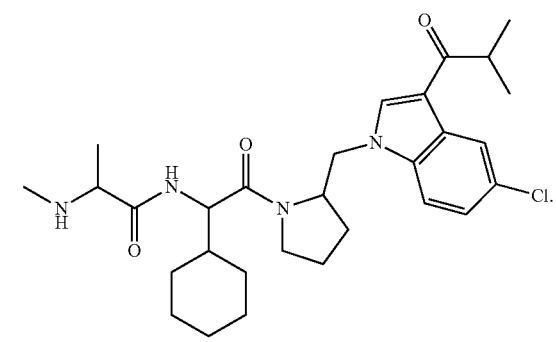
17. The compound according to claim 16 or a pharmaceutically acceptable salt thereof, which is
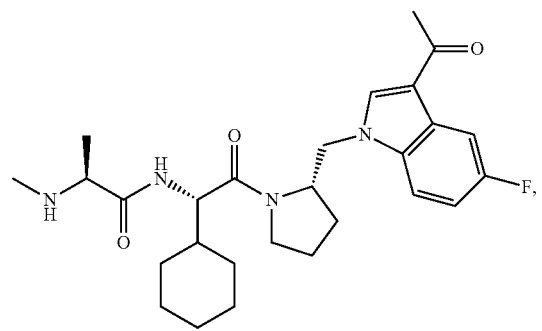
100
-continued
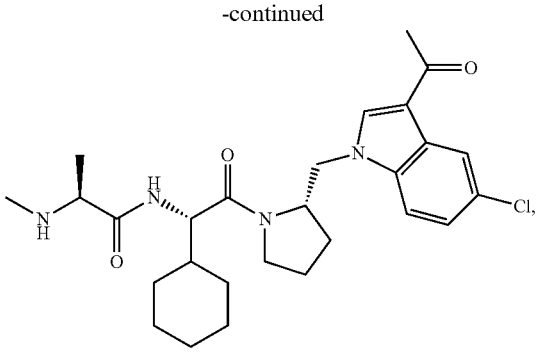
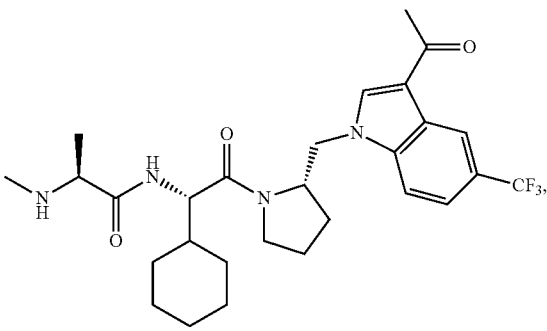
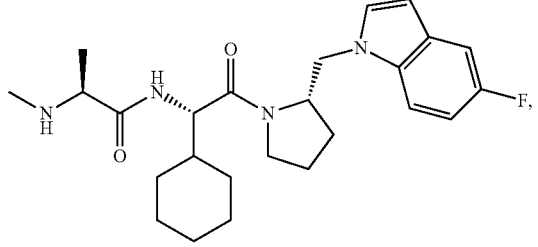
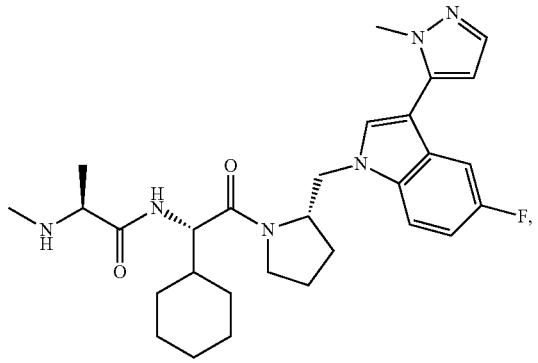
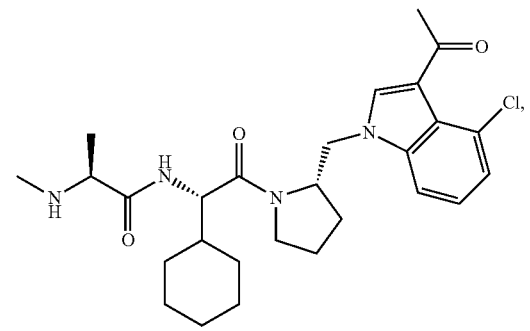

101
-continued
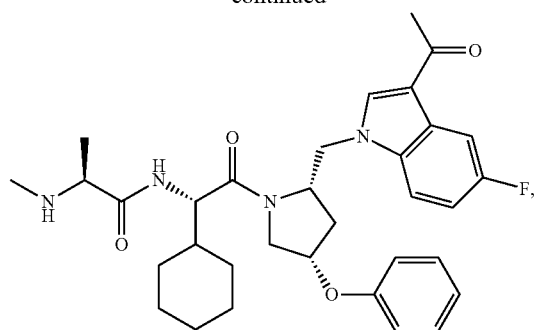
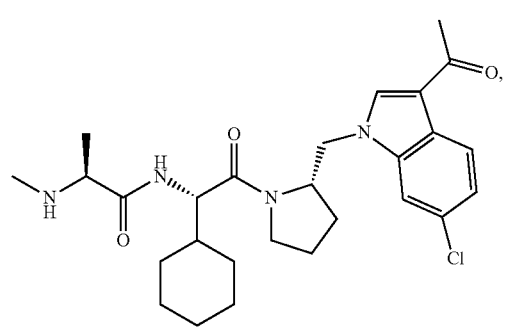
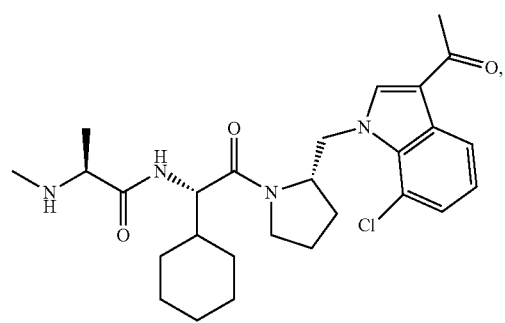
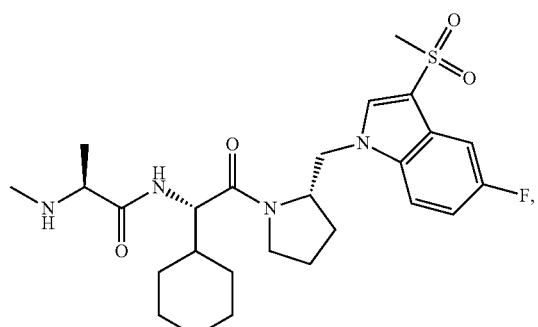
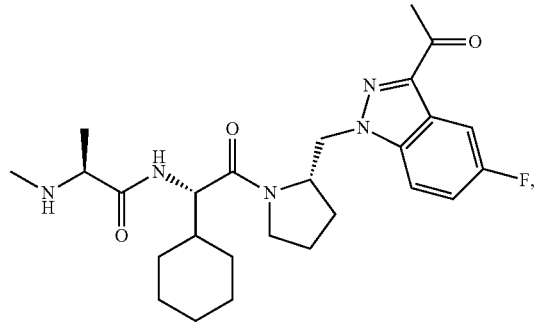
102
-continued
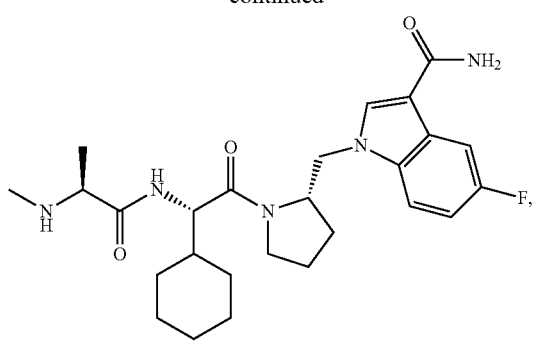
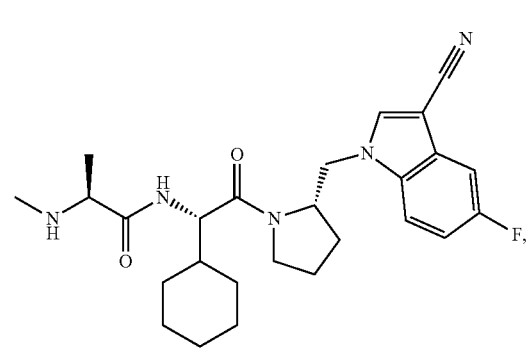
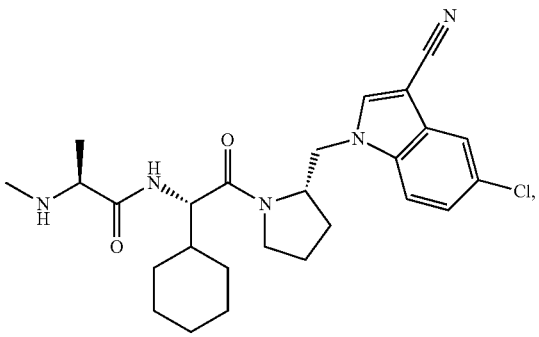
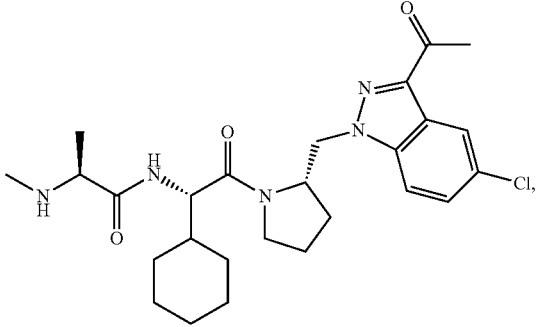
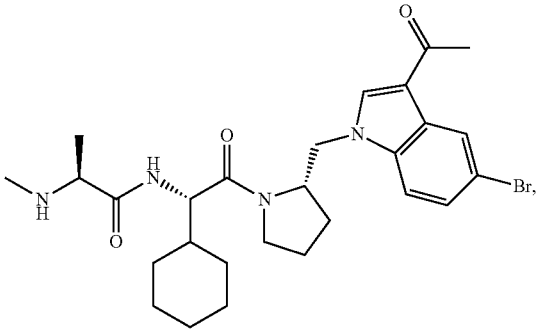

103
-continued
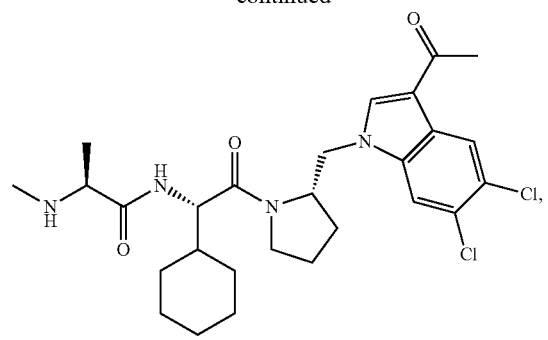
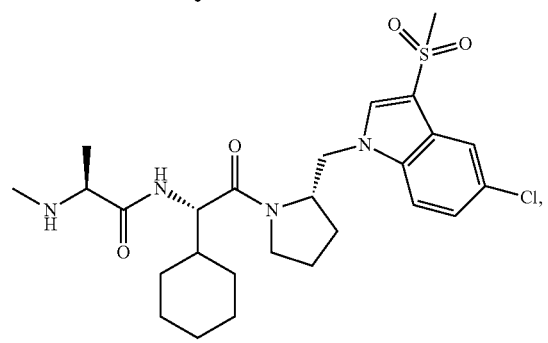
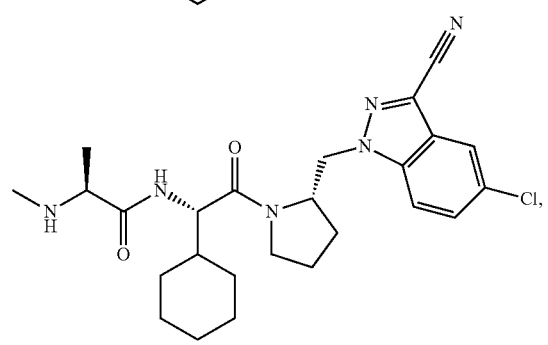
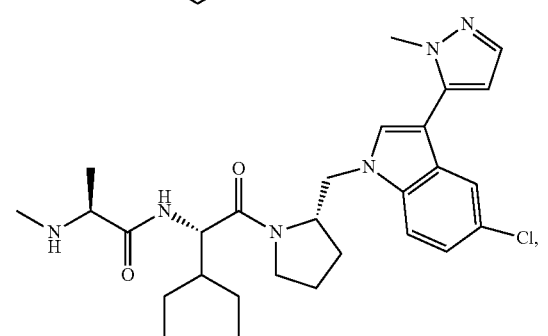
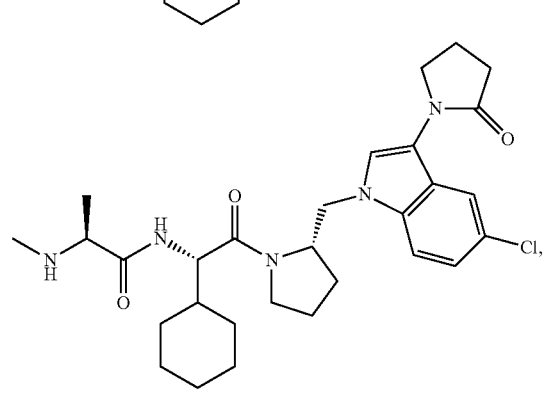
104
-continued
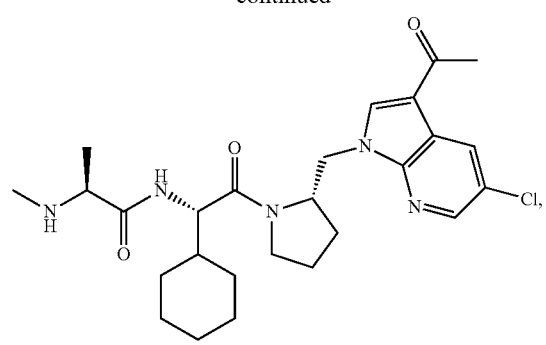
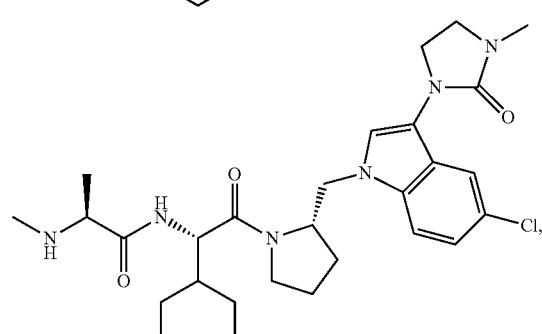
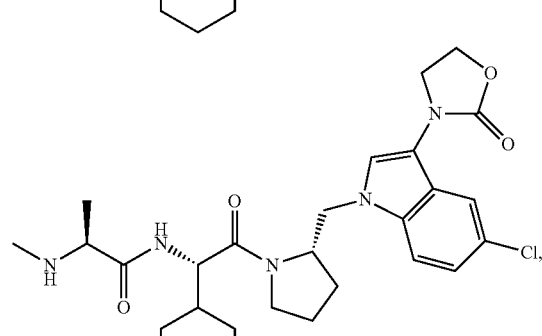
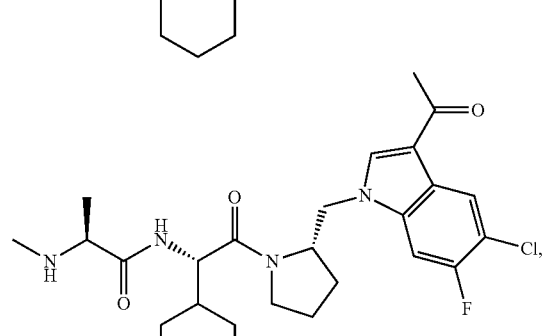
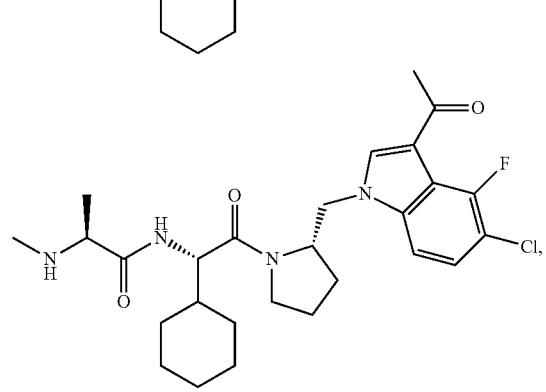

-continued

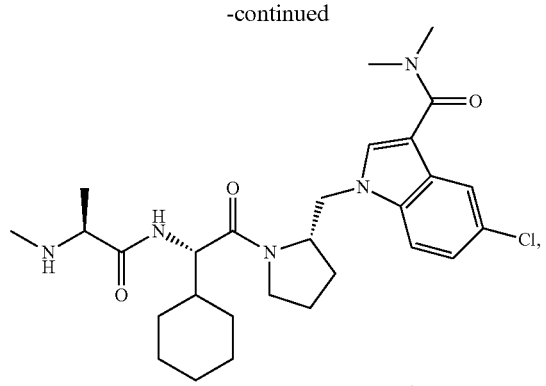

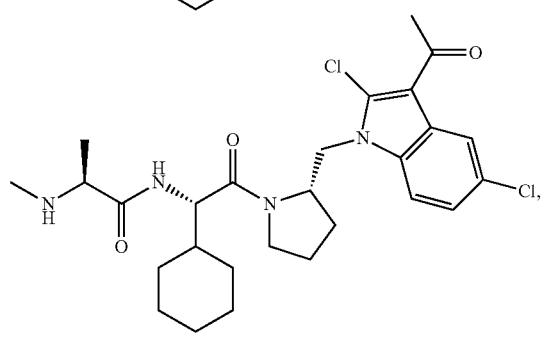

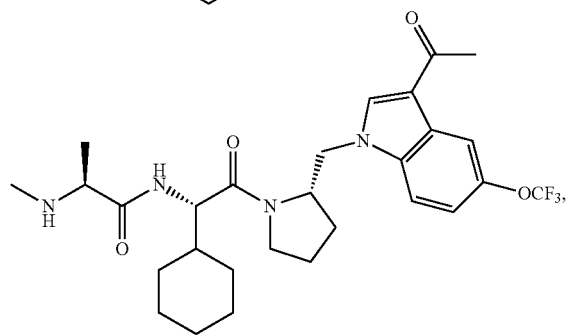

-continued

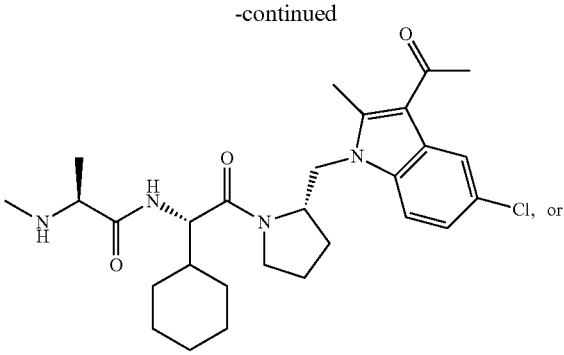

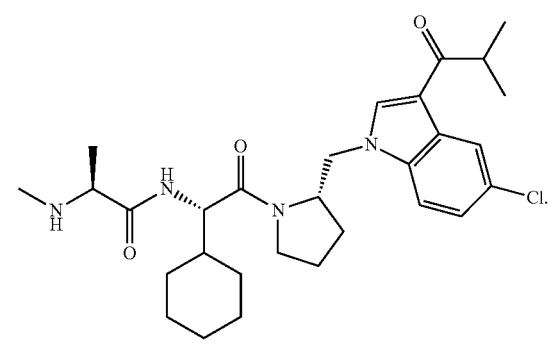

18. A pharmaceutical composition, comprising a therapeutically effective amount of the compound according to claim 1 or a pharmaceutically acceptable salt thereof as an active ingredient, and a pharmaceutically acceptable carrier.

19. A method for treating cancer, comprising administering an effective amount of the compound according to claim 1 or a pharmaceutically acceptable salt thereof to a subject in need thereof;

wherein the cancer is breast cancer.

* * * * *

UNITED STATES PATENT AND TRADEMARK OFFICE
CERTIFICATE OF CORRECTION

| | |
|---|---|
| PATENT NO. | : 11,358,950 B2 |
| APPLICATION NO. | : 16/763746 |
| DATED | : June 14, 2022 |
| INVENTOR(S) | : Liu et al. |

It is certified that error appears in the above-identified patent and that said Letters Patent is hereby corrected as shown below:

On the Title Page

Item (73) (Assignee), Line 1, delete "TIANGQING" and insert -- TIANQING --.

Signed and Sealed this
Ninth Day of August, 2022

Katherine Kelly Vidal
*Director of the United States Patent and Trademark Office*